(12) United States Patent
Christian et al.

(10) Patent No.: US 8,129,415 B2
(45) Date of Patent: Mar. 6, 2012

(54) FUNGICIDE HYDROXIMOYL-TETRAZOLE DERIVATIVES

(75) Inventors: Isabelle Christian, Lyons (FR); Marie-Claire Grosjean-Cournoyer, Curis au Mont d'or (FR); Pierre Hutin, Lyons (FR); Philippe Rinolfi, Chatillon d'Azergues (FR); Arounarith Tuch, Lyons (FR); Jacky Vidal, Lozanne (FR)

(73) Assignee: Bayer Cropscience AG (DE)

( * ) Notice: Subject to any disclaimer, the term of this patent is extended or adjusted under 35 U.S.C. 154(b) by 438 days.

(21) Appl. No.: 12/309,339

(22) PCT Filed: Jul. 12, 2007

(86) PCT No.: PCT/EP2007/057158
§ 371 (c)(1),
(2), (4) Date: Jan. 13, 2009

(87) PCT Pub. No.: WO2008/006874
PCT Pub. Date: Jan. 17, 2008

(65) Prior Publication Data
US 2009/0192196 A1 Jul. 30, 2009

(30) Foreign Application Priority Data

Jul. 13, 2006 (EP) .................................... 06356092

(51) Int. Cl.
*C07D 401/14* (2006.01)
*A01N 43/713* (2006.01)

(52) U.S. Cl. ................. 514/333; 514/255.05; 514/256; 514/258.1; 514/307; 514/314; 514/340; 544/253; 544/333; 544/349; 544/405; 546/148; 546/152; 546/256; 546/268.4

(58) Field of Classification Search ........................ None
See application file for complete search history.

(56) References Cited

U.S. PATENT DOCUMENTS 5,461,049 A * 10/1995 O'Brien et al. ............ 514/210.2

FOREIGN PATENT DOCUMENTS

| EP | 1 184 382 | 3/2002 |
|----|-----------|--------|
| EP | 1426371 | 6/2004 |
| JP | 2004131392 | 4/2004 |
| JP | 2004131416 | 4/2004 |

OTHER PUBLICATIONS

U.S. Appl. No. 12/309,338, filed Mar. 11, 2009 by Isabelle Christian et al., entitled "Fungicide Hydroximoyl-Tetrazole Derivatives".
U.S. Appl. No. 12/309,340, filed Mar. 11, 2009 by Isabelle Christian et al., entitled "Fungicide Hydroximoyl-Tetrazole Derivatives".

* cited by examiner

*Primary Examiner* — Zinna Northington Davis
(74) *Attorney, Agent, or Firm* — Ostrolenk Faber LLP

(57) ABSTRACT

The present invention relates to hydroximoyl-tetrazole derivatives of formula (I) wherein T represent a tetrazolyl substituent, A represents a carbo- or heterocycle, $L^1$ and $L^2$ represent various linking groups and Q represents a 6-membered heterocycle, their process of preparation, their use as fungicide active agents, particularly in the form of fungicide compositions, and methods for the control of phytopathogenic fungi, notably of plants, using these compounds or compositions.

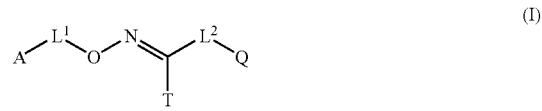

(I)

28 Claims, No Drawings

FUNGICIDE HYDROXIMOYL-TETRAZOLE DERIVATIVES

CROSS REFERENCE TO RELATED APPLICATION(S)

The present application is a 35 U.S.C. §371 national phase conversion of International Application No. PCT/EP2007/057158 filed Jul. 12, 2007, which claims priority of European Application No. 06356092.4 filed Jul. 13, 2006.

The present invention relates to hydroximoyl-tetrazoles derivatives, their process of preparation, their use as fungicide active agents, particularly in the form of fungicide compositions, and methods for the control of phytopathogenic fungi, notably of plants, using these compounds or compositions.

In European patent application no. 1426371, there are disclosed certain tetrazoyloxime derivatives of the following chemical structure:

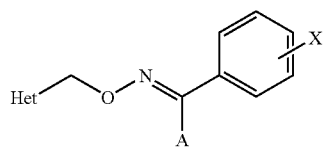

wherein A represents a tetrazolyl group, Het represents either a particular pyridinyl group or a particular thiazolyl group.

In Japanese patent application no. 2004-131392, there are disclosed certain tetrazoyloxime derivatives of the following chemical structure:

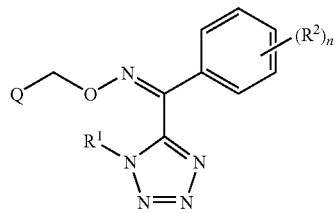

wherein Q can be selected in a list of 15 various heterocycle groups.

In European patent application no. 1184382, there are disclosed certain oxime derivatives of the following chemical structure:

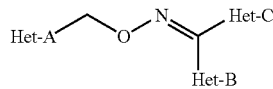

wherein Het-A, Het-B and Het-C represent various heterocycles whereby, Het-B and Het-C cannot represent a tetrazolyl group.

The compounds disclosed in these four documents do not prove to provide a comparable utility than the compounds according to the invention.

It is always of high-interest in agriculture to use novel pesticide compounds in order to avoid or to control the development of resistant strains to the active ingredients. It is of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides hydroximoyl-tetrazole derivatives of formula (I)

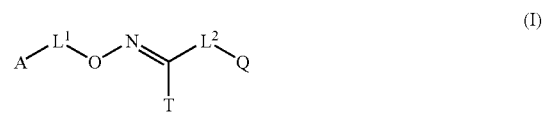

wherein
T represents a substituted or non-substituted tetrazolyl group;
$L^1$ represents a direct bond or a divalent group selected in the list consisting of
—$(CR^1R^2)_n$— —$(CR^1R^2)_m$—C(=O)—$(CR^1R^2)_p$—
—$(CR^1R^2)_m$—$(CR^1=CR^2)$—$(CR^1R^2)_p$—
—$(CR^1R^2)_m$—C(=O)—O—$(CR^1R^2)_p$—
—$(CR^1R^2)_m$—C≡C—$(CR^1R^2)_p$— —$(CR^1R^2)_m$—O—C(=O)—$(CR^1R^2)_p$—
—$(CR^1R^2)_m$—O—$(CR^1R^2)_p$— —$(CR^1R^2)_m$—C(=O)—NH—$(CR^1R^2)_p$—
—$(CR^1R^2)_m$—NH—$(CR^1R^2)_p$— —$(CR^1R^2)_m$—NH—C(=O)—$(CR^1R^2)_p$— wherein
n represents 1, 2, 3 or 4
m and p independently represent 0, 1, 2 or 3;
$L^2$ represents a direct bond or a divalent group selected in the list consisting of
—$(CR^3R^4)_q$— —$(CR^3R^4)_a$—C(=O)—$(CR^3R^4)_b$—
—$(CR^3R^4)_a$—$(CR^3=CR^4)$—$(CR^3R^4)_b$— —$(CR^3R^4)_a$—C(=O)—O—$(CR^3R^4)_b$—
—$(CR^3R^4)_a$—C≡C—$(CR^3R^4)_b$— —$(CR^3R^4)_a$—O—C(=O)—$(CR^3R^4)_b$
—$(CR^3R^4)_a$—O—$(CR^3R^4)_b$— —$(CR^3R^4)_a$—C(=O)—NH—$(CR^3R^4)_b$—
—$(CR^3R^4)_a$—NH—$(CR^3R^4)_b$— —$(CR^3R^4)_a$—NH—C(=O)—$(CR^3R^4)_b$— wherein
q represents 1, 2, 3 or 4;
a and b independently represent 0, 1, 2 or 3;
A is selected in the list consisting of $A^1$ to $A^{116}$

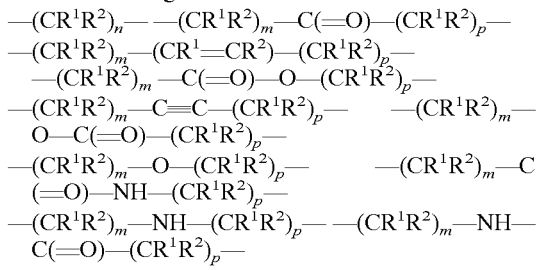

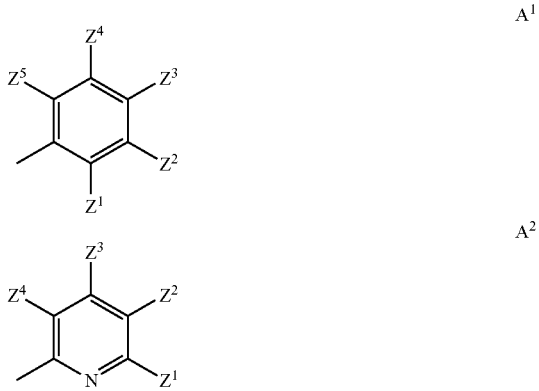

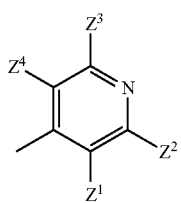 A³
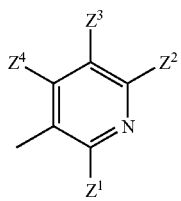 A⁴
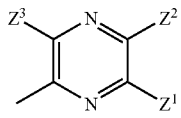 A⁵
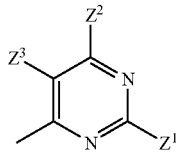 A⁶
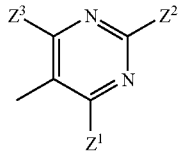 A⁷
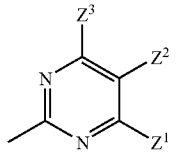 A⁸
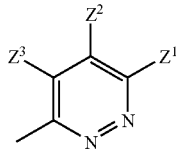 A⁹
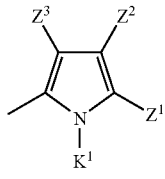 A¹⁰
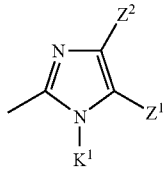 A¹¹
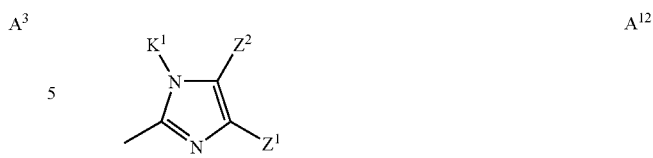 A¹²
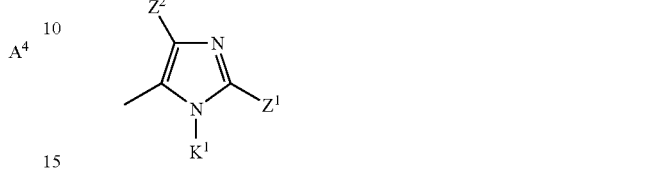 A¹³
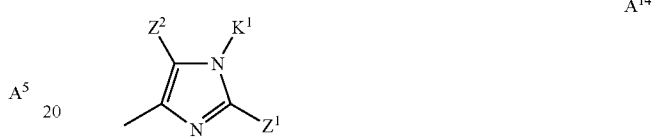 A¹⁴
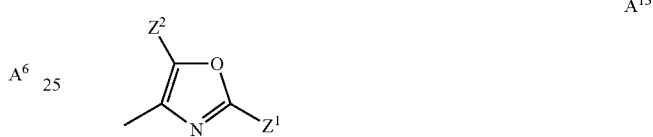 A¹⁵
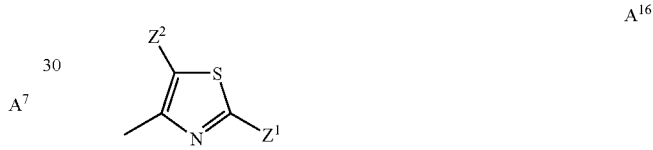 A¹⁶
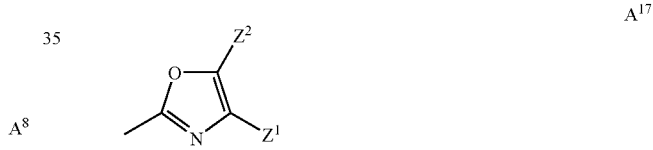 A¹⁷
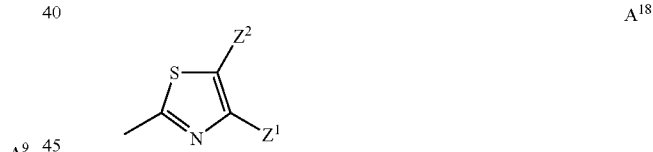 A¹⁸
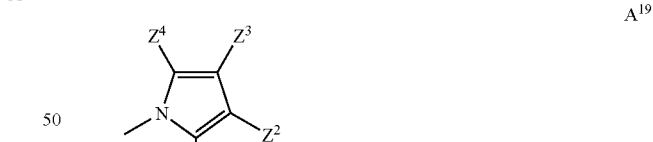 A¹⁹
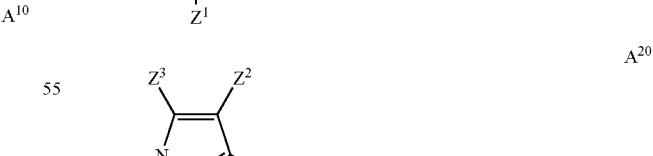 A²⁰
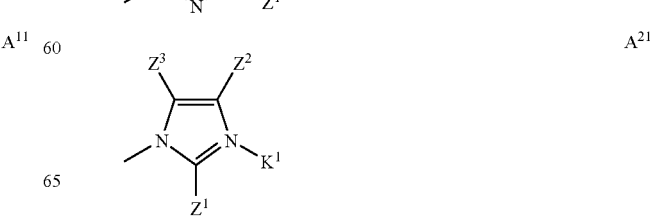 A²¹

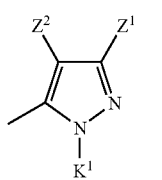
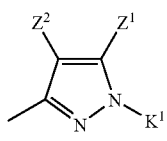
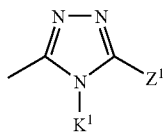
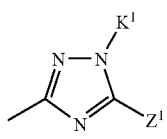
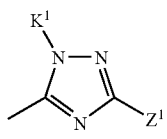
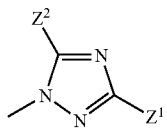
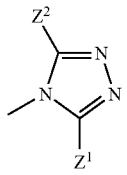
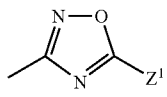
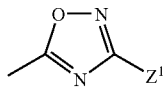
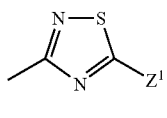
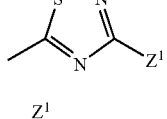
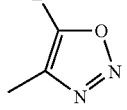
$A^{22}$
$A^{23}$
$A^{24}$
$A^{25}$
$A^{26}$
$A^{27}$
$A^{28}$
$A^{29}$
$A^{30}$
$A^{31}$
$A^{32}$
$A^{33}$
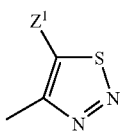
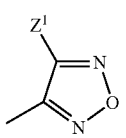
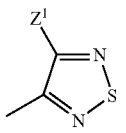
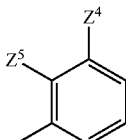
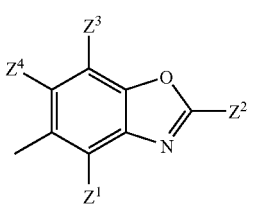
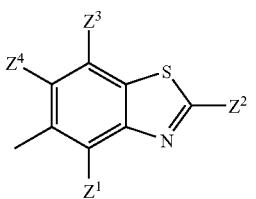
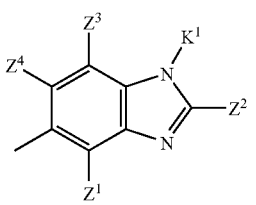
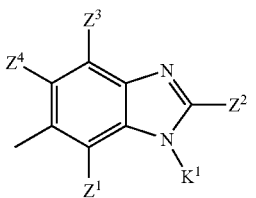
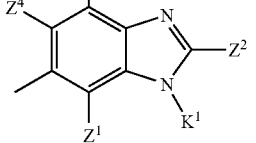
$A^{34}$
$A^{35}$
$A^{36}$
$A^{37}$
$A^{38}$
$A^{39}$
$A^{40}$
$A^{41}$

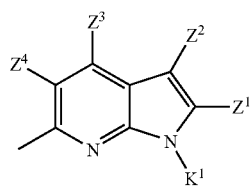
A⁴²
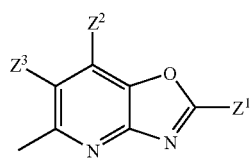
A⁴³
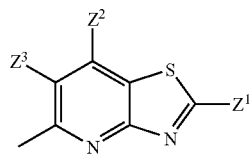
A⁴⁴
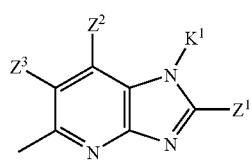
A⁴⁵
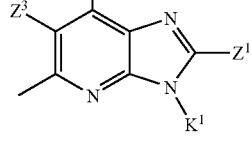
A⁴⁶
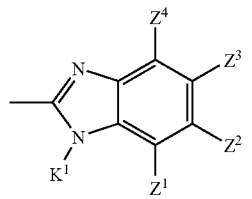
A⁴⁷
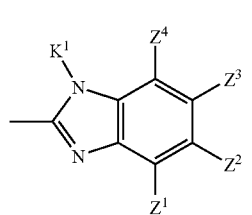
A⁴⁸
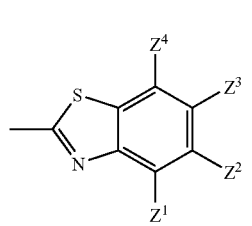
A⁴⁹
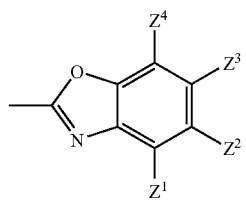
A⁵⁰
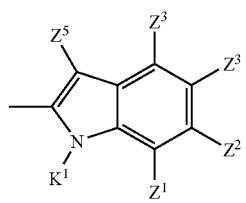
A⁵¹
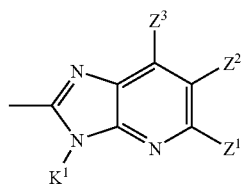
A⁵²
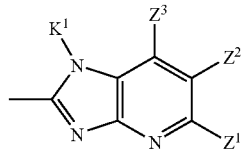
A⁵³
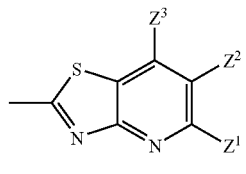
A⁵⁴
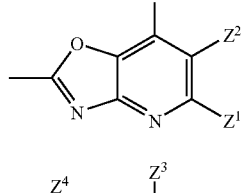
A⁵⁵
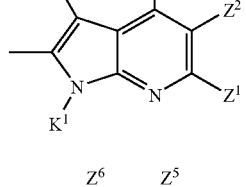
A⁵⁶
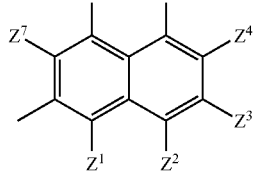
A⁵⁷

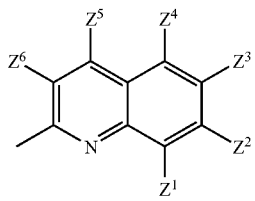 A58
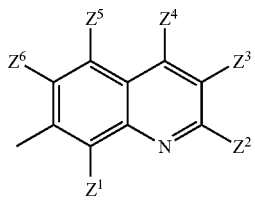 A59
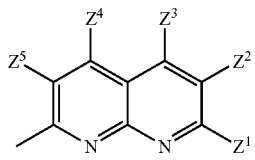 A60
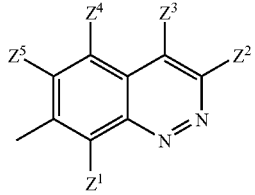 A61
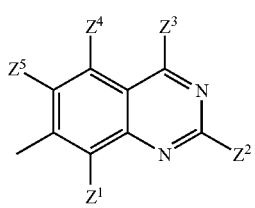 A62
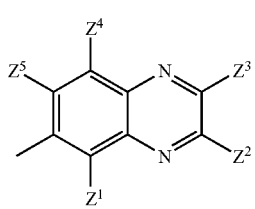 A63
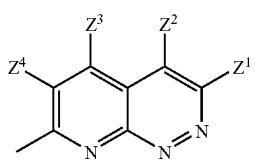 A64
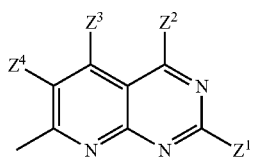 A65
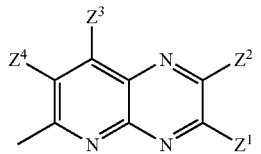 A66
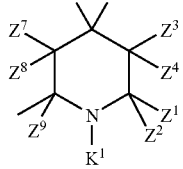 A67
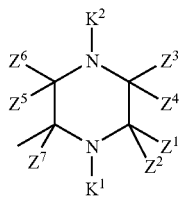 A68
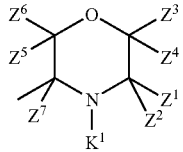 A69
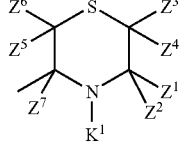 A70
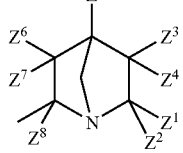 A71
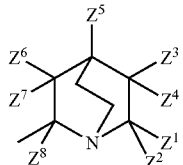 A72
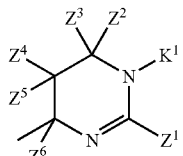 A73
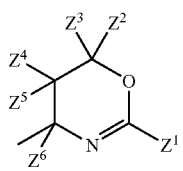 A74

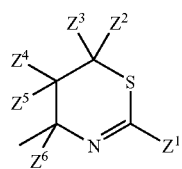 A75
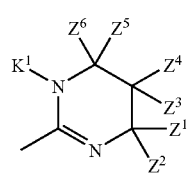 A76
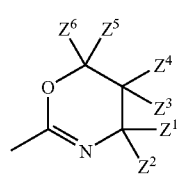 A77
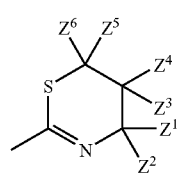 A78
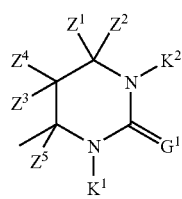 A79
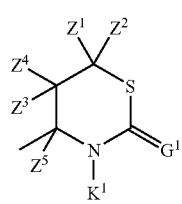 A80
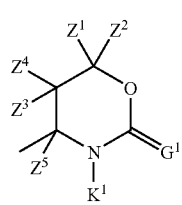 A81
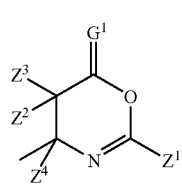 A82
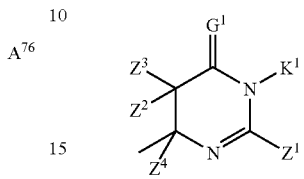 A83
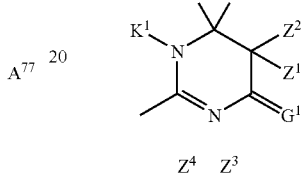 A84
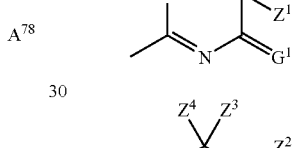 A85
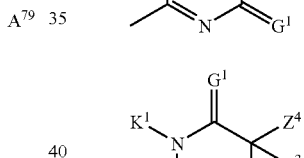 A86
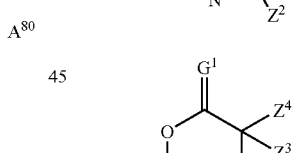 A87
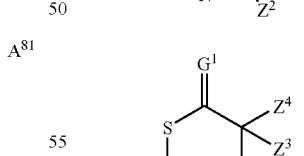 A88
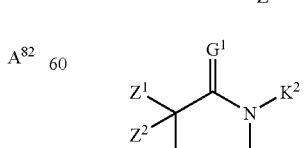 A89
 A90
A91

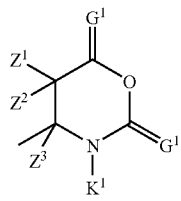 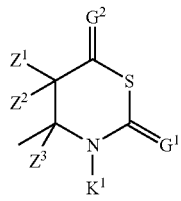 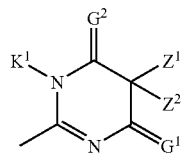 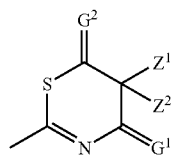 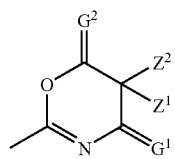 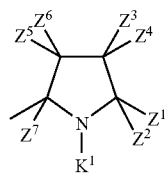 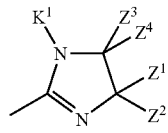 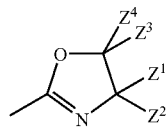 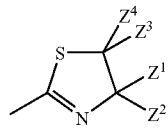 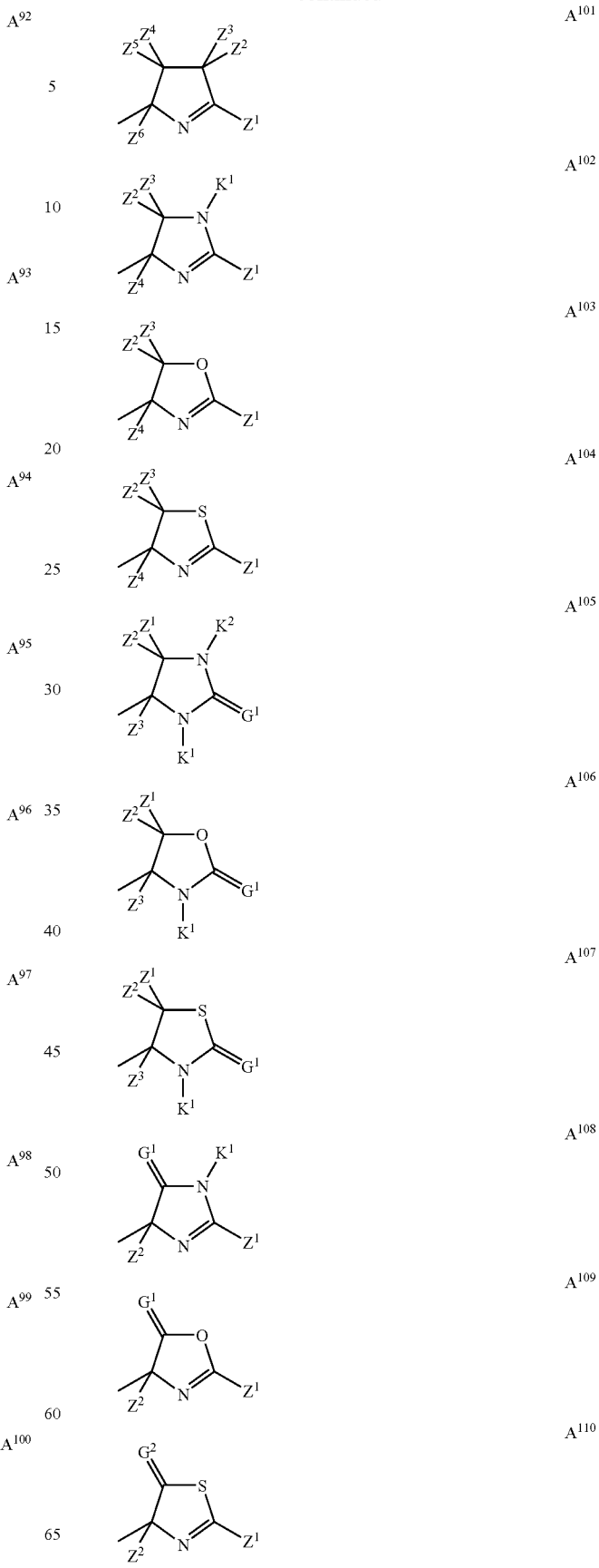

-continued

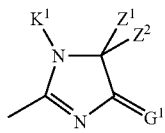
A<sup>111</sup>

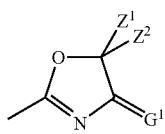
A<sup>112</sup>

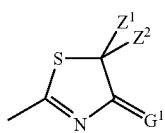
A<sup>113</sup>

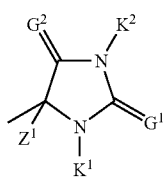
A<sup>114</sup>

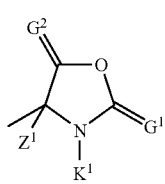
A<sup>115</sup>

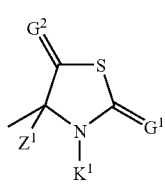
A<sup>116</sup> wherein $Z^1$, $Z^2$, $Z^3$, $Z^4$, $Z^5$, $Z^6$, $Z^7$, $Z^8$ and $Z^9$ are independently selected in the list consisting of hydrogen, halogen, [$C_1$-$C_8$]-alkyl, [$C_1$-$C_8$]-haloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_3$-$C_6$]-cycloalkyl, [$C_3$-$C_8$]-halocycloalkyl, aryl, aryl-[$C_1$-$C_8$]-alkyl, hydroxy-[$C_1$-$C_8$]-alkyl, [$C_1$-$C_8$]-alkoxy-[$C_1$-$C_8$]-alkyl, —C(=O)$R^5$, —C(=O)O$R^5$, —C(=O)N$R^5R^6$, —C(=O)S$R^5$, —C(=S)$R^5$, —C(=S)O$R^5$, —C(=S)N$R^5R^6$, —C(=S)S$R^5$, —C$R^5$=N$R^6$, —C$R^5$=NO$R^6$, —C$R^5$=N—N$R^6R^7$, —O$R^5$, —OSi$R^5R^6R^7$, —OC(=O)$R^5$, —OC(=O)O$R^5$, —OC(=O)N$R^5R^6$, —OC(=S)N$R^5R^6$, —N$R^5R^6$, —N($R^5$)C(=O)$R^6$, —N($R^5$)C(=O)O$R^6$, —N($R^5$)C(=O)N$R^6R^7$, —N($R^5$)C(=S)$R^6$, —N($R^5$)C(=S)N$R^6R^7$, —N=C$R^5R^6$, —N=C—N$R^5R^6$, —N($R^5$)C(=N$R^6$)N$R^7R^8$, —N($R^5$)O$R^6$, —N($R^5$)N$R^6R^7$, —N=N$R^5$, —N($R^5$)S(=O)$R^6$, —N($R^5$)S(=O)$_2R^6$, —N($R^5$)S(=O)$_2$O$R^6$, —N($R^5$)S(=O)O$R^6$, —N($R^5$)S(=O)N$R^6R^7$, —N($R^5$)S(=O)$_2$N$R^6R^7$, —S$R^5$, —S(=O)$R^5$, —S(=O)$_2R^5$, —S(=O)O$R^5$, —S(=O)N$R^5R^6$, —S(=O)$_2$O$R^5$, —S(=O)$_2$N$R^5R^6$, nitro, nitroso, azido, cyano, —SF$_5$ and —Si$R^5R^6R^7$;

$K^1$ and $K^2$ are independently selected in the list consisting of hydrogen, [$C_1$-$C_8$]-alkyl, [$C_1$-$C_8$]-haloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_3$-$C_6$]cycloalkyl, [$C_3$-$C_6$]-halocycloalkyl, aryl, aryl-[$C_1$-$C_8$]-alkyl, hydroxy-[$C_1$-$C_8$]-alkyl, [$C_1$-$C_8$]-alkoxy-[$C_1$-$C_8$]-alkyl, —C(=O)$R^9$, —C(=O)O$R^9$, —C(=O)N$R^9R^{10}$, —C(=O)S$R^9$, —C(=S)$R^9$, —C(=S)O$R^9$, —C(=S)N$R^9R^{10}$, —C(=S)S$R^9$, —C$R^9$=N$R^{10}$, —C$R^9$=NO$R^{10}$, —C$R^9$=N—N$R^{10}R^{11}$, —S(=O)$R^9$, —S(=O)$_2R^9$, —S(=O)O$R^9$, —S(=O)N$R^9R^{10}$, —S(=O)$_2$O$R^9$, —S(=O)$_2$N$R^9R^{10}$ and —Si$R^9R^{10}R^{11}$;

$G^1$ and $G^2$ are independently selected in the list consisting of oxygen, sulfur, N$R^{12}$, N—O$R^{12}$ and N—N$R^{12}R^{13}$;

Q is selected in the list consisting of $Q^1$ to $Q^{28}$

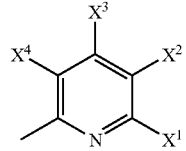
Q<sup>1</sup>

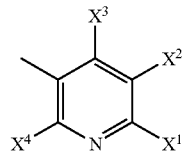
Q<sup>2</sup>

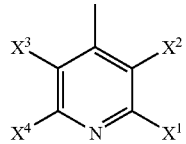
Q<sup>3</sup>

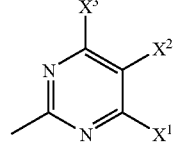
Q<sup>4</sup>

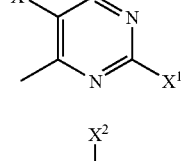
Q<sup>5</sup>

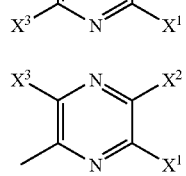
Q<sup>6</sup>

Q<sup>7</sup>

-continued
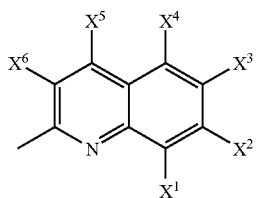 Q⁸
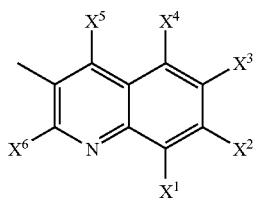 Q⁹
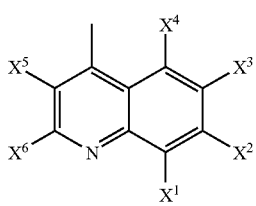 Q¹⁰
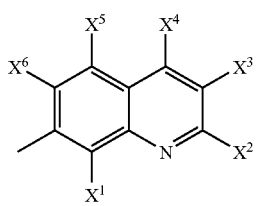 Q¹¹
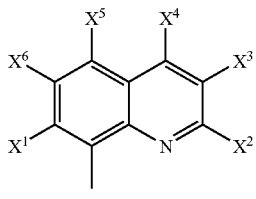 Q¹²
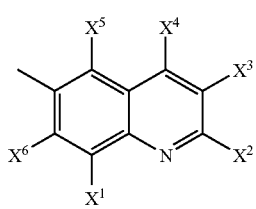 Q¹³
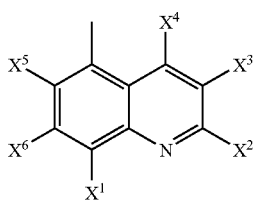 Q¹⁴
-continued
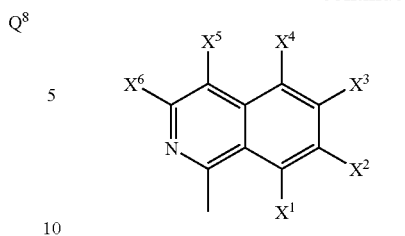 Q¹⁵
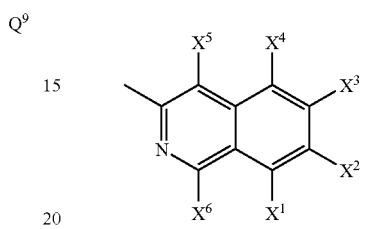 Q¹⁶
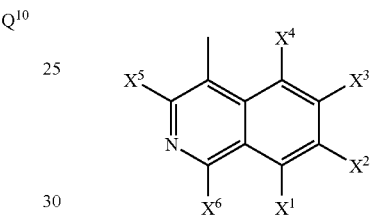 Q¹⁷
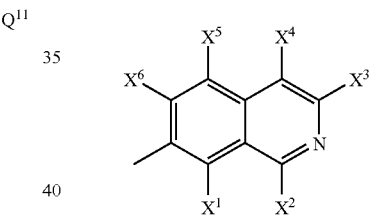 Q¹⁸
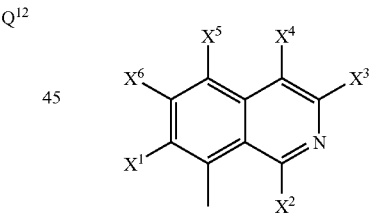 Q¹⁹
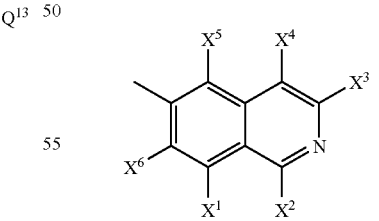 Q²⁰
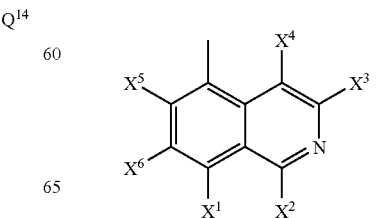 Q²¹

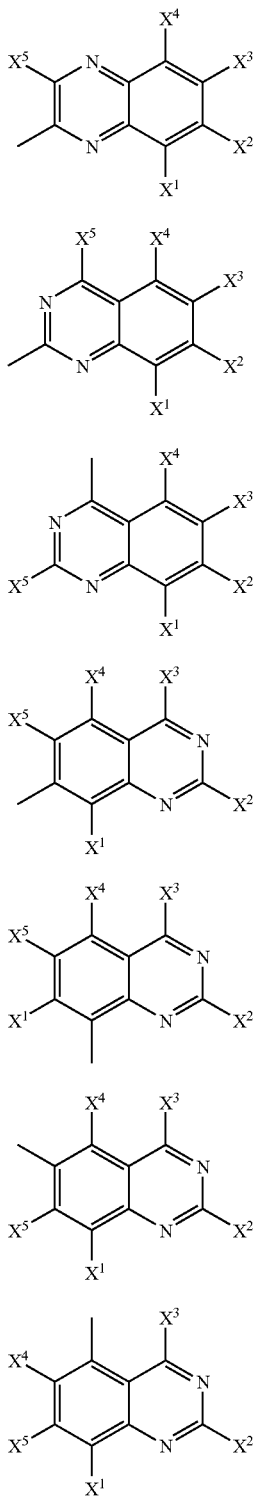

wherein $X^1$, $X^2$, $X^3$, $X^4$, $X^1$ and $X^6$ are independently selected in the list consisting of hydrogen, halogen, $[C_1\text{-}C_8]$-alkyl, $[C_1\text{-}C_8]$-haloalkyl, $[C_2\text{-}C_8]$-alkenyl, $[C_2\text{-}C_8]$-haloalkenyl, $[C_2\text{-}C_8]$-alkynyl, $[C_2\text{-}C_8]$-haloalkynyl, $[C_3\text{-}C_6]$-cycloalkyl, $[C_3\text{-}C_6]$-halocycloalkyl, aryl, aryl-$[C_1\text{-}C_8]$-alkyl, hydroxy-$[C_1\text{-}C_8]$-alkyl, $[C_1\text{-}C_8]$-alkoxy-$[C_1\text{-}C_8]$-alkyl, $-C(=O)R^4$, $-C(=O)OR^{14}$, $-C(=O)NR^{14}R^{15}$, $-C(=O)SR^{14}$, $-C(=S)R^{14}$, $-C(=S)OR^{14}$, $-C(=S)NR^{14}R^{15}$, $-C(=S)SR^{14}$, $-CR^{14}=NR^{15}$, $-CR^{14}=NOR^{15}$, $-CR^{14}=N-NR^{15}R^{16}$, $-OR^{14}$, $-OSiR^{14}R^{15}R^{16}$, $-OC(=O)R^{14}$, $-OC(=O)OR^{14}$, $-OC(=O)NR^{14}R^{15}$, $-OC(=S)NR^{14}R^{15}$, $-NR^{14}R^{15}$, $-N(R^{14})C(=O)R^{15}$, $-N(R^{14})C(=O)OR^{15}$, $-N(R^{14})C(=O)NR^{15}R^{16}$, $-N(R^{14})C(=S)R^{15}$, $-N(R^{14})C(=S)NR^{15}R^{16}$, $-N=CR^{14}R^{15}$, $-N=C-NR^{14}R^{15}$, $-N(R^{14})C(=NR^{15})NR^{16}R^{17}$, $-N(R^{14})OR^{15}$, $-N(R^{14})NR^{15}R^{16}$, $-N=NR^{14}$, $-N(R^{14})S(=O)R^{15}$, $-N(R^{14})S(=O)_2R^{15}$, $-N(R^{14})S(=O)_2OR^{15}$, $-N(R^{14})S(=O)OR^{15}$, $-N(R^{14})S(=O)NR^{15}R^{16}$, $-N(R^{14})S(=O)R^{15}R^{16}$, $-SR^{14}$, $-S(=O)R^{14}$, $-S(=O)_2R^{14}$, $-S(=O)OR^{14}$, $-S(=O)NR^{14}R^{15}$, $-S(=O)_2OR^{14}$, $-S(=O)_2NR^4R^5$, nitro, nitroso, azido, cyano, $-SF_5$ and $-SiR^{14}R^{15}R^{16}$;

$R^1$, $R^2$, $R^3$ and $R^4$ are independently selected in the list consisting of hydrogen, halogen, $[C_1\text{-}C_4]$-alkyl, $[C_1\text{-}C_4]$-haloalkyl, $[C_2\text{-}C_4]$-alkenyl, $[C_2\text{-}C_4]$-haloalkenyl, $[C_2\text{-}C_4]$-alkynyl, $[C_2\text{-}C_4]$-haloalkynyl, $[C_3\text{-}C_5]$-cycloalkyl, $[C_3\text{-}C_5]$-halocycloalkyl, $[C_1\text{-}C_4]$-alkoxy, $[C_1\text{-}C_4]$-alkoxy-$[C_1\text{-}C_4]$-alkyl, $[C_1\text{-}C_4]$-alkoxy-$[C_1\text{-}C_4]$-alkoxy, $[C_1\text{-}C_4]$-haloalkoxy, $[C_1\text{-}C_4]$-haloalkoxy-$[C_1\text{-}C_4]$-alkyl and cyano;

$R^5$ to $R^{17}$ are independently selected in the list consisting of hydrogen, $[C_1\text{-}C_8]$-alkyl, $[C_1\text{-}C_8]$-haloalkyl, $[C_2\text{-}C_8]$-alkenyl, $[C_2\text{-}C_8]$-haloalkenyl, $[C_2\text{-}C_8]$-alkynyl, $[C_2\text{-}C_8]$-haloalkynyl, $[C_3\text{-}C_6]$-cycloalkyl, $[C_3\text{-}C_6]$-halocycloalkyl, aryl and aryl-$[C_1\text{-}C_8]$-alkyl;

as well as salts, N-oxides, metallic complexes and metalloidic complexes thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

According to the invention, the following generic terms are generally used with the following meanings:

halogen means fluorine, chlorine, bromine or iodine;

heteroatom can be nitrogen, oxygen or sulphur;

halogenated groups, notably haloalkyl, haloalkoxy and cycloalkyl groups, may comprise up to nine identical or different halogen atoms;

the term "aryl" means phenyl or naphthyl, optionally substituted by one to five groups selected in the list consisting of halogen, $[C_1\text{-}C_6]$-alkyl, $[C_1\text{-}C_6]$-haloalkyl, $[C_2\text{-}C_6]$-alkenyl, $[C_2\text{-}C_6]$-haloalkenyl, $[C_2\text{-}C_6]$-alkynyl, $[C_2\text{-}C_6]$-haloalkynyl, $[C_1\text{-}C_6]$-alkoxy, $[C_1\text{-}C_4]$-alkoxy-$[C_1\text{-}C_4]$-alkyl, $[C_1\text{-}C_4]$-alkoxy-$[C_1\text{-}C_4]$-alkoxy, $[C_1\text{-}C_6]$-haloalkoxy and $[C_1\text{-}C_4]$-haloalkoxy-$[C_1\text{-}C_4]$-alkyl.

As a further aspect, the present invention provides hydroximoyl-tetrazole derivatives of formula (Ia), (Ib), (Ic) and (Id)

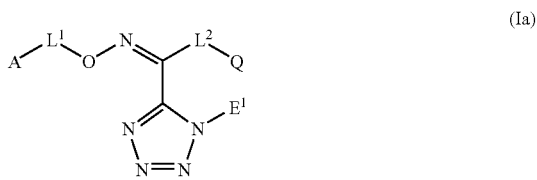

(Ia)

-continued (Ib)

(Ic)

(Id)

wherein
- A, Q, $L^1$ and $L^2$ are defined in the same manner as the corresponding substituents of the compounds of formula (I) according to the invention;
- $E^1$ is selected in the list consisting of hydrogen, [$C_1$-$C_8$]-alkyl, [$C_1$-$C_8$]-haloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_3$-$C_6$]-cycloalkyl, [$C_3$-$C_6$]-halocycloalkyl, aryl, aryl-[$C_1$-$C_8$]-alkyl, hydroxy-[$C_1$-$C_8$]-alkyl, [$C_1$-$C_8$]-alkoxy-[$C_1$-$C_8$]-alkyl, —C(=O)$R^{18}$, —C(=O)O$R^{18}$, —C(=O)N$R^{18}R^{19}$, —C(=O)S$R^{18}$, —C(=S)$R^{18}$, —C(=S)O$R^{18}$, —C(=S)N$R^{18}R^{19}$, —C(=S)S$R^{18}$, —C$R^{18}$=N$R^9$, —C$R^{18}$=NO$R^{19}$, —C$R^8$=N—N$R^{19}R^{20}$, —S(=O)$R^{18}$, —S(=O)$_2R^{18}$, —S(=O)O$R^{18}$, —S(=O)N$R^{18}R^{19}$, —S(=O)$_2$O$R^{18}$, —S(=O)$_2$N$R^{18}R^{19}$, cyano, and —Si$R^{18}R^{19}R^{20}$;
- $E^2$ is selected in the list consisting of hydrogen, halogen, [$C_1$-$C_8$]-alkyl, [$C_1$-$C_8$]-haloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_3$-$C_8$]cycloalkyl, [$C_3$-$C_6$]-halocycloalkyl, aryl, aryl-[$C_1$-$C_8$]-alkyl, hydroxy-[$C_1$-$C_8$]-alkyl, [$C_1$-$C_8$]-alkoxy-[$C_1$-$C_8$]-alkyl, —C(=O)$R^{18}$, —C(=O)O$R^{18}$, —C(=O)N$R^{18}R^{19}$, —C(=O)S$R^{18}$, —C(=S)$R^{18}$, —C(=S)O$R^{18}$, —C(=S)N$R^{18}R^{19}$, —C(=S)S$R^{18}$, —C$R^8$=N$R^{19}$, —C$R^{18}$=NO$R^{19}$C$R^{18}$=N—N$R^{19}R^{20}$, —O$R^{18}$, —OSi$R^{18}R^{19}R^{20}$, —OC(=O)$R^{18}$, —OC(=O)O$R^{18}$, —OC(=O)N$R^{18}R^{19}$, —OC(=S)N$R^{18}R^{19}$, —N$R^{18}R^{19}$, —N($R^{18}$)C(=O)$R^{19}$, —N($R^{18}$)C(=O)O$R^{19}$, —N($R^{18}$)C(=O)N$R^{19}R^{20}$, —N($R^{18}$)C(=S)$R^{19}$, —N($R^{18}$)C(=S)N$R^{19}R^{20}$, —N=C$R^{18}R^{19}$, —N=C—N$R^{18}R^{19}$, —N($R^{18}$)C(=N$R^{19}$)N$R^2$O$R^2$, —N($R^{18}$)O$R^{19}$, —N($R^{18}$)N$R^{19}R^{20}$, —N=N$R^{28}$—N($R^{18}$)S(=O)$R^{19}$—N($R^{18}$)S(=O)$_2R^{19}$, —N($R^{18}$)S(=O)$_2$O$R^{19}$, —N($R^{18}$)S(=O)O$R^{19}$, —N($R^{18}$)S(=O)N$R^{19}R^{20}$, —N($R^{18}$)S(=O)$_2$N$R^{19}R^{20}$, —S$R^{18}$, —S(=O)$R^{18}$, —S(=O$_2$$R^{18}$, —S(=O)O$R^{18}$, —S(=O)N$R^{18}R^{19}$, —S(=O)$_2$O$R^{18}$, —S(=O)$_2$N$R^{18}R^{19}$, cyano, —SF$_5$ and —Si$R^{18}R^{19}R^{20}$;
- $R^{18}$ to $R^{20}$ are independently selected in the list consisting of hydrogen, [$C_1$-$C_8$]-alkyl, [$C_1$-$C_8$]-haloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_3$-$C_6$]-cycloalkyl, [$C_3$-$C_6$]-halocycloalkyl, aryl and aryl-[$C_1$-$C_8$]-alkyl.

Preferred compounds of formula (I) and (Ia) to (Id) according to the invention are those wherein $L^1$ represents a direct bond or a divalent group selected in the list consisting of
—(C$R^1R^2$)$_n$— —C(=O)—(C$R^1R^2$)$_p$—
—(C$R^1R^2$)$_m$—O— —(C$R^1R^2$)$_m$—C(=O)—O—
—(C$R^1R^2$)$_m$—NH— —(C$R^1R^2$)$_m$—C(=O)—NH—
—(C$R^1R^2$)$_m$—C(=O)— —(C$R^1R^2$)$_m$—NH—C(=O)
wherein
- n represents 1 or 2;
- m and p independently represent 0 or 1;
- $R^1$ and $R^2$ are independently selected in the list consisting of hydrogen, halogen, [$C_1$-$C_4$]-alkyl, [$C_1$-$C_4$]-haloalkyl, [$C_2$-$C_4$]-alkenyl, [$C_2$-$C_4$]-alkynyl, [$C_3$-$C_5$]-cycloalkyl, [$C_1$-$C_4$]-alkoxy, [$C_1$-$C_4$]-haloalkoxy and cyano.

More preferred compounds of formula (I) and (Ia) to (Id) according to the invention are those wherein $L^1$ represents a direct bond or a divalent group selected in the list consisting of —(C$R^1R^2$)—, —C(=O)—(C$R^1R^2$)— and —C(=O)—; wherein $R^1$ and $R^2$ are independently selected in the list consisting of hydrogen, halogen, methyl, ethyl, iso-propyl, trifluoromethyl, difluoromethyl, allyl, ethynyl, propargyl, cyclopropyl, methoxy, trifluoromethoxy and cyano.

Other preferred compounds of formula (I) and (Ia) to (Id) according to the invention are those wherein $L^2$ represents a direct bond or a divalent group selected in the list consisting of
—(C$R^3R^4$)$_q$— —(C$R^3R^4$)$_a$—C(=O)—
—(C$R^3$=C$R^4$)— —(C$R^3R^4$)$_a$—C(=O)—O—
—C≡C— —(C$R^3R^4$)$_a$—O—C(=O)—
—(C$R^3R^4$)$_a$—O— —(C$R^3R^4$)$_a$—C(=O)—NH—
—(C$R^3R^4$)$_a$—NH— —(C$R^3R^4$)$_a$—NH—C(=O)—
wherein
- q and a independently represent 1 or 2;
- $R^3$ and $R^4$ are independently selected in the list consisting of hydrogen, halogen, [$C_1$-$C_4$]-alkyl, [$C_1$-$C_4$]-haloalkyl, [$C_2$-$C_4$]-alkenyl, [$C_2$-$C_4$]-alkynyl, [$C_3$-$C_5$]-cycloalkyl, [$C_1$-$C_4$]-alkoxy, [$C_1$-$C_4$]-haloalkoxy and cyano.

Other more preferred compounds of formula (I) and (Ia) to (Id) according to the invention are those wherein $L^2$ represents a direct bond or —(C$R^3R^4$)— wherein $R^3$ and $R^4$ are independently selected in the list consisting of hydrogen, halogen, methyl, ethyl, iso-propyl, trifluoromethyl, difluoromethyl, allyl, ethynyl, propargyl, cyclopropyl, methoxy, trifluoromethoxy and cyano.

Still other preferred compounds of formula (I) and (Ia) to (Id) according to the invention are those wherein A is selected in the list consisting of $A^1$ to $A^{32}$.

Other more preferred compounds of formula (I) and (Ia) to (Id) according to the invention are those wherein A is selected in the list consisting of $A^2$, $A^6$, $A^8$, $A^{15}$, $A^{16}$, $A^{17}$ and $A^{18}$.

Other more preferred compounds of formula (I) and (Ia) to (Id) according to the invention are those wherein $Z^1$ is selected in the list consisting of hydrogen, —C(=O)$R^5$, —C(=O)O$R^5$, —C(=O)N$R^5R^6$, —C(=S)N$R^5R^6$, —C$R^5$=N$R^6$, —C$R^5$=NO$R^6$, —C$R^5$=N—N$R^6R^7$, —O$R^5$, —OC(=O)$R^5$, —OC(=O)O$R^5$, —OC(=O)N$R^5R^6$, —OC(=S)N$R^5R^6$, —N$R^5R^6$, —N($R^5$)C(=O)$R^6$, —N($R^5$)C(=O)O$R^6$, —N($R^5$)C(=O)N$R^6R^7$, —N($R^5$)C(=S)$R^6$, —N($R^5$)C(=S)N$R^6R^7$, —N=C$R^5R^6$, —N=C—N$R^5R^6$, —N($R^5$)C(=N$R^6$)N$R^7R^8$, —N($R^5$)O$R^6$, —N($R^5$)N$R^6R^7$, —N=N$R^5$, —N($R^5$)S(=O)$_2R^6$, —N($R^5$)S(=O)$_2$O$R^7$, —N($R^5$)S(=O)$_2$N$R^6R^7$, —S$R^5$, —S(=O)$_2R^5$, —S(=O)$_2$O$R^5$, —S(=O)$_2$N$R^5R^3$ and cyano.

Other even more preferred compounds of formula (I) and (Ia) to (Id) according to the invention are those wherein $Z^1$ is selected in the list consisting of hydrogen, —NR$^5$R$^6$, —N(R$^5$)C(=O)R$^6$, —N(R$^5$)C(=O)OR$^6$, —N(R$^5$)C(=O)NR$^6$R$^7$, —N(R$^5$)C(=S)NR$^6$R$^7$, —N=CR$^5$R$^6$, —N=C—NR$^5$R$^6$, —N(R$^5$)C(=NR$^6$)NR$^7$R$^8$, —N(R$^5$)S(=O)$_2$R$^6$, —N(R$^5$)S(=O)$_2$OR$^6$, —N(R$^5$)S(=O)$_2$NR$^6$R$^7$ and cyano.

Still other preferred compounds of formula (I) and (Ia) to (Id) according to the invention are those wherein Z$^2$, Z$^3$, Z$^4$, Z$^5$, Z$^6$, Z$^7$, Z$^8$ and Z$^9$ are independently selected in the list consisting of hydrogen, halogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, —C(=O)R$^5$, —C(=O)OR$^5$, —C(=O)NR$^5$R$^6$, —OR$^5$, —OSiR$^5$R$^6$R$^7$, —OC(=O)R$^5$, —NR$^5$R$^6$, —N(R$^5$)C(=O)R$^6$, —SR$^5$, —S(=O)R$^5$, —S(=O)$_2$OR$^5$, —S(=O)$_2$NR$^5$R$^6$, cyano and —SiR$^5$R$^6$R$^7$; wherein R$^5$, R$^6$, and R$^7$ are independently selected in the list consisting of hydrogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl and [$C_3$-$C_5$]-cycloalkyl.

Other more preferred compounds of formula (I) and (Ia) to (Id) according to the invention are those wherein Z$^2$, Z$^3$, Z$^4$, Z$^5$, Z$^6$, Z$^7$, Z$^8$ and Z$^9$ are independently selected in the list consisting of hydrogen, halogen, [$C_1$-$C_4$]-alkyl, methyl, ethyl, iso-propyl, iso-butyl, tert-butyl, [$C_1$-$C_4$]-haloalkyl, trifluoromethyl, difluoromethyl, allyl, ethynyl, propargyl, cyclopropyl, methoxy, trifluoromethoxy, acetyl, trifluoroacetyl and cyano.

Still other preferred compounds of formula (I) and (Ia) to (Id) according to the invention are those wherein K$^1$ and K$^2$ are independently selected in the list consisting of hydrogen, [$C_1$-$C_4$]-alkyl, methyl, ethyl, iso-propyl, isobutyl, tert-butyl, allyl, propargyl, cyclopropyl, acetyl, trifluoroacetyl and mesyl.

Still other preferred compounds of formula (I) and (Ia) to (Id) according to the invention are those wherein Q is selected in the list consisting of Q$^1$ to Q$^{14}$.

Other more preferred compounds of formula (I) and (Ia) to (Id) according to the invention are those wherein Q is selected in the list consisting of Q$^1$ to Q$^6$.

Still other preferred compounds of formula (I) and (Ia) to (Id) according to the invention are those wherein X$^1$ to X$^6$ are independently selected in the list consisting of hydrogen, halogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, [$C_3$-$C_5$]-halocycloalkyl, aryl, aryl-[$C_1$-$C_2$]-alkyl, —C(=O)R$^{14}$, —C(=O)OR$^{14}$, —C(=O)NR$^{14}$R$^{15}$, —CR$^{14}$=NOR$^{15}$, —CR$^{14}$=N—NR$^{15}$R$^{16}$, —OR$^{14}$, —OSiR$^{14}$R$^{15}$R$^{16}$, —OC(=O)R$^{14}$, —OC(=O)OR$^{14}$, —OC(=O)NR$^{14}$R$^{15}$, —NR$^{14}$R$^{15}$, —N(R$^{14}$)C(=O)R$^{15}$, —SR$^{14}$, —S(=O)$_2$R$^{14}$, —S(=O)$_2$OR$^{14}$, —S(=O)$_2$NR$^{14}$R$^{15}$, cyano and —SiR$^{14}$R$^{15}$R$^{16}$; wherein R$^{14}$, R$^{15}$, and R$^{16}$ are independently selected in the list consisting of hydrogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl and [$C_3$-$C_5$]-cycloalkyl, aryl and aryl-[$C_1$-$C_2$]-alkyl.

Other more preferred compounds of formula (I) and (Ia) to (Id) according to the invention are those wherein X$^1$ to X$^6$ are independently selected in the list consisting of hydrogen, halogen, [$C_1$-$C_4$]-alkyl, methyl, iso-propyl, iso-butyl, tert-butyl, [$C_1$-$C_4$]-haloalkyl, trifluoromethyl, difluoromethyl, allyl, ethynyl, propargyl, cyclopropyl, benzyl, phenethyl, methoxy, trifluoromethoxy, acetyl, trifluoroacetyl and cyano.

Preferred compounds of formula (Ia) to (Id) according to the invention are those wherein E$^1$ is selected in the list consisting of [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, [$C_3$-$C_5$]-halocycloalkyl, C(=O)R$^{18}$, —C(=O)OR$^{18}$, —C(=O)NR$^{18}$R$^{19}$, —CR$^{18}$=NR$^{19}$, —CR$^{18}$=NOR$^{19}$, —CR$^{18}$=N—NR$^{19}$R$^{20}$, —S(=O)$_2$R$^{18}$, —S(=O)$_2$OR$^{18}$, —S(=O)$_2$NR$^{18}$R$^{19}$, cyano and —SiR$^{18}$R$^{19}$R$^{20}$ wherein R$^{18}$, R$^{19}$ and R$^{20}$ are independently selected in the list consisting of hydrogen, [$C_1$-$C_4$]-alkyl, [$C_1$-$C_4$]-haloalkyl and cyclopropyl.

More preferred compounds of formula (Ia) to (Id) according to the invention are those wherein E$^1$ is selected in the list consisting of methyl, ethyl, iso-propyl, allyl, propargyl, cyclopropyl, —C(=O)R$^{18}$, —C(=O)OR$^{18}$, —C(=O)NR$^{18}$R$^{19}$, —CR$^{18}$=NR$^{19}$, —CR$^{18}$=NOR$^{19}$, —CR$^{18}$=N—NR$^{19}$R$^{20}$, —S(=O)$_2$R$^{18}$—S(=O)$_2$OR$^{18}$, —S(=O)$_2$NR$^{18}$R$^{19}$ and —SiR$^{18}$R$^{19}$R$^{10}$; wherein R$^{18}$, R$^{19}$ and R$^{20}$ are independently selected in the list consisting of methyl and trifluoromethyl.

Other preferred compounds of formula (Ia) to (Id) according to the invention are those wherein E$^2$ is selected in the list consisting of halogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, [$C_3$-$C_5$]-halocycloalkyl, —C(=O)R$^{18}$, —C(=O)OR$^8$, —C(=O)NR$^{18}$R$^{19}$, —CR$^{18}$=NOR$^{19}$, —CR$^{18}$=N—NR$^{19}$R$^{20}$, R$^{18}$, —OSiR$^{18}$R$^{19}$R$^{20}$, —OC(=O)R$^{18}$, —OC(=O)OR$^{18}$, —OC(=O)NR$^{18}$R$^{19}$, —NR$^{18}$R$^{19}$, —N(R$^{18}$)C(=O)R$^{19}$, —N(R$^{18}$)C(=O)OR$^{19}$, —N(R$^{18}$)C(=O)NR$^{19}$R$^{20}$, —N(R$^{18}$)C(=S)R$^{19}$, —N(R$^{18}$)C(=S)NR$^{19}$R$^{20}$, —N=CR$^{18}$R$^{19}$, —N=C—NR$^{18}$R$^{19}$, —N(R$^{18}$)S(=O)$_2$R$^{19}$, —N(R$^{18}$)S(=O)$_2$OR$^{19}$, —N(R$^{18}$)S(=O)$_2$NR$^{19}$R$^{20}$, —SR$^{18}$, —S(=O)R$^{18}$, —S(=O)$_2$OR$^{18}$, —S(=O)$_2$NR$^{18}$R$^{19}$, cyano and —SiR$^{18}$R$^{19}$R$^{20}$; wherein R$^{18}$, R$^{19}$ and R$^{20}$ are independently selected in the list consisting of hydrogen, [$C_1$-$C_4$]-alkyl and [$C_1$-$C_4$]-haloalkyl.

Other more preferred compounds of formula (Ia) to (Id) according to the invention are those wherein E$^2$ is selected in the list consisting of methyl, ethyl, iso-propyl, trifluoromethyl, difluoromethyl, allyl, ethynyl, propargyl, cyclopropyl, cyano, —C(=O)R$^{18}$, —C(=O)OR$^{18}$, —C(=O)NR$^{18}$R$^{19}$, —CR$^{18}$=NOR$^{19}$, —CR$^{18}$=N—NR$^{19}$R$^{20}$, —OR$^{18}$, —OSiR$^{18}$R$^{19}$R$^{20}$, —OC(=O)R$^{18}$, —OC(=O)OR$^{18}$, —OC(=O)NR$^{18}$R$^{19}$, —NR$^{18}$R$^{19}$, —N(R$^{18}$)C(=O)R$^{19}$, —N(R$^{18}$)C(=O)OR$^{19}$, —N(R$^{18}$)C(=O)NR$^{19}$R$^{20}$, —N(R$^{18}$)C(=S)R$^{19}$, —N(R$^{18}$)C(=S)NR$^{19}$R$^{20}$, —N=CR$^{18}$R$^{19}$, —N=C—NR$^{18}$R$^{19}$, —N(R$^{18}$)S(=O)$_2$R$^{19}$, —N(R$^{18}$)S(=O)$_2$OR$^{19}$, —N(R$^{18}$)S(=O)$_2$NR$^{19}$R$^{20}$, —SR$^{18}$, —S(=O)R$^{18}$, —S(=O)$_2$OR$^{18}$, —S(=O)$_2$NR$^{18}$R$^{19}$ and —SiR$^{18}$R$^{19}$R$^{20}$; wherein R$^{18}$, R$^{19}$ and R$^{20}$ are independently selected in the list consisting of hydrogen, methyl and trifluoromethyl.

The above mentioned preferences with regard to the substituents of the compounds of formula (I) and (Ia) to (Id) according to the invention can be combined in various manners. These combinations of preferred features thus provide sub-classes of compounds according to the invention. Examples of such sub-classes of preferred compounds according to the invention can combine:

preferred features of A with preferred features of one or more of L$^1$, L$^2$, Q, E$^1$ and E$^2$;
preferred features of L$^1$ with preferred features of one or more of A, L$^2$, Q, E$^1$ and E$^2$;
preferred features of L$^2$ with preferred features of one or more of A, L$^1$, Q, E$^1$ and E$^2$;
preferred features of Q with preferred features of one or more of A, L$^1$, L$^2$, E$^1$ and E$^2$;
preferred features of E$^1$ with preferred features of one or more of A, L$^1$, L$^2$, Q and E$^2$;
preferred features of E$^2$ with preferred features of one or more of A, L$^1$, L$^2$, Q and E$^1$.

In these combinations of preferred features of the substituents of the compounds according to the invention, the said preferred features can also be selected among the more preferred features of each of A, Q, $L^1$, $L^2$, $E^1$ and $E^2$; so as to form most preferred subclasses of compounds according to the invention.

The preferred features of the other substituents of the compounds according to the invention can also be part of such sub-classes of preferred compounds according to the invention, notably the groups of substituents R, Z, K, G and X as well as the integers a, b, m, n, p and q.

The present invention also relates to a process for the preparation of compounds of formula (I), (Ia), (Ib), (Ic) and (Id). Thus, according to a further aspect of the present invention, there is a provided process P1 for the preparation of compounds of formula (I), (Ia), (Ib), (Ic) and (Id) as hereindefined, as illustrated by the following reaction schemes.

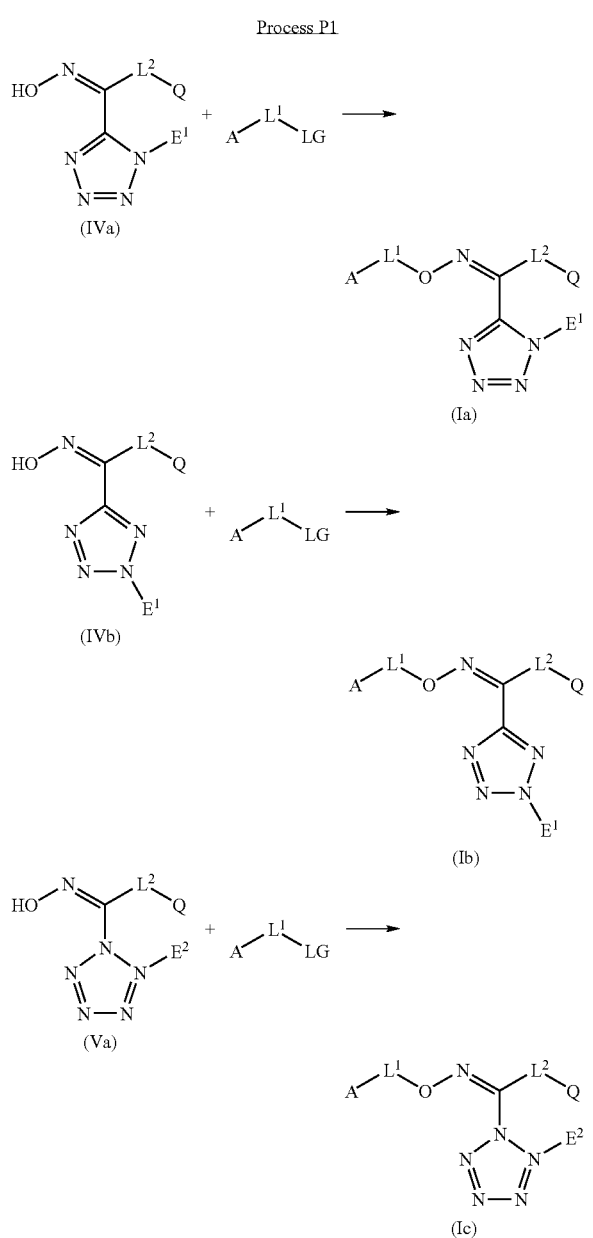

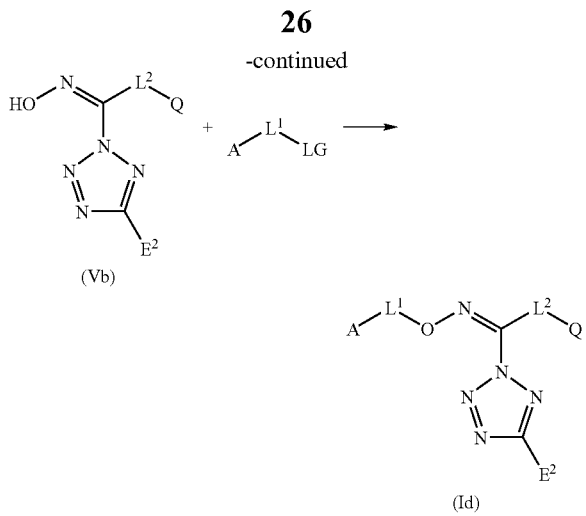

wherein

A, $L^1$, $L^2$, Q, $E^1$ and $E^2$ are as herein-defined and LG represents a leaving group. Suitable leaving groups can be selected in the list consisting of a halogen atom or other customary nucleofugal groups such as triflate, mesylate, or tosylate.

For the compounds of formula (I) according to the invention when $Z^1$, $Z^2$, $Z^3$, $Z^4$ $Z^5$, $Z^6$, $Z^7$, $Z^8$ or $Z^9$ represents an amino group, process P1 according to the invention can be completed by a further step comprising the additional modification of this group, notably by a reaction of acylation, alkoxycarbonylation, alkylaminocarbonylation or alkylaminothiocarbonylation, according to known methods. In such a case there is provided a process P2 according to the invention and such a process P2 can be illustrated by the following reaction schemes:

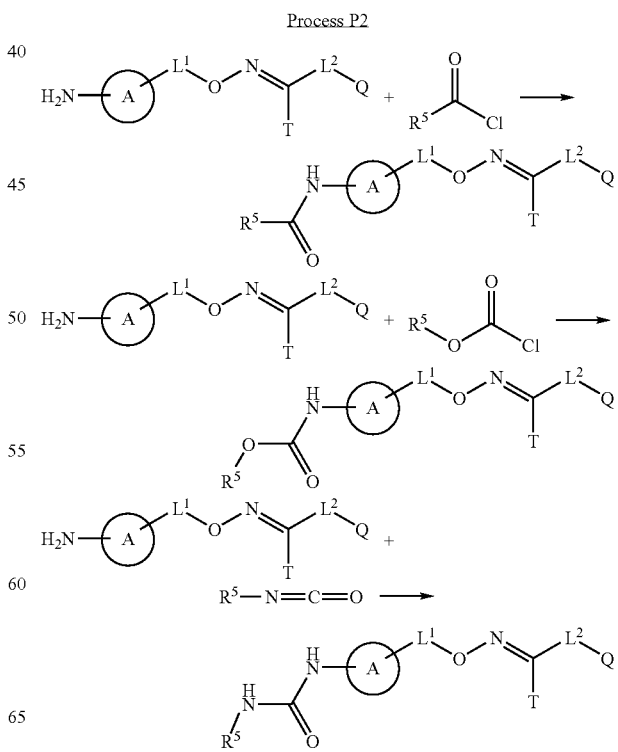

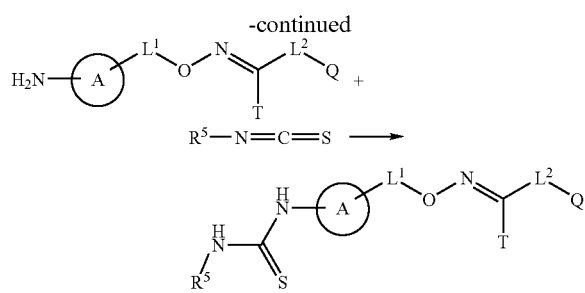

wherein A, $L^1$, $L^2$, T, Q and $R^5$ are as herein-defined.

If $Z^1$, $Z^2$, $Z^3$, $Z^4$, $Z^5$, $Z^6$, $Z^7$, $Z^8$ or $Z^9$ represents a protected amino group, carrying out process P2 would previously require a deprotection step in order to yield the amino group. Amino-protecting groups and related methods of cleavage thereof are known and can be found in T. W. Greene and P. G. M. Wuts, *Protective Group in Organic Chemistry*, $3^{rd}$ ed., John Wiley & Sons.

According to the invention, processes P1 and P2 may be performed if appropriate in the presence of a solvent and if appropriate in the presence of a base.

Suitable solvents for carrying out processes P1 and P2 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Suitable bases for carrying out processes P1 and P2 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diaza-bicyclo[5.4.0]undec-7-ene (DBU).

When carrying out processes P1 and P2 according to the invention, the reaction temperature can independently be varied within a relatively wide range. Generally, process P1 according to the invention is carried out at temperatures between 0° C. and 160° C.

Processes P1 and P2 according to the invention are generally independently carried out under atmospheric pressure. However, it is also possible to operate under elevated or reduced pressure.

When carrying out process P1 according to the invention, generally 1 mol or an excess of derivative of formula A-$L^1$-LG and from 1 to 3 mol of base are employed per mole of hydroximoyl tetrazoles of formula (IVa), (IVb), (Va) or (Vb). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that may still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

The compounds of formula (IVa) and (IVb), useful as a starting material, can be prepared, for example, by reacting hydroxylamine with the corresponding ketones that can be prepared, for example, according to the method described by R. Raap (*Can. J. Chem.* 1971, 49, 2139) by addition of a tetrazolyl lithium species to esters of formula Q-$L^2$-$CO_2$Me or Q-$L^2$-$CO_2$Et, or any of their suitable synthetic equivalents like, for example: Q-$L^2$-C(=O)—N(OMe)Me, Q-$L^2$-CN, Q-$L^2$-C(=O)Cl.

The compounds of general formula (Va) and (Vb), useful as a starting material, can be prepared, for example, from oximes of formula Q-$L^2$-CH=N—OH and 5-substituted tetrazoles according to the method described by J. Plenkiewicz et al. (*Bull. Soc. Chim. Belg.* 1987, 96, 675).

In a further aspect, the present invention also relates to a fungicide composition comprising an effective and non-phytotoxic amount of an active compound of formula (I) or (Ia) to (Id).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) or (Ia) to (Id) as herein defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous.

Examples of suitable fungicide mixing partners may be selected in the following lists B1) a compound capable to inhibit the nucleic acid synthesis like benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;

B2) a compound capable to inhibit the mitosis and cell division like benomyl, carbendazim, diethofencarb, ethaboxam, fuberidazole, pencycuron, thiabendazole, thiophanate-methyl, zoxamide;

B3) a compound capable to inhibit the respiration for example as CI-respiration inhibitor like diflumetorim;
as CII-respiration inhibitor like boscalid, carboxin, fenfuram, flutolanil, furametpyr, furmecyclox, mepronil, oxycarboxin, penthiopyrad, thifluzamide;
as CIII-respiration inhibitor like amisulbrom, azoxystrobin, cyazofamid, dimoxystrobin, enestrobin, famoxadone, fenamidone, fluoxastrobin, kresoximmethyl, metominostrobin, orysastrobin, picoxystrobin, pyraclostrobin, trifloxystrobin;

B4) a compound capable of to act as an uncoupler like dinocap, fluazinam, meptyldinocap;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

B9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

B10) a compound capable to inhibit cell wall synthesis like benthiavalicarb, dimethomorph, flumorph, iprovalicarb, mandipropamid, polyoxins, polyoxorim, validamycin A;

B11) a compound capable to inhibit melanine biosynthesis like carpropamid, diclocymet, fenoxanil, phthalide, pyroquilon, tricyclazole;

B12) a compound capable to induce a host defence like acibenzolar-S-methyl, probenazole, tiadinil;

B13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations including calcium polysulphide, thiram, tolylfluanid, zineb, ziram;

B14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy) methyl]phenyl}-2-(methoxyimino)-N- methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3-(difluoromethyl)-1-methyl-N-[2-(1,1,2,2-tetrafluoroethoxy)phenyl]-1H-pyrazole-4-carboxamide, 3-(difluoromethyl)-N-[(9R)-9-isopropyl-1,2,3,4-tetrahydro-1,4-methanonaphthalen-5-yl]-1-methyl-1H-pyrazole-4-carboxamide, 3-(difluoromethyl)N-[(9S-9-isopropyl-1,2,3,4-tetrahydro-1,4-methanonaphthalen-5-yl]-1-methyl-1H-pyrazole-4-carboxamide, 3-(difluoromethyl)N-[4'-(3,3-dimethylbut-1-yn-1-yl)biphenyl-2-yl]-1-methyl-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-chloro-7-(4-methylpiperidin-1-yl-(6-(2,4,6-trifluorophenyl)[1,2,4]triazolo[1,5-a]pyrimidine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(1,3-dimethylbutyl)phenyl]-5-fluoro-1,3-dimethyl-1H-pyrazole-4-carboxamide, N-{(Z)-[(cyclopropylmethoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, o-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, S-allyl-5-amino-2-isopropyl-4-(2-methylphenyl)-3-oxo-2,3-dihydro-1H-pyrazole-1-carbothioate, tecloftalam, tecnazene, triazoxide, trichlamide, valiphenal, zarilamid.

The composition according to the invention comprising a mixture of a compound of formula (I) or (Ia) to (Id) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) or (Ia) to (Id) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or (Ia) to (Id) or a fungicide composition according to the invention is applied to the seed, the plant or to the fruit of the plant or to the soil wherein the plant is growing or wherein it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the invention, mention may be made of:

Powdery mildew diseases such as:

*Blumeria* diseases, caused for example by *Blumeria graminis;*

*Podosphaera* diseases, caused for example by *Podosphaera leucotricha;*

*Sphaerotheca* diseases, caused for example by *Sphaerotheca fuliginea;*

*Uncinula* diseases, caused for example by *Uncinula necator;*

Rust diseases such as:
Gymnosporangium diseases, caused for example by *Gymnosporangium sabinae*;
Hemileia diseases, caused for example by *Hemileia vastatrix*;
Phakopsora diseases, caused for example by *Phakopsora pachyrhizi* or *Phakopsora meibomiae*;
Puccinia diseases, caused for example by *Puccinia recondita*;
Uromyces diseases, caused for example by *Uromyces appendiculatus*;
Oomycete diseases such as:
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;
Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporium cucumerinum*;
Cochliobolus diseases, caused for example by *Cochliobolus sativus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*; Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola Mycosphaerella arachidicola*; *Mycosphaerella fijiensis*;
Phaeosphaeria diseases, caused for example by *Phaeosphaeria nodorum*;
Pyrenophora diseases, caused for example by *Pyrenophora teres*;
Ramularia diseases, caused for example by *Ramularia collo-cygni*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incarnata*;
Venturia diseases, caused for example by *Venturia inaequalis*;

Root and stem diseases such as:
Corticium diseases, caused for example by *Corticium graminearum*;
Fusarium diseases, caused for example by *Fusarium oxysporum*;
Gaeumannomyces diseases, caused for example by *Gaeumannomyces graminis*;
Rhizoctonia diseases, caused for example by *Rhizoctonia solani*;
Tapesia diseases, caused for example by *Tapesia acuformis*;
Thielaviopsis diseases, caused for example by *Thielaviopsis basicola*;
Ear and panicle diseases such as:
Alternaria diseases, caused for example by *Alternaria* spp.;
Aspergillus diseases, caused for example by *Aspergillus flavus*;
Cladosporium diseases, caused for example by *Cladosporium* spp.
Claviceps diseases, caused for example by *Claviceps purpurea*;
Fusarium diseases, caused for example by *Fusarium culmorum*;
Gibberella diseases, caused for example by *Gibberella zeae*;
Monographella diseases, caused for example by *Monographella nivalis*;
Smut and bunt diseases such as:
Sphacelotheca diseases, caused for example by *Sphacelotheca reiliana*;
Tilletia diseases, caused for example by *Tilletia caries*;
Urocystis diseases, caused for example by *Urocystis occulta*;
Ustilago diseases, caused for example by *Ustilago nuda*;
Fruit rot and mould diseases such as:
Aspergillus diseases, caused for example by *Aspergillus flavus*;
Botrytis diseases, caused for example by *Botrytis cinerea*;
Penicillium diseases, caused for example by *Penicillium expansum*;
Sclerotinia diseases, caused for example by *Sclerotinia sclerotiorum*;
Verticilium diseases, caused for example by *Verticilium alboatrum*;
Seed and soilborne decay, mould, wilt, rot and damping-off diseases such as:
Fusarium diseases, caused for example by *Fusarium culmorum*;
Phytophthora diseases, caused for example by *Phytophthora cactorum*;
Pythium diseases, caused for example by *Pythium ultimum*;
Rhizoctonia diseases, caused for example by *Rhizoctonia solani*;
Sclerotium diseases, caused for example by *Sclerotium rolfsii*;
Microdochium diseases, caused for example by *Microdochium nivale*;
Canker, broom and dieback diseases such as:
Nectria diseases, caused for example by *Nectria galligena*;
Blight diseases such as:
Monilinia diseases, caused for example by *Monilinia laxa*;
Leaf blister or leaf curl diseases such as:
Taphrina diseases, caused for example by *Taphrina deformans*;

Decline diseases of wooden plants such as:
*Esca* diseases, caused for example by *Phaemoniella clamydospora*;
*Eutypa* dyeback, caused for example by *Eutypa lata*;
Dutch elm disease, caused for example by *Ceratocystsc ulmi*;
Diseases of flowers and Seeds such as:
*Botrytis* diseases, caused for example by *Botrytis cinerea*;
Diseases of tubers such as:
*Rhizoctonia* diseases, caused for example by *Rhizoctonia solani*.

The fungicide composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The following tables I-II illustrate in a non-limiting manner examples of compounds according to the invention.

In the following compound examples, M+H indicates the mass versus charge (m/z value) of the monoprotonated molecular ion, as observed in mass spectroscopy by positive atmospheric-pressure chemical-ionisation (APCI+) or positive electrospray-ionisation (ES+).

In the following examples, the logP values were determined in accordance with EEC Directive 79/831 Annex V.A8 by HPLC (High Performance Liquid Chromatography) on a reversed-phase column (C 18), using the method described below:

Temperature: 40° C. Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

TABLE I (Ic)

| N° | A | -L$^1$- | -L$^2$-Q | E$^2$ | LogP | M + H |
|---|---|---|---|---|---|---|
| 1 | | —CH$_2$— | | Me | 0.83 | 317 |
| 2 | | —CH$_2$— | | Me | 2.07 | 387 |

TABLE I-continued (Ic)

| N° | A | -L¹- | -L²-Q | E² | LogP | M + H |
|---|---|---|---|---|---|---|
| 3 | thiazole-NH-C(=O)-C(=CH₂)-CH₃ | —CH₂— | 2-pyridyl | Me | 2.06 | 385 |
| 4 | pentyl-C(=O)-NH-thiazole | —CH₂— | 2-pyridyl | Me | 2.7 | 415 |
| 5 | phenyl-C(=O)-NH-thiazole | —CH₂— | 2-pyridyl | Me | 2.48 | 421 |
| 6 | 4-amino-furazan-3-yl | —CH₂— | 2-pyridyl | Me | 1.52 | 302 |
| 7 | 2-methylthiazol-4-yl | —CH₂— | 2-pyridyl | Me | 1.76 | 316 |
| 8 | 5-(3-trifluoromethylphenyl)-1,2,4-oxadiazol-3-yl | —CH₂— | 2-pyridyl | Me | 3.32 | 431 |
| 9 | 6-aminopyridin-2-yl | —CH₂— | 2-pyridyl | Me | 0.76 | 311 |
| 10 | 5-phenyl-1,2,4-oxadiazol-3-yl | —CH₂— | 2-pyridyl | Me | 2.88 | 363 |

TABLE I-continued (Ic)

| N° | A | -L¹- | -L²-Q | E² | LogP | M + H |
|---|---|---|---|---|---|---|
| 11 | 5-(furan-2-yl)-1,2,4-oxadiazol-3-yl | —CH₂— | pyridin-2-yl | Me | 2.38 | 353 |
| 12 | 5-(4-tert-butylphenyl)-1,2,4-oxadiazol-3-yl | —CH₂— | pyridin-2-yl | Me | 4.19 | 419 |
| 13 | 5-(4-trifluoromethylphenyl)-1,2,4-oxadiazol-3-yl | —CH₂— | pyridin-2-yl | Me | 3.49 | 431 |
| 14 | 2-(cyclopropanecarboxamido)thiazol-4-yl | —CH₂— | pyridin-2-yl | Me | 1.99 | 385 |
| 15 | 2-(3-benzylureido)thiazol-4-yl | —CH₂— | pyridin-2-yl | Me | 2.15 | 450 |
| 16 | 2-(3-(2-(2,4-dichlorophenyl)ethyl)ureido)thiazol-4-yl | —CH₂— | pyridin-2-yl | Me | 2.95 | 532 |
| 17 | 2-(3-(2-(3,4-dichlorophenyl)ethyl)ureido)thiazol-4-yl | —CH₂— | pyridin-2-yl | Me | 3.08 | 532 |
| 18 | 2-(3-phenethylureido)thiazol-4-yl | —CH₂— | pyridin-2-yl | Me | 2.48 | 464 |

TABLE I-continued $$\underset{\underset{N=N}{\overset{N-N}{\parallel}}}{A-L^1-O-N=\overset{L^2-Q}{\underset{E^2}{\big|}}} \quad \text{(Ic)}$$

| N° | A | -L¹- | -L²-Q | E² | LogP | M + H |
|---|---|---|---|---|---|---|
| 19 | propyl-NH-C(O)-NH-thiazole | —CH₂— | 2-pyridyl | Me | 1.95 | 402 |
| 20 | 4-F-phenyl-ethyl-NH-C(O)-NH-thiazole | —CH₂— | 2-pyridyl | Me | 2.53 | 482 |
| 21 | 5-amino-1,2,4-thiadiazol-3-yl | —CH₂— | 2-pyridyl | Me | 1.3 | 318 |
| 22 | thiazole-NH-C(O)-NH-ethyl-(4-methoxyphenyl) | —CH₂— | 2-pyridyl | Me | 2.44 | 494 |
| 23 | 3-methoxybenzyl-NH-C(O)-NH-thiazole | —CH₂— | 2-pyridyl | Me | 2.32 | 480 |
| 24 | 3-Cl-phenyl-ethyl-NH-C(O)-NH-thiazole | —CH₂— | 2-pyridyl | Me | 2.79 | 498 |
| 25 | 2-methoxybenzyl-NH-C(O)-NH-thiazole | —CH₂— | 2-pyridyl | Me | 2.42 | 480 |
| 26 | cyclopropyl-NH-C(O)-NH-thiazole | —CH₂— | 2-pyridyl | Me | 1.61 | 400 |

TABLE I-continued (Ic)

| N° | A | -L¹- | -L²-Q | E² | LogP | M + H |
|---|---|---|---|---|---|---|
| 27 | pentyl-NH-C(O)-NH-thiazol-4-yl | —CH₂— | pyridin-2-yl | Me | 2.5 | 430 |
| 28 | tert-butyl-NH-C(O)-NH-thiazol-4-yl | —CH₂— | pyridin-2-yl | Me | 2.16 | 416 |
| 29 | 4-methoxyphenyl-O-C(O)-NH-thiazol-4-yl | —CH₂— | pyridin-2-yl | Me | 2.57 | 467 |
| 30 | pentyl-O-C(O)-NH-thiazol-4-yl | —CH₂— | pyridin-2-yl | Me | 3.1 | 431 |
| 31 | tBu-C(O)-NH-thiazol-4-yl | —CH₂— | 6-chloropyridin-3-yl | Me | 2.9 | |
| 32 | cyclohexyl-C(O)-NH-thiazol-4-yl | —CH₂— | 6-chloropyridin-3-yl | Me | 3.16 | 461 |
| 33 | 4-amino-furazan-3-yl | —CH₂— | 6-chloropyridin-3-yl | Me | 1.88 | 336 |
| 34 | 2-aminothiazol-4-yl | —CH₂— | 6-chloropyridin-3-yl | Me | 1.27 | 351 |

TABLE I-continued

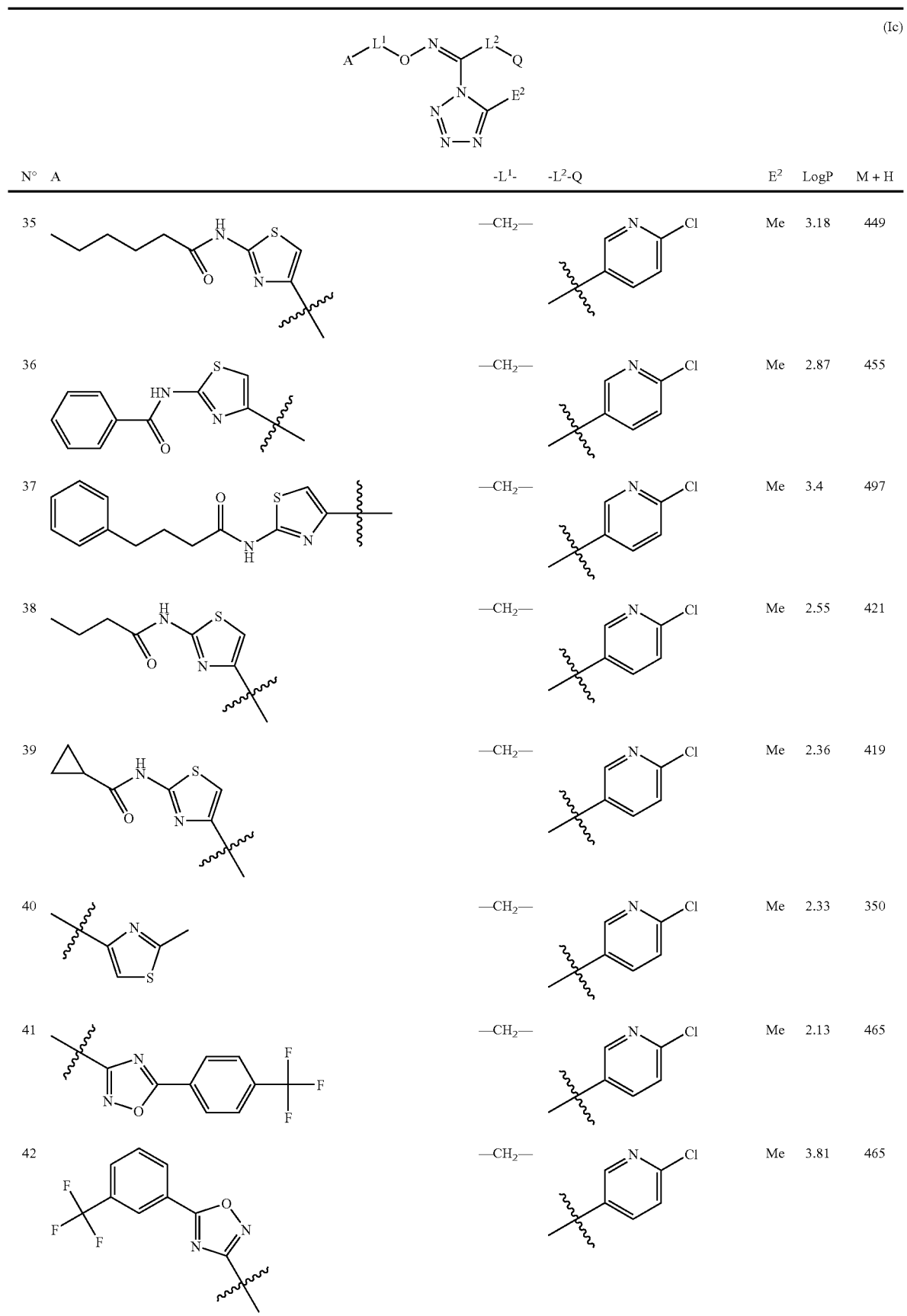

| N° | A | -L¹- | -L²-Q | E² | LogP | M + H |
|---|---|---|---|---|---|---|
| 35 | pentanoylamino-thiazolyl | —CH₂— | 6-chloropyridin-3-yl | Me | 3.18 | 449 |
| 36 | benzoylamino-thiazolyl | —CH₂— | 6-chloropyridin-3-yl | Me | 2.87 | 455 |
| 37 | 4-phenylbutanoylamino-thiazolyl | —CH₂— | 6-chloropyridin-3-yl | Me | 3.4 | 497 |
| 38 | butanoylamino-thiazolyl | —CH₂— | 6-chloropyridin-3-yl | Me | 2.55 | 421 |
| 39 | cyclopropanecarbonylamino-thiazolyl | —CH₂— | 6-chloropyridin-3-yl | Me | 2.36 | 419 |
| 40 | 2-methylthiazol-4-yl | —CH₂— | 6-chloropyridin-3-yl | Me | 2.33 | 350 |
| 41 | 5-(4-trifluoromethylphenyl)-1,2,4-oxadiazol-3-yl | —CH₂— | 6-chloropyridin-3-yl | Me | 2.13 | 465 |
| 42 | 5-(3-trifluoromethylphenyl)-1,2,4-oxadiazol-3-yl | —CH₂— | 6-chloropyridin-3-yl | Me | 3.81 | 465 |

TABLE I-continued
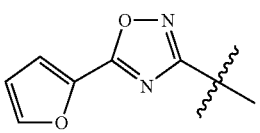
(Ic)
| N° | A | -L¹- | -L²-Q | E² | LogP | M + H |
|---|---|---|---|---|---|---|
| 43 | 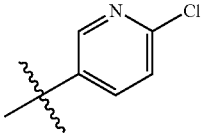 | —CH₂— | 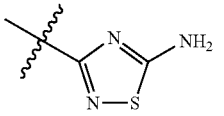 | Me | 2.68 | 387 |
| 44 | 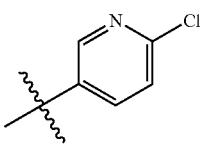 | —CH₂— | 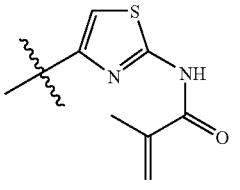 | Me | 1.78 | 352 |
| 45 | 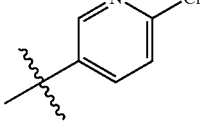 | —CH₂— | 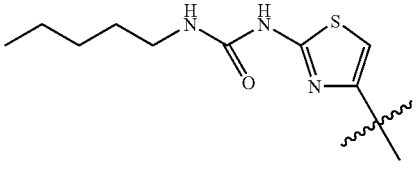 | Me | 2.55 | 419 |
| 46 | 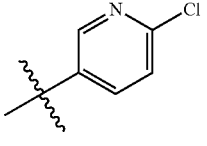 | —CH₂— | 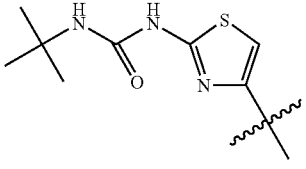 | Me | 2.91 | 464 |
| 47 | 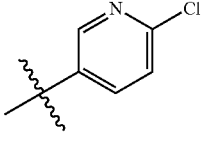 | —CH₂— | 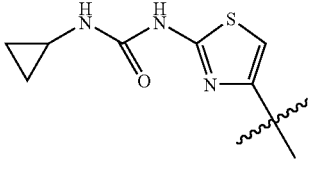 | Me | 2.65 | 450 |
| 48 | 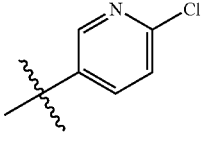 | —CH₂— | 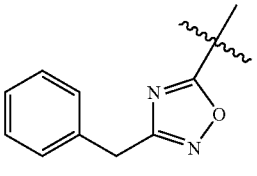 | Me | 1.98 | 434 |
| 49 | 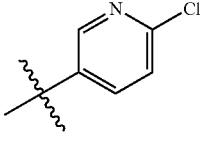 | —CH₂— | 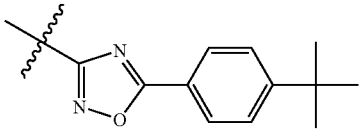 | Me | 3.09 | 411 |
| 50 | 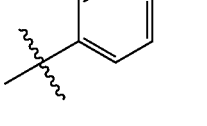 | —CH₂— | | Me | 4.47 | 453 |

TABLE I-continued (Ic)

| N° | A | -L¹- | -L²-Q | E² | LogP | M + H |
|---|---|---|---|---|---|---|
| 51 | 2-thienyl-thiazol-4-yl | —CH₂— | 6-chloropyridin-3-yl | Me | 3.27 | 418 |
| 52 | 4-(methoxycarbonyl)oxazol-2-yl | —CH₂— | 6-chloropyridin-3-yl | Me | 2.07 | 378 |
| 53 | 2-(4-fluorobenzamido)thiazol-4-yl | —CH₂— | 6-chloropyridin-3-yl | Me | 2.99 | 472 |
| 54 | 2-(4-chlorobenzamido)thiazol-4-yl | —CH₂— | 6-chloropyridin-3-yl | Me | 3.33 | 488 |
| 55 | 2-(4-tert-butylbenzamido)thiazol-4-yl | —CH₂— | 6-chloropyridin-3-yl | Me | 4.05 | 510 |
| 56 | 2-(3,3-dimethylbutanamido)thiazol-4-yl | —CH₂— | 6-chloropyridin-3-yl | Me | 3.19 | 448 |
| 57 | 2-(4-methoxybenzamido)thiazol-4-yl | —CH₂— | 6-chloropyridin-3-yl | Me | 2.97 | 484 |
| 58 | 2-(cyclopentanecarboxamido)thiazol-4-yl | —CH₂— | 6-chloropyridin-3-yl | Me | 2.97 | 446 |

TABLE I-continued (Ic)

| N° | A | -L¹- | -L²-Q | E² | LogP | M + H |
|---|---|---|---|---|---|---|
| 59 | thiazole with NHC(O)C(=CH₂)S-vinyl substituent | —CH₂— | 2-chloropyridin-5-yl | Me | 2.82 | 460 |
| 60 | 2-methylphenyl-C(O)NH-thiazole | —CH₂— | 2-chloropyridin-5-yl | Me | | 468 |
| 61 | 3-tert-butyl-1,2,4-oxadiazol-5-yl | —CH₂— | 2-chloropyridin-5-yl | Me | 3.07 | 377 |
| 62 | 3-(naphthalen-1-yl)-1,2,4-oxadiazol-5-yl | —CH₂— | 2-chloropyridin-5-yl | Me | 3.84 | 447 |
| 63 | 3-phenyl-1,2,4-oxadiazol-5-yl | —CH₂— | 2-chloropyridin-5-yl | Me | 3.21 | 397 |
| 64 | 5-(2-methoxyphenyl)-1,2,4-oxadiazol-3-yl | —CH₂— | 2-chloropyridin-5-yl | Me | 2.99 | 427 |
| 65 | 5-(4-methoxyphenyl)-1,2,4-oxadiazol-3-yl | —CH₂— | 2-chloropyridin-5-yl | Me | 3.22 | 427 |
| 66 | cyclopropyl-NH-C(=S)-NH-thiazole | —CH₂— | 2-chloropyridin-5-yl | Me | 2.68 | 450 |

TABLE I-continued
| N° | A | -L¹- | -L²-Q | E² | LogP | M+H |
|---|---|---|---|---|---|---|
| 67 | 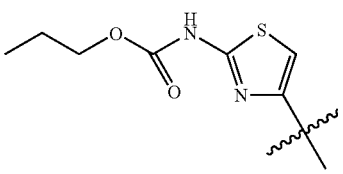 | —CH₂— | 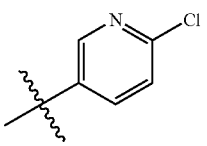 | Me | 2.83 | 436 |
| 68 | 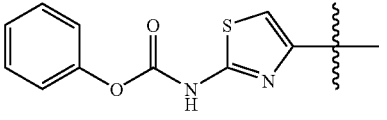 | —CH₂— | 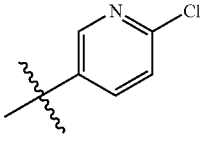 | Me | 2.98 | 470 |
| 69 | 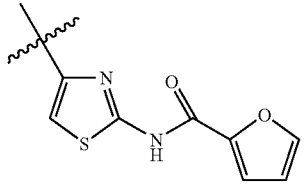 | —CH₂— | 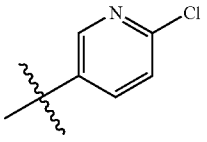 | Me | 2.46 | 444 |
| 70 | 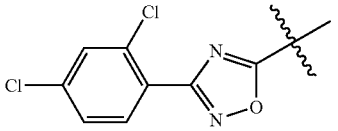 | —CH₂— | 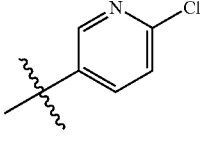 | Me | 3.94 | 466 |
| 71 | 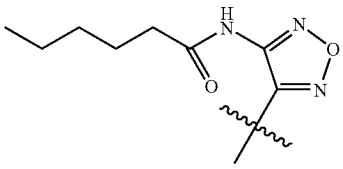 | —CH₂— | 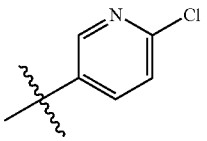 | Me | 3.25 | 434 |
| 72 | 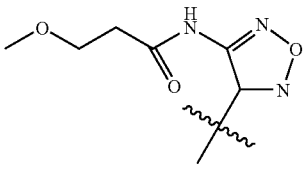 | —CH₂— | 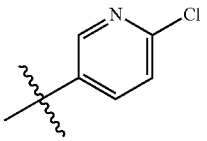 | Me | 2.17 | 422 |
| 73 | 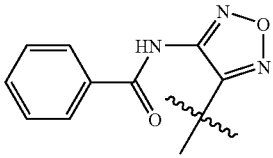 | —CH₂— | 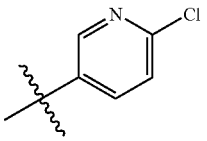 | Me | 2.84 | 440 |
| 74 | 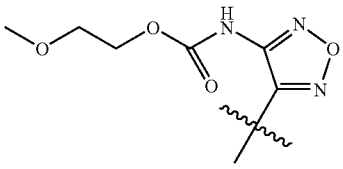 | —CH₂— | 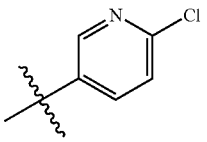 | Me | 2.3 | 438 |

TABLE I-continued
(Ic)
| N° | A | -L¹- | -L²-Q | E² | LogP | M + H |
|---|---|---|---|---|---|---|
| 75 | 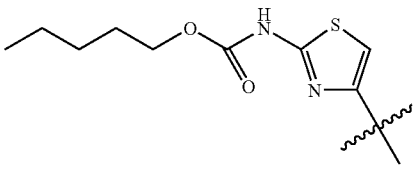 | —CH₂— | 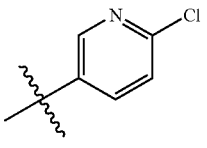 | Me | 3.78 | 465 |
| 76 | 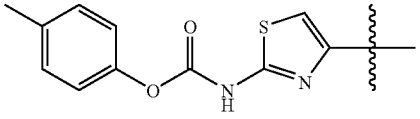 | —CH₂— | 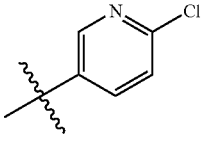 | Me | 3.48 | 485 |
| 77 | 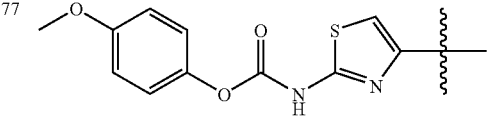 | —CH₂— | 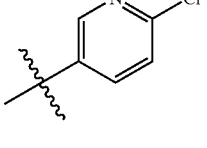 | Me | 3.17 | 501 |
| 78 | 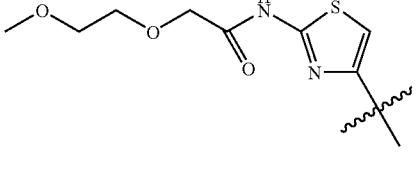 | —CH₂— | 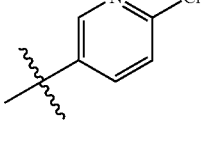 | Me | 2.4 | 467 |
| 79 | 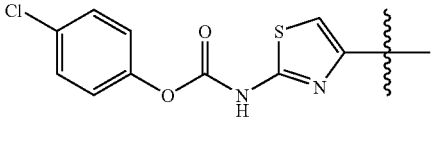 | —CH₂— | 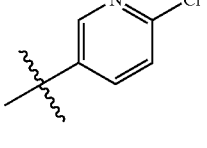 | Me | 3.62 | 505 |
| 80 | 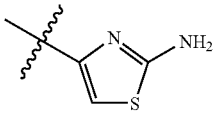 | —CH₂— | 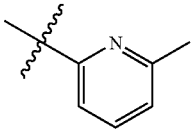 | Me | 1.2 | 331 |
| 81 | 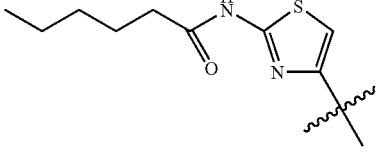 | —CH₂— | 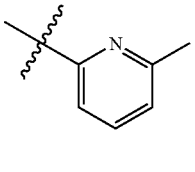 | Me | 3.03 | 429 |
| 82 | 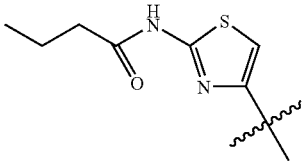 | —CH₂— | 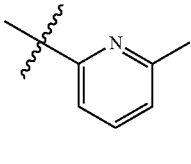 | Me | 2.38 | 401 |

TABLE I-continued (Ic)

| N° | A | -L¹- | -L²-Q | E² | LogP | M + H |
|---|---|---|---|---|---|---|
| 83 | phenyl-C(O)NH-thiazol-4-yl | | 6-methylpyridin-2-yl | Me | 2.78 | 435 |
| 84 | 4-amino-furazan-3-yl | —CH₂— | 6-methylpyridin-2-yl | Me | 1.94 | 316 |
| 85 | 2-methylthiazol-4-yl | —CH₂— | 6-methylpyridin-2-yl | Me | 2.13 | 330 |
| 86 | 5-(3-trifluoromethylphenyl)-1,2,4-oxadiazol-3-yl | —CH₂— | 6-methylpyridin-2-yl | Me | 3.67 | 445 |
| 87 | 6-aminopyridin-2-yl | | 6-methylpyridin-2-yl | Me | 1.18 | 325 |
| 88 | cyclopropyl-C(O)NH-thiazol-4-yl | —CH₂— | 6-methylpyridin-2-yl | Me | 2.28 | 399 |
| 89 | 5-[4-(trifluoromethyl)styryl]-1,2,4-oxadiazol-3-yl | —CH₂— | 6-methylpyridin-2-yl | Me | 3.72 | 445 |
| 90 | 6-(propanoylamino)pyridin-2-yl | —CH₂— | 6-methylpyridin-2-yl | Me | 2.7 | 395 |

TABLE I-continued (Ic)

| N° | A | -L¹- | -L²-Q | E² | LogP | M + H |
|---|---|---|---|---|---|---|
| 91 | cyclopropyl-C(O)-NH-pyridin-2,6-diyl | —CH₂— | pyridin-2,6-diyl | Me | 2.55 | 393 |
| 92 | n-pentanoyl-NH-pyridin-2,6-diyl | —CH₂— | pyridin-2,6-diyl | Me | 3.43 | 423 |
| 93 | 5-(4-tert-butylcyclohexenyl)-1,2,4-oxadiazol-3-yl | —CH₂— | pyridin-2,6-diyl | Me | 4.5 | 433 |
| 94 | 5-(furan-2-yl)-1,2,4-oxadiazol-3-yl | —CH₂— | pyridin-2,6-diyl | Me | 2.48 | 367 |
| 95 | 5-phenyl-1,2,4-oxadiazol-3-yl | —CH₂— | pyridin-2,6-diyl | Me | 3.11 | 377 |
| 96 | 5-amino-1,2,4-thiadiazol-3-yl | —CH₂— | pyridin-2,6-diyl | Me | 1.59 | 332 |
| 97 | 2-(methacryloylamino)thiazol-4-yl | —CH₂— | pyridin-2,6-diyl | Me | 2.4 | 399 |
| 98 | 4-(methoxycarbonyl)oxazol-2-yl | —CH₂— | pyridin-2,6-diyl | Me | 2.01 | 358 |

TABLE I-continued
(Ic)
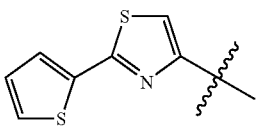
| N° | A | -L¹- | -L²-Q | E² | LogP | M + H |
|---|---|---|---|---|---|---|
| 99 | 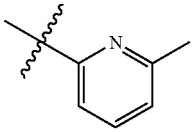 | —CH₂— | 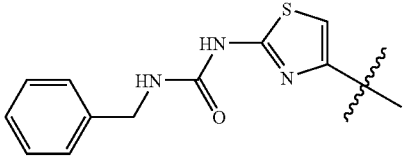 | Me | 3.14 | 398 |
| 100 | 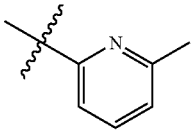 | —CH₂— | 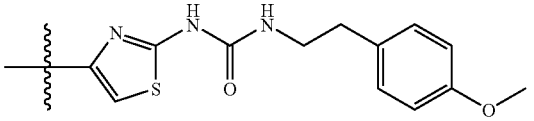 | Me | 2.55 | 464 |
| 101 | 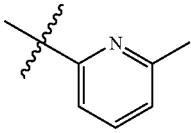 | —CH₂— | 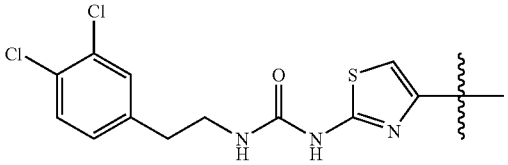 | Me | 2.67 | 508 |
| 102 | 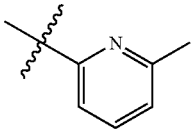 | —CH₂— | 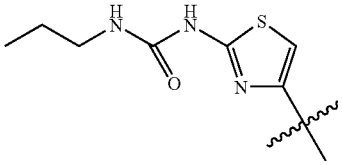 | Me | 3.34 | 547 |
| 103 | 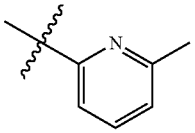 | —CH₂— | 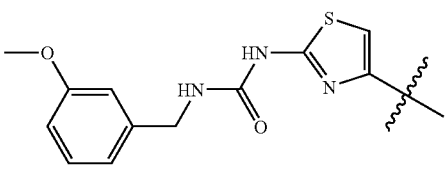 | Me | 2.17 | 416 |
| 104 | 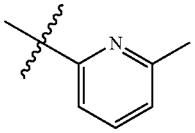 | —CH₂— | 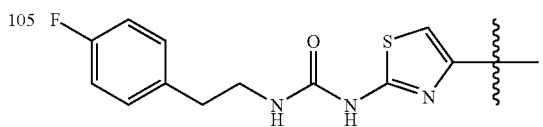 | Me | 2.59 | 494 |
| 105 | 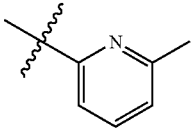 | —CH₂— | 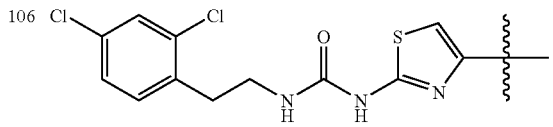 | Me | 2.78 | 496 |
| 106 | 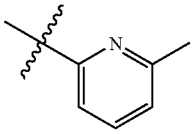 | —CH₂— | | Me | 3.43 | 546 |

TABLE I-continued
(Ic)
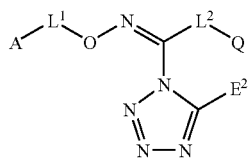
| N° | A | -L¹- | -L²-Q | E² | LogP | M + H |
|---|---|---|---|---|---|---|
| 107 | 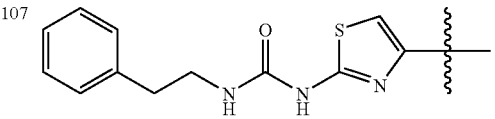 | —CH₂— | 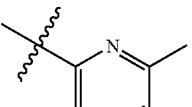 | Me | 2.72 | 478 |
| 108 | 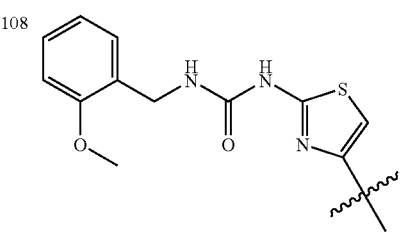 | —CH₂— | 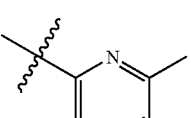 | Me | 2.69 | 494 |
| 109 | 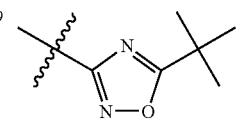 | —CH₂— | 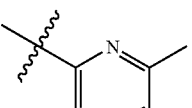 | Me | 2.89 | 357 |
| 110 | 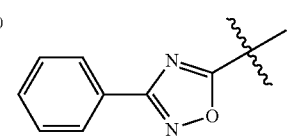 | —CH₂— | 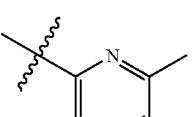 | Me | 3.08 | 377 |
| 111 | 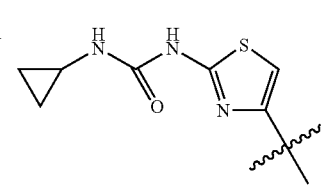 | —CH₂— | 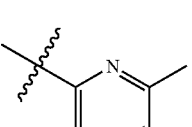 | Me | 1.89 | 414 |
| 112 | 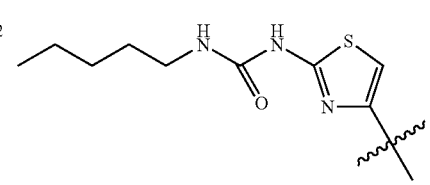 | —CH₂— | 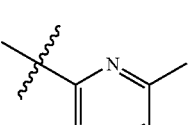 | Me | 2.76 | 444 |
| 113 | 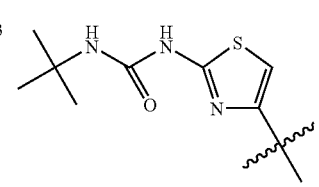 | —CH₂— | 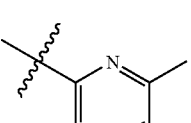 | Me | 2.53 | 430 |
| 114 | 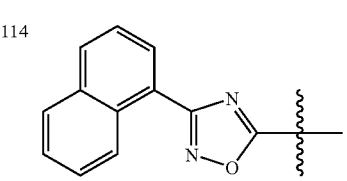 | —CH₂— | 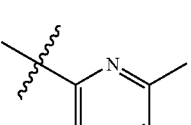 | Me | 3.73 | 427 |

TABLE I-continued (Ic)

| N° | A | -L¹- | -L²-Q | E² | LogP | M + H |
|---|---|---|---|---|---|---|
| 115 | 2,4-dichlorophenyl-1,2,4-oxadiazol-5-yl | | —CH₂— | pyridin-2,6-diyl | Me | 3.83 | 445 |
| 116 | 3-benzyl-1,2,4-oxadiazol-5-yl | | —CH₂— | pyridin-2,6-diyl | Me | 2.98 | 391 |
| 117 | 3-(2-methoxyphenyl)-1,2,4-oxadiazol-5-yl | | —CH₂— | pyridin-2,6-diyl | Me | 2.85 | 407 |
| 118 | 5-(4-methoxyphenyl)-1,2,4-oxadiazol-3-yl | | —CH₂— | pyridin-2,6-diyl | Me | 3.09 | 407 |
| 119 | 2-amino-5-bromothiazol-4-yl | | —CH₂— | pyridin-2,6-diyl | Me | 2.16 | 410 |
| 120 | 2-(phenoxycarbonylamino)thiazol-4-yl | | —CH₂— | pyridin-2,6-diyl | Me | 2.85 | 451 |
| 121 | 2-((4-methoxyphenoxy)carbonylamino)thiazol-4-yl | | —CH₂— | pyridin-2,6-diyl | Me | 2.84 | 481 |
| 122 | 2-(3-(2-(3-chlorophenyl)ethyl)ureido)thiazol-4-yl | | —CH₂— | pyridin-2,6-diyl | Me | 3.03 | 512 |

TABLE I-continued
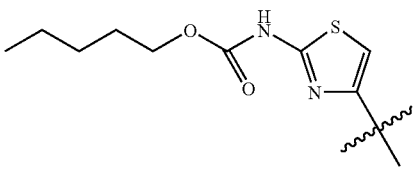
(Ic)
| N° | A | -L¹- | -L²-Q | E² | LogP | M + H |
|---|---|---|---|---|---|---|
| 123 |  | —CH₂— | 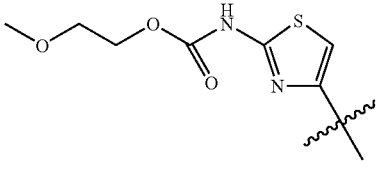 | Me | 3.41 | 445 |
| 124 |  | —CH₂— | 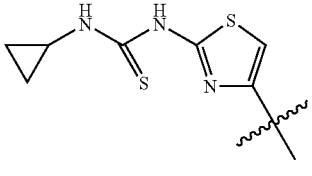 | Me | 2.11 | 433 |
| 125 |  | —CH₂— | 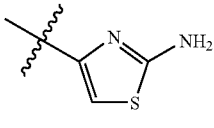 | Me | 2.56 | 430 |
| 126 |  | —CH₂— | 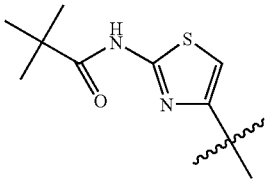 | Me | 1.72 | 385 |
| 127 |  | —CH₂— | 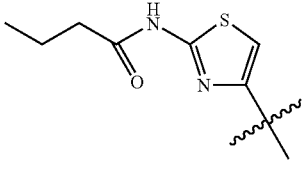 | Me | 3.3 | 469 |
| 128 |  | —CH₂— | 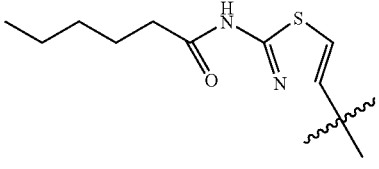 | Me | 2.94 | 455 |
| 129 |  | —CH₂— |  | Me | 3.6 | 483 |

TABLE I-continued
(Ic)
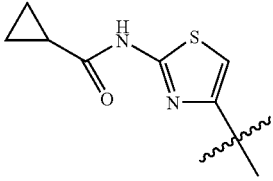
| N° | A | -L¹- | -L²-Q | E² | LogP | M + H |
|---|---|---|---|---|---|---|
| 130 | 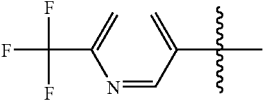 | —CH₂— | 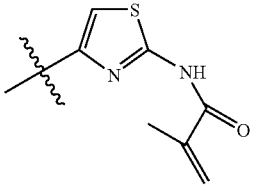 | Me | 2.76 | 453 |
| 131 | 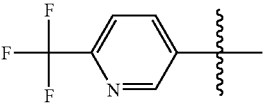 | —CH₂— | 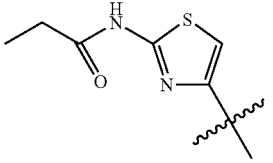 | Me | 2.06 | 453 |
| 132 | 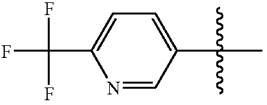 | —CH₂— | 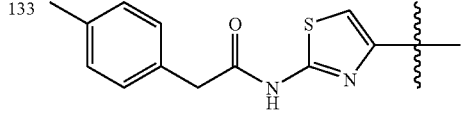 | Me | 2.78 | 441 |
| 133 | 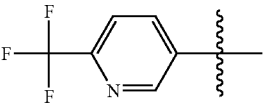 | —CH₂— | 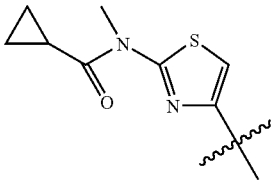 | Me | 3.5 | 517 |
| 134 | 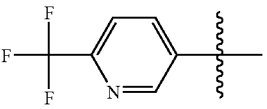 | —CH₂— | 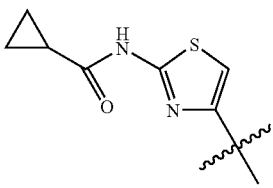 | Me | 2.89 | 453 |
| 135 | 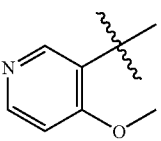 | —CH₂— | 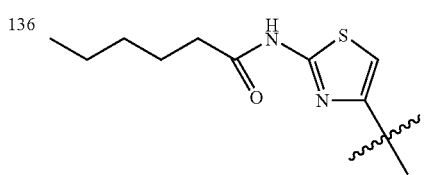 | Me | 2.51 | 415 |
| 136 | 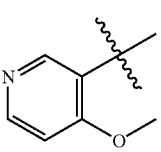 | —CH₂— | | Me | 3.44 | 445 |

TABLE I-continued (Ic)

| N° | A | -L¹- | -L²-Q | E² | LogP | M + H |
|---|---|---|---|---|---|---|
| 137 | phenyl–NH–C(O)–thiazolyl | —CH₂— | 4-methoxypyridin-3-yl | Me | 3.13 | 451 |
| 138 | MeO-CH₂CH₂-C(O)-NH-thiazolyl | —CH₂— | 4-methoxypyridin-3-yl | Me | 2.25 | 433 |
| 139 | phenyl-CH₂CH₂-C(O)-NH-thiazolyl | —CH₂— | 4-methoxypyridin-3-yl | Me | 3.31 | 479 |
| 140 | iPr-C(O)-NH-thiazolyl | —CH₂— | 4-methoxypyridin-3-yl | Me | 2.66 | 417 |
| 141 | iBu-C(O)-NH-thiazolyl | —CH₂— | 4-methoxypyridin-3-yl | Me | 2.96 | 431 |
| 142 | tBu-C(O)-NH-thiazolyl | —CH₂— | 4-methoxypyridin-3-yl | Me | 3.06 | 431 |
| 143 | 4-MeO-phenyl-O-C(O)-NH-thiazolyl | —CH₂— | 4-methoxypyridin-3-yl | Me | 3.14 | 497 |
| 144 | 4-Me-phenyl-O-C(O)-NH-thiazolyl | —CH₂— | 4-methoxypyridin-3-yl | Me | 3.46 | 481 |

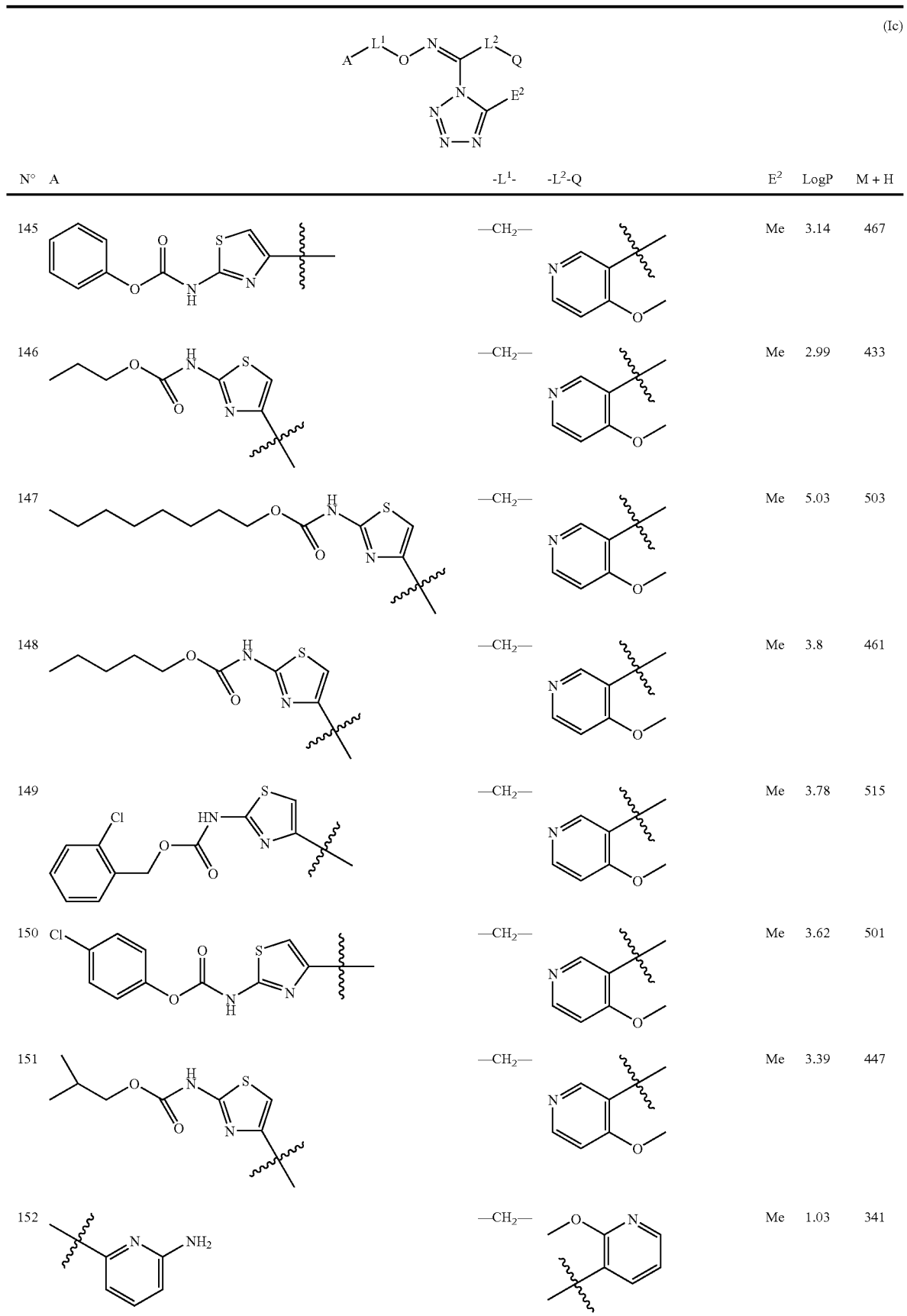

TABLE I-continued
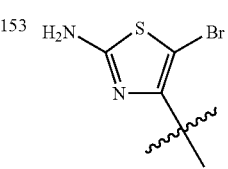
(Ic)
| N° | A | -L¹- | -L²-Q | E² | LogP | M + H |
|---|---|---|---|---|---|---|
| 153 |  | —CH₂— | 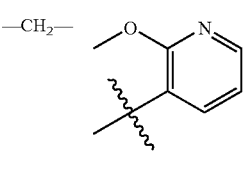 | Me | 2.27 | 427 |
| 154 | 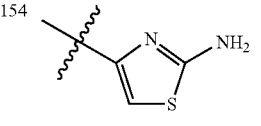 | —CH₂— |  | Me | 1.24 | 347 |
TABLE II
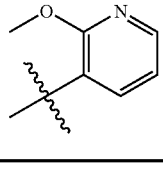
(Ia)
| N° | A | -L¹- | -L²-Q | E¹ | LogP | M + H |
|---|---|---|---|---|---|---|
| 155 | 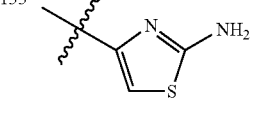 | —CH₂— |  | Me |  | 351 |
| 156 | 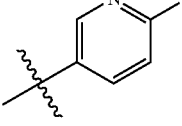 | —CH₂— | 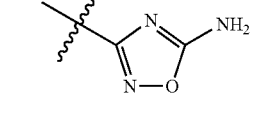 | Me |  | 336 |
| 157 |  | —CH₂— | 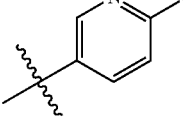 | Me | 1.04 | 331 |
| 158 | 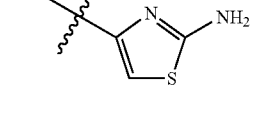 | —CH₂— |  | Me | 2.94 | 429 |

TABLE II-continued
(Ia)
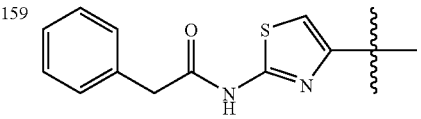
| N° | A | -L¹- | -L²-Q | E¹ | LogP | M + H |
|----|---|------|-------|----|----|-------|
| 159 |  | —CH₂— | 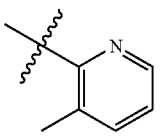 | Me | 2.62 | 449 |
| 160 | 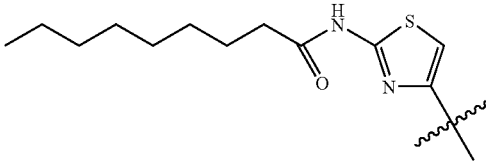 | —CH₂— |  | Me | 4.11 | 471 |
| 161 | 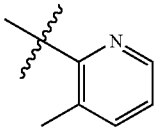 | —CH₂— | 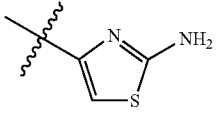 | Me |  | 347 |
| 162 |  | —CH₂— | 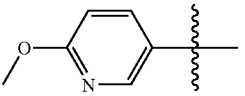 | Me |  | 445 |
| 163 | 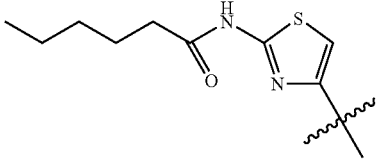 | —CH₂— |  | Me |  | 431 |
| 164 | 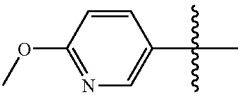 | —CH₂— | 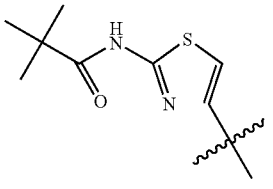 | Me |  | 415 |
| 165 |  | —CH₂— | 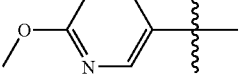 | Me |  | 417 |
| 166 | 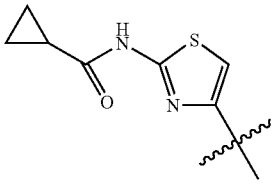 | —CH₂— |  | Me |  | 431 |

TABLE II-continued (Ia)

| N° | A | -L¹- | -L²-Q | E¹ | LogP | M + H |
|---|---|---|---|---|---|---|
| 167 | (oxadiazole-NH₂) | —CH₂— | (methoxypyridine) | Me | | 332 |
| 168 | (CF₃-C(O)-NH-C(S)-N=) | —CH₂— | (methoxypyridine) | Me | | 443 |

The following examples illustrate in a non-limiting manner the preparation of the compounds of formula (I) according to the invention.

(3-Methylpyridin-2-yl-(1-methyltetrazol-5-yl)methanone

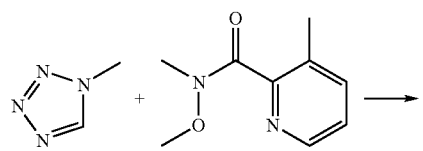

To a solution of 1-methyltetrazole (2.9 g, 34.7 mmol) and TMEDA (10 ml, 66.2 mmol) in THF (100 ml) cooled at −78° C. is added dropwise 2.5 M nBuLi in hexanes (13.9 ml, 34.7 mmol) with vigorous stirring and maintaining the reaction temperature below −65° C. On complete addition, the mixture is is stirred 20 minutes before adding dropwise a solution of N-methyl-N-methoxy-(3-methylpyridin-2-yl)carboxamide (6.3 g, 34.7 mmol) in THF. On complete addition, the mixture is stirred for six hours at −78° C. before adding slowly a half-diluted saturated aqueous NaHCO₃ solution (300 ml). The mixture is extracted with ethyl acetate (500 ml). After separation, the organic layer is dried (MgSO₄), filtered and concentrated. Silica-gel chromatography of the residue affords 2.8 g of (3-methylpyridin-2-yl)-(1-methyltetrazol-5-yl)methanone [yield 39.7%; ¹H-NMR (DMSO-d6) $\delta_{ppm}$: 2.6 (s, 3H), 4.17 (s, 3H), 7.65 (dd, 1H), 7.95 (d, 1H), 8.56 (d, 1H)].

1-Methyl-5-[(3-methylpyridin-2-yl)carbohydroximoyl]tetrazole

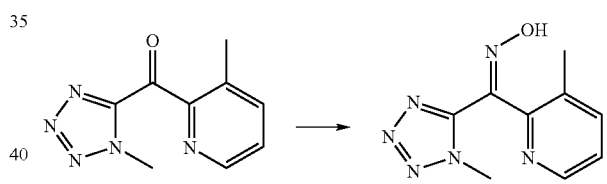

A solution of (3-methylpyridin-2-yl(1-methyltetrazol-5-yl)methanone (2.8 g, 13.8 mmol) and hydroxylamine hydrochloride (2.4 g, 34.4 mmol) in pyridine (30 ml) is stirred three hours at 50° C. and overnight at room temperature. The solvent is evaporated and water is added to the crude mixture. The resulting suspension is filtered. The solid is washed with water and dried to give 2.65 g of 1-methyl-5-[(3-methylpyridin-2-yl)carbohydroximoyl]tetrazole [yield 88.1%; ¹H-NMR (DMSO-d6) $\delta_{ppm}$: 2.6 (s, 3H), 4.02 (s, 3H), 7.35 (dd, 1H), 7.82 (d, 1H), 8.34 (d, 1H), 13.1 (s, 1H)].

O-(2-Amino-1,3-thiazol-4-yl)methyl-(3-methylpyridin-2-yl)-(1-methyltetrazol-5-yl)methanone Oxime (Compound 157)

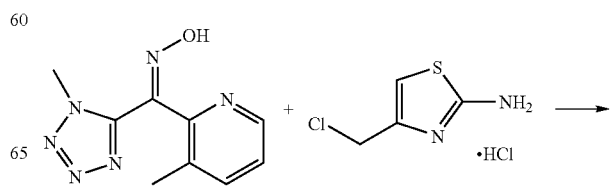

-continued

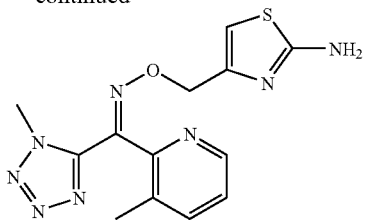

To a solution of 1-methyl-5-[(3-methylpyridin-2-yl)carbohydroximoyl]tetrazole (2.6 g, 11.9 mmol) in dichloromethane are added resin PL-TBD 1.81 mmol/g (13.2 g) and 4-chloromethyl-2-amino-1,3-thiazole hydrochloride (2.4 g, 13.1 mmol). The mixture is stirred for two days and filtered. The resin is washed successively with dichloromethane, methanol and dichloromethane. The combined filtrates are concentrated. Silica-gel chromatography of the residue affords 1.3 g of compound 157 [yield 33%; HPLC/MS: m/z=331 (M+H); LogP=1.04].

O-(2-Pentylcarbonylmino-1,3-thiazol-4-yl)methyl-(3-methylpyridin-2-yl)-(1-methyltetrazol-5-yl) methanone oxime (compound 158)

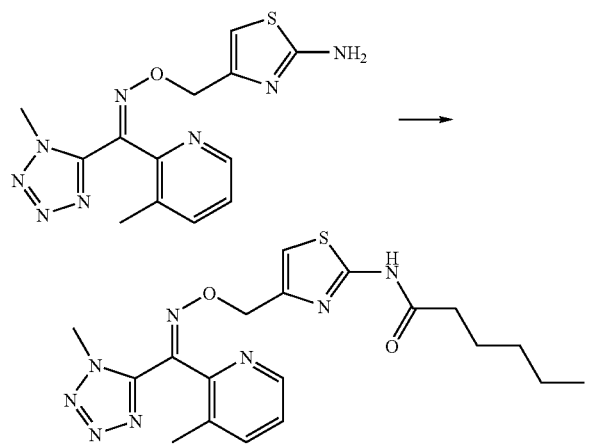

To a solution of compound 157 (0.2 g, 0.6 mmol) in dichloromethane (5 ml) are added resin PS-BEMP 2.2 mmol/g (0.55 g) and hexanoyl chloride (0.13 ml, 0.9 mmol). After stirring overnight, the reaction mixture is filtered. The resin is washed successively with dichloromethane, methanol and dichloromethane. The combined filtrates are concentrated. Silica-gel chromatography of the residue affords 0.08 g of compound 158 [yield 32.2%; HPLC/MS: m/z=429 (M+H); Log P=2.94].

5-Methyl-1-(6-chloropyridin-3-ylcarbohydroximoyl) tetrazole

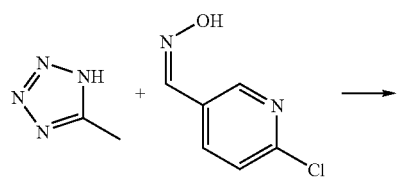

-continued

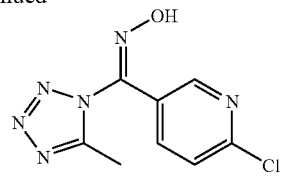

To a solution of 6-chloropyridin-3-yl-carboxaldehyde oxime (30 g, 191.6 mmol) in DMF (250 ml) is added N-chlorosuccinimide (26.8 g, 201.2 mmol) portionwise, while maintaining the reaction temperature below 45° C. On complete addition, the mixture is stirred 1.5 hour at room temperature before being poured into a saturated aqueous NH$_4$Cl solution. The mixture is extracted with ethyl acetate. The organic layer is washed successively with water and brine, dried (MgSO$_4$), filtered and concentrated. The residue and 5-methyltetrazole (16.1 g, 191.6 mmol) are diluted in dichloromethane (200 ml) and triethyamine (48.9 ml, 249 mmol) is added dropwise at room temperature. After stirring overnight, a saturated aqueous NH$_4$Cl solution and ethyl acetate are added. The resulting suspension is filtered. The solid is washed with water and dried to give 29.9 g of 5-methyl-[(6-chloropyridin-3-ylcarbohydroximoyl)-tetrazole [yield 62.1%; $^1$H-NMR (DMSO-d6) $\delta_{ppm}$: 2.52 (s, 3H), 7.64 (d, 1H), 7.92 (d, 1H), 8.5 (s, 1H), 13.4 (s, 1H)].

O-(2-tert-butylcarbonylamino-1,3-thiazol-4-yl)methyl-(6-chloropyridin-3-yl-(5-methyltetrazol-1-yl) methanone oxime (compound 31)

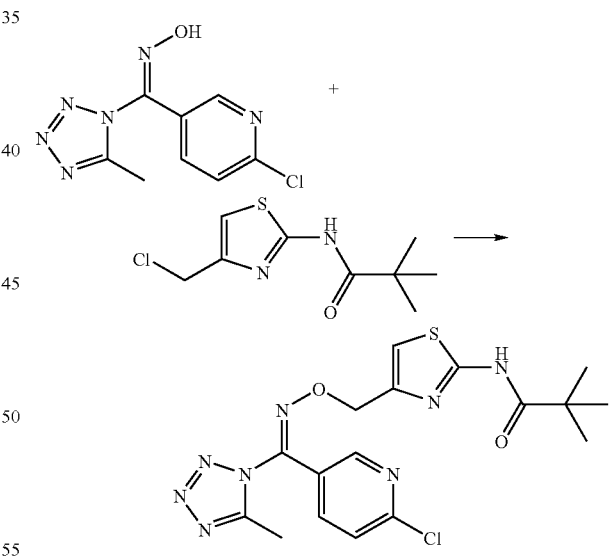

To a cooled solution (0-5° C.) of 5-methyl-1-(6-chloropyridin-3-ylcarbohydroximoyl)-tetrazole (15 g, 62.8 mmol) and 4-chloromethyl-2-tert-butylcarbonylamino-1,3-thiazole (14.6 g, 62.8 mmol) in acetonitrile (750 ml) is added DBN (15 ml, 125.7 mmol) diluted in acetronitrile (80 ml). On complete addition, the mixture is shirred 1.5 hour before the removal of the cooling bath. After stirring overnight, the mixture is filtrated over a short pad of silica-gel. The residue is washed with acetonitrile and the combined filtrates are concentrated. The residue is partitioned between dichloromethane (400 ml) and 5% aqueous solution KH$_2$PO$_4$ (150 ml). The organic layer is washed successively with 5% aqueous solution KH$_2$PO$_4$ (150 ml), water (300 ml) and 5% aqueous solution KH$_2$PO$_4$ (2×150 ml), then dried (MgSO$_4$), filtered and concentrated. The resulting brown gum is diluted with a small amount of dichloromethane (10 ml) and diethyl ether is added (350 ml). A white powder falls out. Filtration and drying affords 6 g of compound 31 [yield 21.9%; LogP=2.9].

5-Methyl-1-(6-methylpyridin-2-ylcarbohydroximoyl)-tetrazole and 5-methyl-2-(6-methylpyridin-2-ylcarbohydroximoyl)-tetrazole

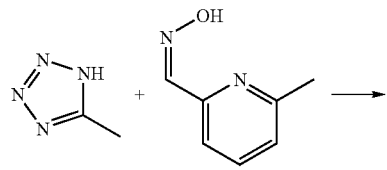

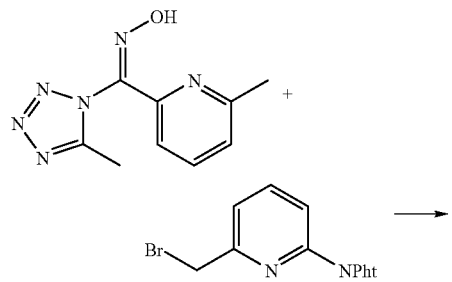

In the same manner as in preparation of 5-methyl-1-(6-chloropyridin-3-ylcarbohydroximoyl)-tetrazole, except that 6-methylpyridin-2-yl-carboxaldehyde oxime (14.9 g, 109.4 mmol) is used in place of 6-chloropyridin-3-yl-carboxaldehyde oxime as starting material, is obtained 10.7 g of 5-methyl-1-(6-methylpyridin-2-ylcarbohydroximoyl)tetrazole [yield 42.4%; $^1$H-NMR (DMSO-d6) $\delta_{ppm}$: 2.35 (s, 3H), 2.44 (s, 3H), 7.48 (dd, 1H), 7.86 (m, 2H), 13.25 (s, 1H)] and 1.34 g of and 5-methyl-2-(6-methylpyridin-2-ylcarbohydroximoyl)-tetrazole [yield 5.1%; $^1$H-NMR (DMSO-d6) $\delta_{ppm}$: 2.33 (s, 3H), 2.6 (s, 3H), 7.38 (d, 1H), 7.84 (m, 2H), 13.15 (s, 1H)].

O-(2-Phtalimidopyridin-6-yl)methyl-(6-methylpyridin-2-yl)-(5-methyltetrazol-1-yl)methanone oxime

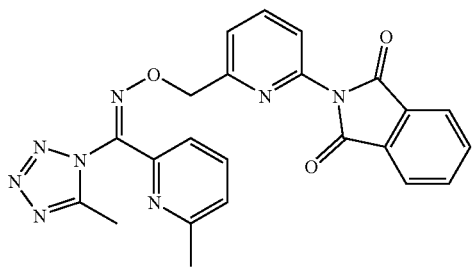

To a solution of 5-methyl-1-(6-methylpyridin-2-ylcarbohydroximoyl)-tetrazole (0.5 g, 2.3 mmol) in acetonitrile (25 ml) are added resin PL-TBD 1.81 mmol/g (3.8 g) and 6-bromomethyl-2-phtalimidopyridine (0.8 g, 2.5 mmol). After stirring overnight, the reaction mixture is filtered. The resin is washed with acetonitrile and the combined filtrates are concentrated. Silica-gel chromatography of the residue affords 1 g of O-(2-phtalimidopyridin-yl)methyl-(6-methylpyridin-2-yl)-(5-methyltetrazol-1-yl)methanone oxime [yield 82% LogP=2.57].

O-(2-Aminopyridin-6-yl)methyl-(6-methylpyridin-2-yl)-(5-methyltetrazol-1-yl)methanone oxime (compound 87)

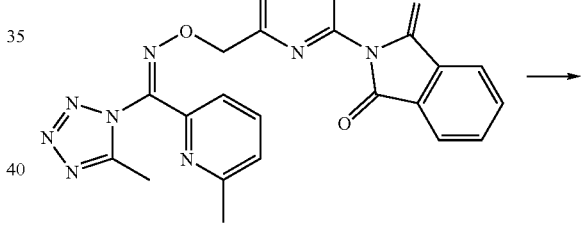

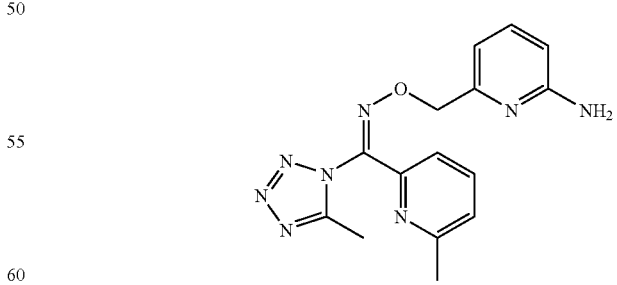

To a solution of compound O-(2-phtalimidopyridin-6-yl) methyl-(6-methylpyridin-2-yl)-(5-methyltetrazol-1-yl) methanone oxime (1.5 g, 3.3 mmol) in THF (150 ml) is added hydrazine hydrate (0.8 ml, 16.5 mmol). After stirring overnight, the reaction mixture is filtered and concentrated. Silica-gel chromatography of the residue affords 0.61 g of compound 87 [yield 49.6%; HPLC/MS: m/z=325 (M+H); LogP=1.18].

O-[2-(Pentylcarbonylamino)pyridin-6-yl]methyl-(6-methylpyridin-2-yl)-(5-methyltetrazol-1-yl)methanone Oxime (Compound 92)

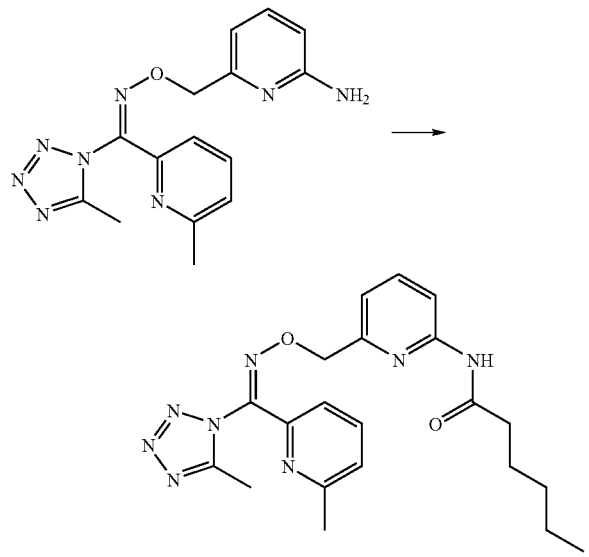

To a solution of compound 87 (0.12 g, 0.37 mmol) in dry dichloromethane (5 ml) are added triethylamine (0.06 ml, 0.41 mmol) and hexanoyl chloride (0.06 ml, 0.41 mmol). After stirring overnight, the reaction mixture is concentrated. Silica-gel chromatography of the residue affords 0.14 g of compound 92 [yield 86.3%; HPLC/MS (APCI): m/z=423 (M+H); LogP=3.43].

The following examples illustrate in a non-limiting manner the biological activity of the compounds of formula (I) according to the invention.

EXAMPLE A

In Vivo Test on *Peronospora parasitica*

Crucifer Downy Mildew

Cabbage plants (Eminence variety) in starter cups, sown on a 50/50 peat soil-pozzolana substrate and grown at 18-20° C., are treated at the cotyledon stage by spraying with the aqueous suspension described above. Plants, used as controls, are treated with an aqueous solution not containing the active material. After 24 hours, the plants are contaminated by spraying them with an aqueous suspension of *Peronospora parasitica* spores (50 000 spores per ml). The spores are collected from infected plant. The contaminated cabbage plants are incubated for 5 days at 20° C., under a humid atmosphere. Grading is carried out 5 days after the contamination, in comparison with the control plants.

Under these conditions, good protection (at least 70%) is observed at a dose of 500 ppm with the following compounds: 2, 3, 4, 5, 14, 18, 20, 27, 30, 31, 35, 39, 46, 58, 59, 60, 67, 75, 90, 91, 92, 107, 108, 113, 119, 130, 132, 158 and 159.

EXAMPLE B

In Vivo Test on *Phytophthora infestans*

Tomato Late Blight

Tomato plants (Marmande variety) sown in started cups on a 50/50 peat soil-pozzolana subtrate and grown at 20-25° C., are treated at stage Z16 by spraying with the aqueous suspension described above. Plants, used as controls, are treated with an aqueous solution not containing the active material. After 24 hours, the plants are contaminated by spraying them with an aqueous suspension of *Phytophthora infestans* spores (20 000 spores per ml). The spores are collected from infected plants. The contaminated tomato plants are incubated for 5 days at 20° C., under a humid atmosphere. Grading is carried out 5 days after the contamination, in comparison with the control plants.

Under these conditions, good protection (at least 70%) is observed at a dose of 500 ppm with the following compounds: 31 and 92.

EXAMPLE C

In Vivo Test on *Plasmopara parasitica*

Vine Downy Mildew

Vine plants (Cabernet variety) grown on a 50/50 peat soil-pozzolana subtrate at 20-22° C., are treated at stage Z15 by spraying with the aqueous suspension described above. Plants, used as controls, are treated with an aqueous solution not containing the active material. After 24 hours, the plants are contaminated by spraying the lower surface of the leaves with an aqueous suspension of *Plasmopara viticola* spores (100 000 spores per ml). The spores are collected from infected plants. The contaminated vine plants are incubated for 7 to 8 days at 20° C., under humid atmosphere. Grading is carried out 7 to 8 days after the contamination, in comparison with the control plants.

Under these conditions, good protection (at least 70%) is observed at a dose of 500 ppm with the following compounds: 27, 30, 31, 35, 39, 46, 60, 92, 112 and 113.

EXAMPLE D

Cell Test on *Pythium ultimum*

Damping-Off

The growth of *Pythium ultimum* is performed in PDB medium at 20° C. during 7 days. The PDB medium is prepared by mixing 24 grams of PDB (Difco) in 1 liter of demineralized water. The medium is sterilized by autoclave 15 minutes at 121° C. After 7 days of growth, the mycelium of *Pythium ultimum* is ground and is used as inoculum. The compounds are solubilized in DMSO and added to sterile liquid glucose/mycopeptone medium (14.6 g/l of D-glucose, 7.1 g/l of mycological peptone (Oxoid) and 1.4 g/l of yeast extract (Merck)) at a concentration of 2 ppm. The medium is inoculated with the ground mycelium at an initial OD at 620 nm of 0.025. The efficacy of the compounds is assessed by OD measurement at 620 nm after 5 days at 20° C. in comparison with a control.

Under these conditions, good protection (at least 70%) is observed at a dose of 6 ppm with the following compounds: 3, 4, 5, 16, 17, 18, 20, 22, 23, 24, 25, 27, 28, 30, 31, 32, 35, 36, 37, 39, 41, 46, 47, 51, 53, 54, 55, 57, 58, 59, 60, 65, 67, 68, 75, 76, 92, 97, 108, 123, 137, 142, 158 and 160.

The invention claimed is:
1. A compound of formula (I)

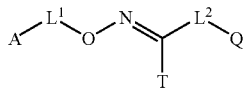
(I)

wherein

T is a substituted or non-substituted tetrazolyl group;

$L^1$ is a direct bond or a divalent group selected from the group consisting of

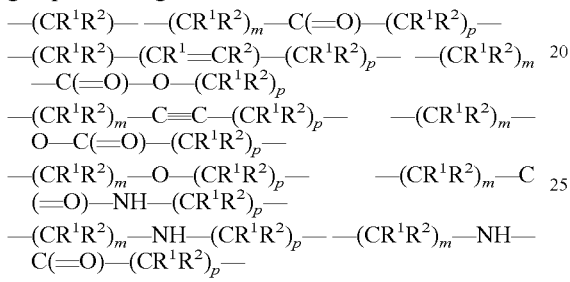

wherein
  n is 1, 2, 3 or 4;
  m and p are independently 0, 1, 2 or 3;

$L^2$ is a direct bond or a divalent group selected from the group consisting of

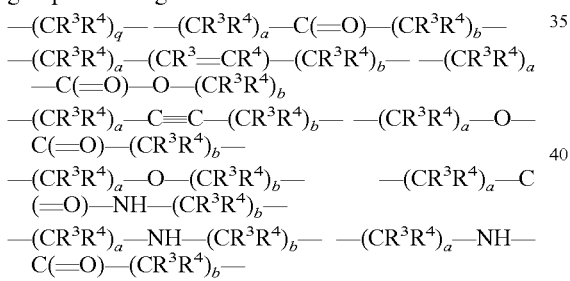

wherein
  q is 1, 2, 3 or 4;
  a and b are independently 0, 1, 2 or 3;

A is selected from the group consisting of $A^1$ to $A^{116}$

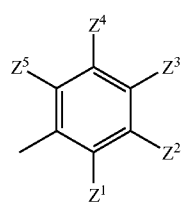
$A^1$

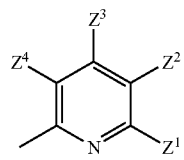
$A^2$

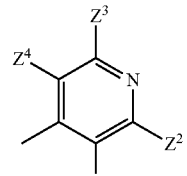
$A^3$

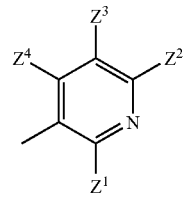
$A^4$

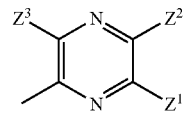
$A^5$

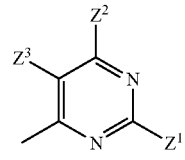
$A^6$

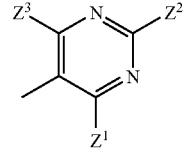
$A^7$

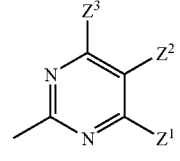
$A^8$

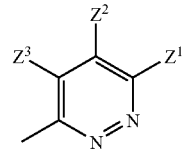
$A^9$

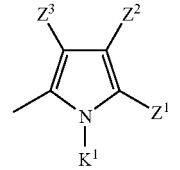
$A^{10}$ $A^{11}$

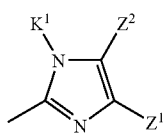 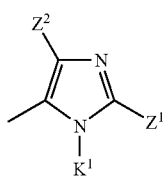 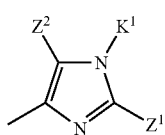 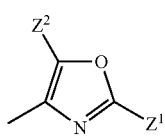 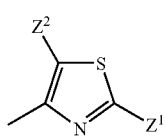 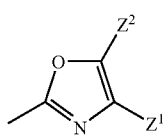 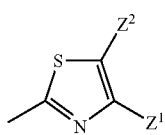 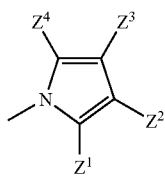 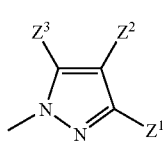 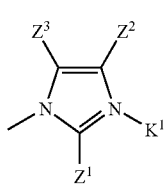 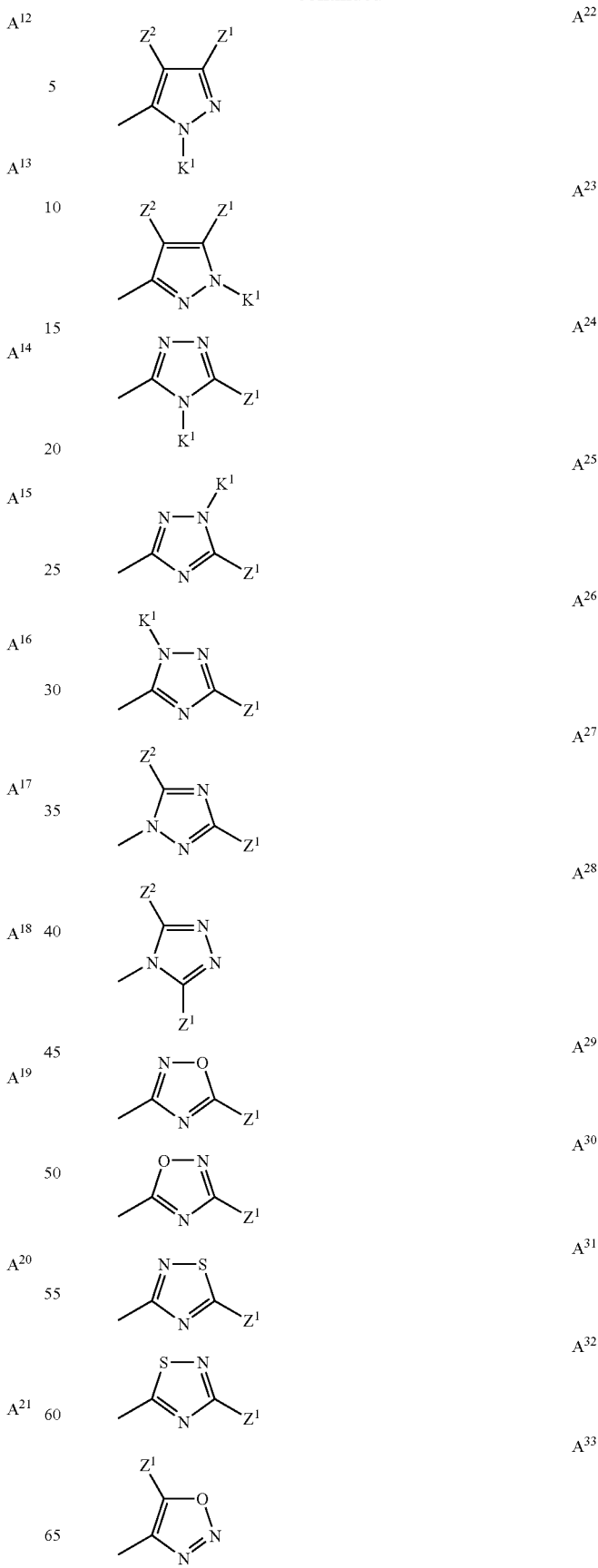

-continued
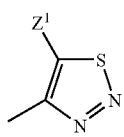
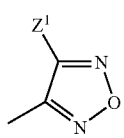
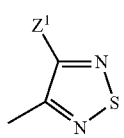
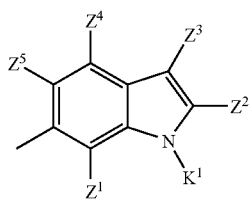
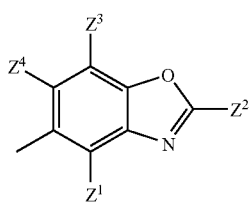
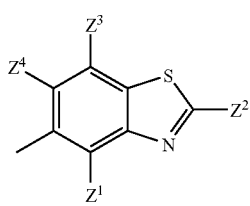
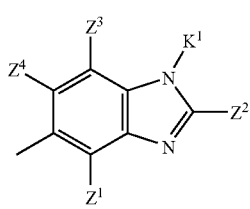
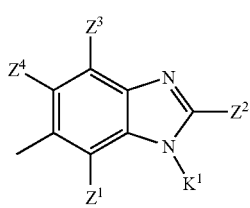
-continued
$A^{34}$
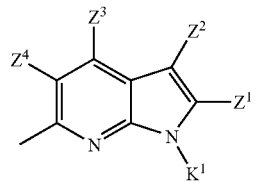
$A^{35}$
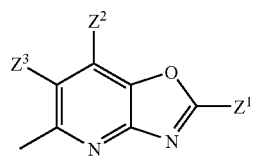
$A^{36}$
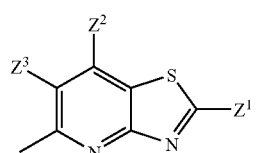
$A^{37}$
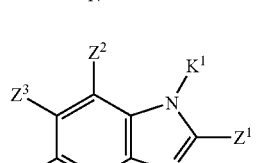
$A^{38}$
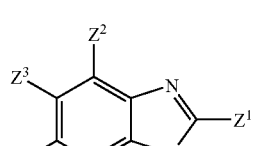
$A^{39}$
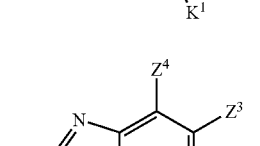
$A^{40}$
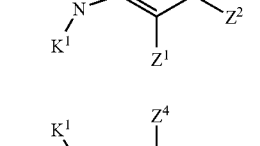
$A^{41}$
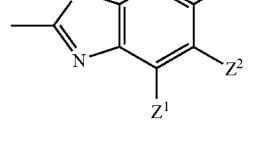
$A^{42}$
$A^{43}$
$A^{44}$
$A^{45}$
$A^{46}$
$A^{47}$
$A^{48}$
$A^{49}$
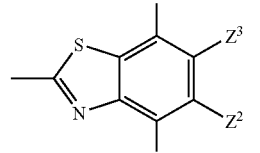

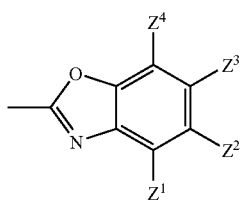 A50
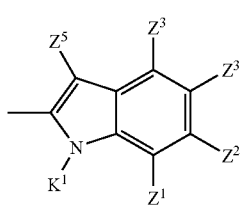 A51
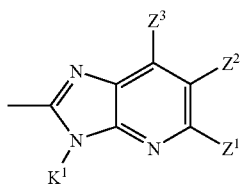 A52
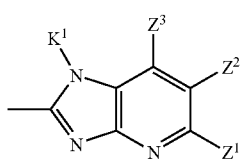 A53
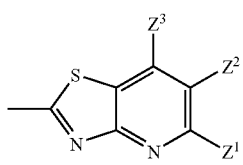 A54
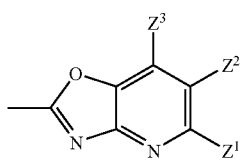 A55
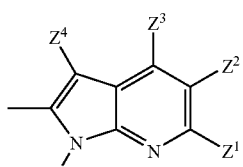 A56
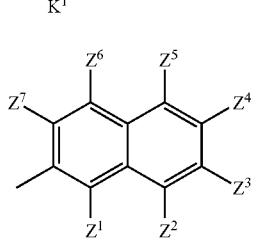 A57
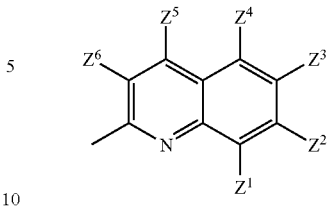 A58
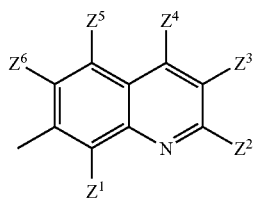 A59
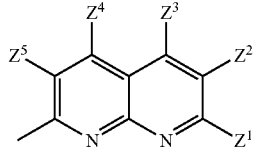 A60
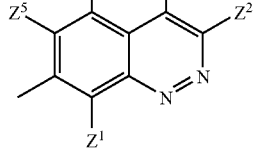 A61
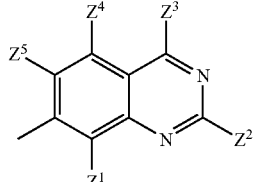 A62
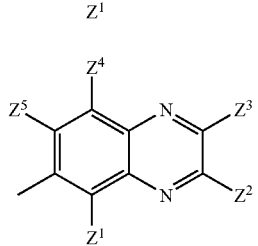 A63
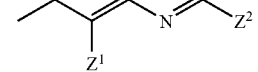 A64
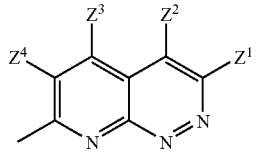 A65

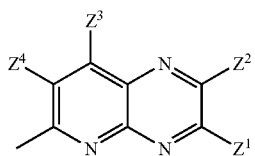
A66
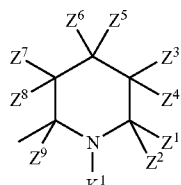
A67
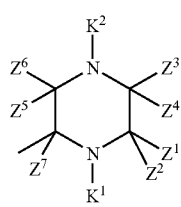
A68
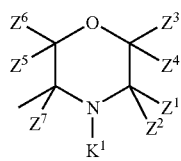
A69
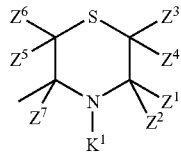
A70
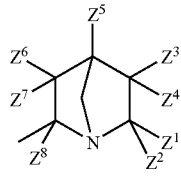
A71
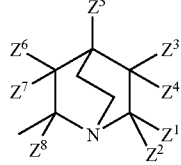
A72
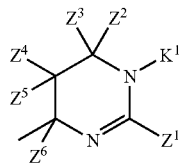
A73
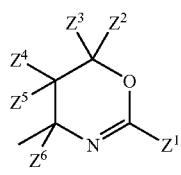
A74
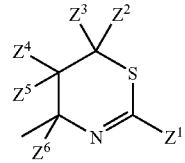
A75
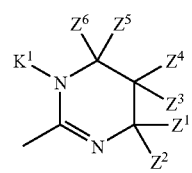
A76
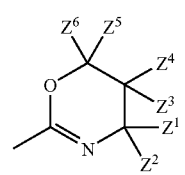
A77
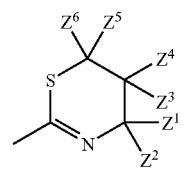
A78
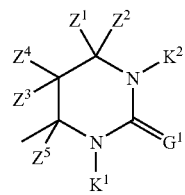
A79
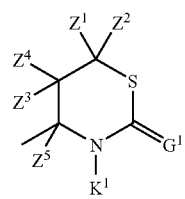
A80
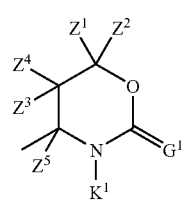
A81
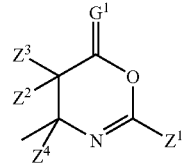
A82

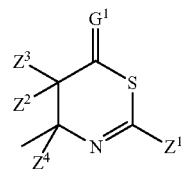 A83
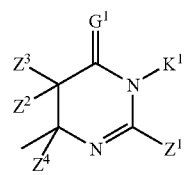 A84
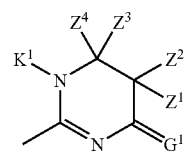 A85
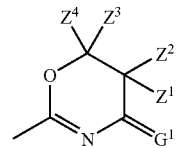 A86
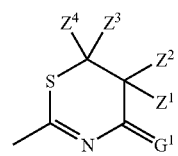 A87
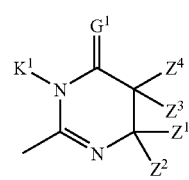 A88
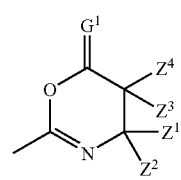 A89
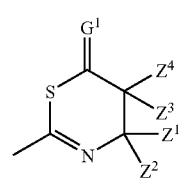 A90
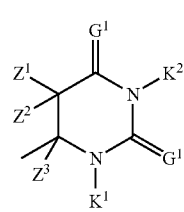 A91
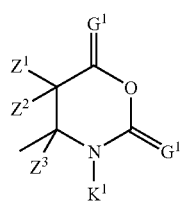 A92
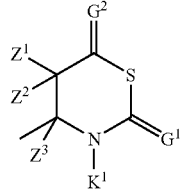 A93
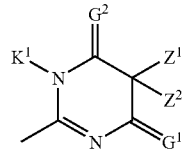 A94
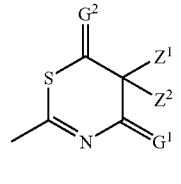 A95
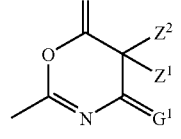 A96
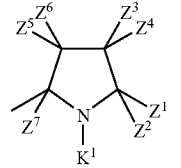 A97
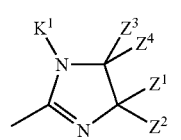 A98
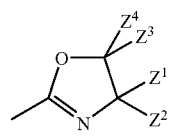 A99
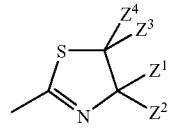 A100

-continued

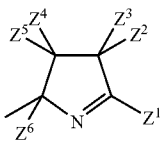 A[101]

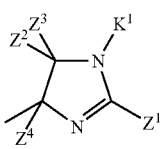 A[102]

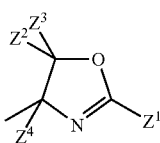 A[103]

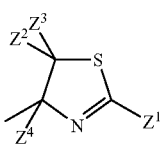 A[104]

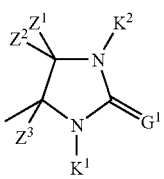 A[105]

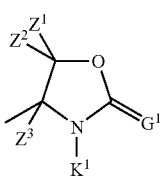 A[106]

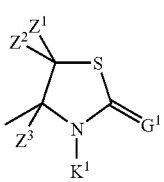 A[107]

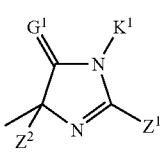 A[108]

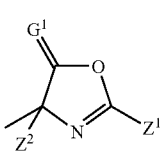 A[109]

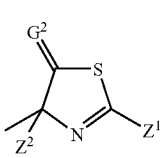 A[110]

-continued

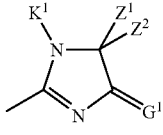 A[111]

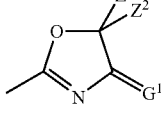 A[112]

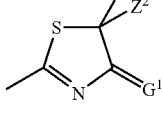 A[113]

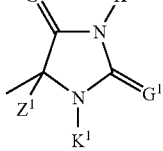 A[114]

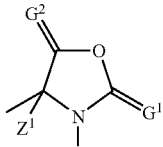 A[115]

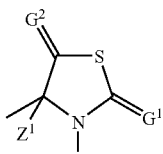 A[116]

wherein $Z^1$, $Z^2$, $Z^3$, $Z^4$, $Z^5$, $Z^6$, $Z^7$, $Z^8$ and $Z^9$ are independently selected from the group consisting of hydrogen, halogen, [$C_1$-$C_8$]-alkyl, [$C_1$-$C_8$]-haloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_3$-$C_6$]-cycloalkyl, [$C_3$-$C_6$]-halocycloalkyl, aryl, aryl-[$C_1$-$C_8$]-alkyl, hydroxy-[$C_1$-$C_8$]-alkyl, [$C_1$-$C_8$]-alkoxy-[$C_1$-$C_8$]-alkyl, —C(=O)$R^5$, —C(=O)O$R^5$, —C(=O)N$R^5R^6$, —C(=O)S$R^5$, —C(=S)$R^5$, —C(=S)O$R^5$, —C(=S)N$R^5R^6$, —C(=S)S$R^5$, —C$R^5$=N$R^6$, —C$R^5$=NO$R^6$, —C$R^5$=N—N$R^6R^2$, —O$R^5$, —OSi$R^5R^6R^7$, —OC(=O)$R^5$, —OC(=O)O$R^5$, —OC(=O)N$R^5R^6$, —OC(=S)N$R^5R^6$, —N$R^5R^6$, —N($R^5$)C(=O)$R^6$, —N($R^5$)C(=O)O$R^6$, —N($R^5$)C(=O)N$R^6R^7$, —N($R^5$)C(=S)$R^6$, —N($R^5$)C(=S)N$R^6R^7$, —N=C$R^5R^6$, —N=C—N$R^5R^6$, —N($R^5$)C(=N$R^6$)N$R^7R^8$, —N($R^5$)O$R^6$, —N($R^5$)N$R^6R^7$, —N=N$R^5$, —N($R^5$)S(=O)$R^6$, —N($R^5$)S(=O)$_2R^6$, —N($R^5$)S(=O)$_2$O$R^6$, —N($R^5$)S(=O)O$R^6$, —N($R^5$)S(=O)N$R^6R^7$, —N($R^5$)S(=O)$_2$N$R^6R^7$, —S$R^5$, —S(=O)$R^5$, —S(=O)$_2R^5$, —S(=O)O$R^5$, —S(=O)N$R^5R^6$, —S(=O)$_2$O$R^5$, —S(=O)$_2$N$R^5R^6$, nitro, nitroso, azido, cyano, —S$F_5$, and —Si$R^5R^6R^7$;

$K^1$ and $K^2$ are independently selected from the group consisting of hydrogen, $[C_1-C_8]$-alkyl, $[C_1-C_8]$-haloalkyl, $[C_2-C_8]$-alkenyl, $[C_2-C_8]$-haloalkenyl, $[C_2-C_8]$-alkynyl, $[C_2-C_8]$-haloalkynyl, $[C_3-C_6]$-cycloalkyl, $[C_3-C_6]$-halocycloalkyl, aryl, hydroxy-$[C_1-C_8]$-alkyl, $[C_1-C_8]$-alkoxy-$[C_1-C_8]$-alkyl, —C(=O)R$^9$, —C(=O)OR$^9$, —C(=O)NR$^9$R$^{10}$, —C(=O)SR$^9$, —C(=S)R$^9$, —C(=S)OR$^9$, —C(=S)NR$^9$R$^{10}$, —C(=S)SR$^9$, —CR$^9$=NR$^{10}$, —CR$^9$=NOR$^{10}$, —CR$^9$=N—NR$^{10}$R$^{11}$, —S(=O)R$^9$, —S(=O)$_2$R$^9$, —S(=O)OR$^9$, —S(=O)NR$^9$R$^{10}$, —S(=O)$_2$OR$^9$, —S(=O)$_2$NR$^9$R$^{10}$, and —SiR$^9$R$^{10}$R$^{11}$;

$G^1$ and $G^2$ are independently selected from the group consisting of oxygen, sulfur, NR$^{12}$, N—OR$^{12}$, and N—NR$^{12}$R$^{13}$;

Q is selected from the group consisting of $Q^1$ to $Q^{28}$;

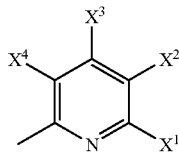 Q$^1$

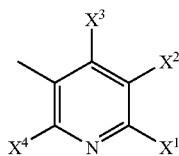 Q$^2$

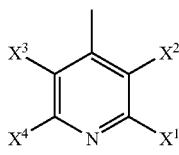 Q$^3$

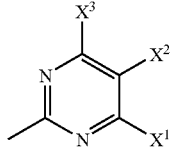 Q$^4$

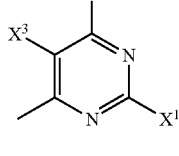 Q$^5$

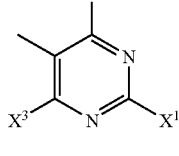 Q$^6$

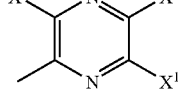 Q$^7$

-continued

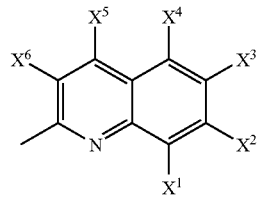 Q$^8$

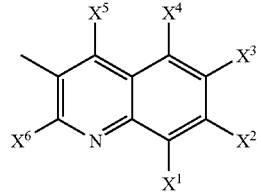 Q$^9$

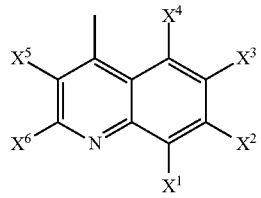 Q$^{10}$

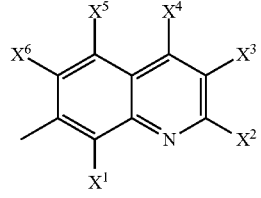 Q$^{11}$

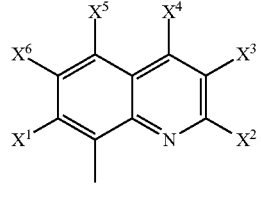 Q$^{12}$

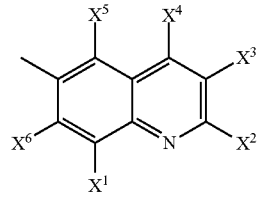 Q$^{13}$

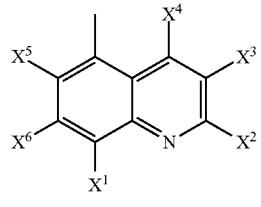 Q$^{14}$

103
-continued
Q15
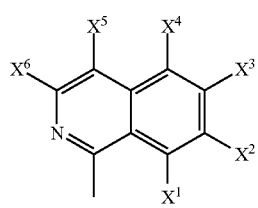
Q16
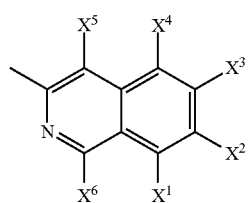
Q17
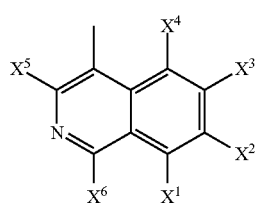
Q18
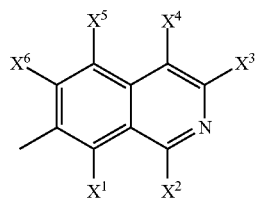
Q19
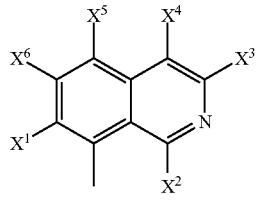
Q20
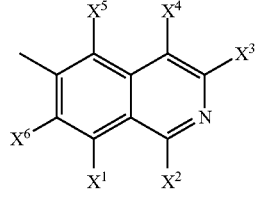
Q21
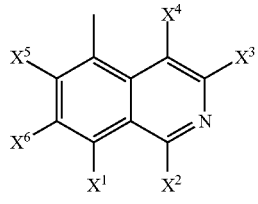
104
-continued
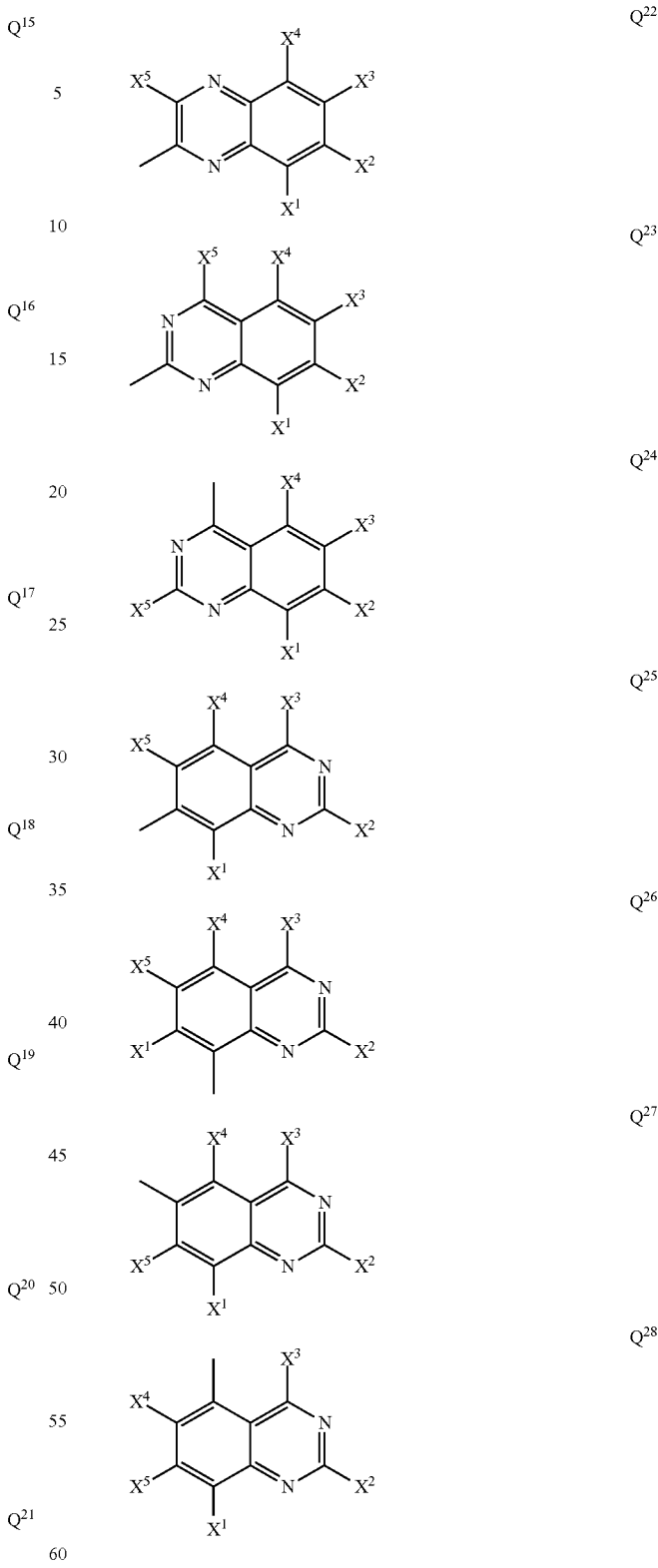
wherein
$X^1$, $X^2$, $X^3$, $X^4$, $X^5$ and $X^6$ are independently selected from the group consisting of hydrogen, halogen, $[C_1\text{-}C_8]$-alkyl, $[C_1\text{-}C_8]$-haloalkyl, $[C_2\text{-}C_8]$-alkenyl, $[C_2\text{-}C_8]$-haloalkenyl, $[C_2\text{-}C_8]$-alkynyl, $[C_2\text{-}C_8]$-haloalkynyl, $[C_3\text{-}C_6]$-cycloalkyl, $[C_3\text{-}C_6]$-halocycloalkyl, aryl, aryl-$[C_1-C_8]$-alkyl, hydroxy-$[C_1-C_8]$-alkyl, $[C_1-C_8]$-alkoxy-$[C_1-C_8]$-alkyl, —C(=O)$R^{14}$, —C(=O)O$R^{14}$, —C(=O)N$R^{14}R^{15}$, —C(=O)S$R^{14}$, —C(=S)$R^{14}$, —C(=S)O$R^{14}$, —C(=S)N$R^{14}R^{15}$, —C(=S)S$R^{15}$, —C$R^{14}$=N$R^{15}$, —C$R^{14}$=NO$R^{15}$, —C$R^{14}$=N—N$R^{15}R^{16}$, —O$R^{14}$, —OSi$R^{14}R^{15}R^{16}$, —OC(=O)$R^{14}$, —OC(=O)O$R^{14}$, —OC(=O)N$R^{14}R^{15}$, —OC(=S)N$R^{14}R^{15}$, —N$R^{14}R^{15}$, —N($R^{14}$)C(=O)$R^{15}$, —N($R^{14}$)C(=O)O$R^{15}$, —N($R^{14}$)C(=O)N$R^{15}R^{16}$, —N($R^{14}$)C(=S)$R^{15}$, —N($R^{14}$)C(=S)N$R^{15}R^{16}$, —N=C$R^{14}R^{15}$, —N=C—N$R^{14}R^{15}$, —N($R^{14}$)C(=N$R^{15}$)N$R^{16}R^{17}$, —N($R^{14}$)O$R^{15}$, —N($R^{14}$)N$R^{15}R^{16}$, —N=N$R^{14}$, —N($R^{14}$)S(=O)$R^{15}$, —N($R^{14}$)S(=O)$_2R^{15}$, —N($R^{14}$)S(=O)$_2$O$R^{15}$, —N($R^{14}$)S(=O)O$R^{15}$, —N($R^{14}$)S(=O)N$R^{15}R^{16}$, —N($R^{14}$)S(=O)$_2$N$R^{15}R^{16}$, —S$R^{14}$, —S(=O)$R^{14}$, —S(=O)$_2R^{14}$, —S(=O)O$R^{14}$, —S(=O)N$R^{14}R^{15}$, —S(=O)$_2$O$R^{14}$, —S(=O)$_2$N$R^{14}R^{15}$, nitro, nitroso, azido, cyano, —SF$_5$, and —Si$R^{14}R^{15}R^{16}$;

$R^1$, $R^2$, $R^3$ and $R^4$ are independently selected from the group consisting of hydrogen, halogen, $[C_1-C_4]$-alkyl, $[C_1-C_4]$-haloalkyl, $[C_2-C_4]$-alkenyl, $[C_2-C_4]$-haloalkenyl, $[C_2-C_4]$-alkynyl, $[C_2-C_4]$-haloalkynyl, $[C_3-C_5]$-cycloalkyl, $[C_3-C_5]$-halocycloalkyl, $[C_1-C_4]$-alkoxy, $[C_1-C_4]$-alkoxy-$[C_1-C_4]$-alkoxy, $[C_1-C_4]$-haloalkoxy, $[C_1-C_4]$-haloalkoxy-$[C_1-C_4]$-alkyl, and cyano;

$R^5$ to $R^{17}$ are independently selected from the group consisting of hydrogen, $[C_1-C_8]$-alkyl, $[C_1-C_8]$-haloalkyl, $[C_2-C_8]$-alkenyl, $[C_2-C_8]$-haloalkenyl, $[C_2-C_8]$-alkynyl, $[C_2-C_8]$-haloalkynyl, $[C_3-C_6]$-cycloalkyl, $[C_3-C_6]$-halocycloalkyl, aryl, and aryl-$[C_1-C_8]$-alkyl;

or a salt, an N-oxide, a metallic complex or a metalloidic complex thereof.

2. The compound of claim 1 wherein $L^1$ is a direct bond or a divalent group selected from the group consisting of
—(C$R^1R^2$)$_n$— —C(=O)— (C$R^1R^2$)$_p$—
—(C$R^1R^2$)$_m$—O— —(C$R^1R^2$)$_m$—C(=O)—
—(C$R^1R^2$)$_m$—NH— —(C$R^1R^2$)$_m$—C(=O)—NH—
—(C$R^1R^2$)$_m$—C(=O)— —(C$R^1R^2$)$_m$—NH—C(=O)—
wherein
n is 1 or 2;
m and p are independently 0 or 1;
$R^1$ and $R^2$ are independently selected from the group consisting of hydrogen, halogen, $[C_1-C_4]$-alkyl, $[C_1-C_4]$-haloalkyl, $[C_2-C_4]$-alkenyl, $[C_2-C_4]$-alkynyl, $[C_3-C_5]$-cycloalkyl, $[C_1-C_4]$-alkoxy, $[C_1-C_4]$-haloalkoxy, and cyano.

3. The compound of claim 2 wherein
$L^1$ is a direct bond or a divalent group selected from the group consisting of —(C$R^1R^2$)—, —C(=O)—(C$R^1R^2$)—, and —C(=O)—; wherein
$R^1$ and $R^2$ are independently selected from the group consisting of hydrogen, halogen, methyl, ethyl, iso-propyl, trifluoromethyl, difluoromethyl, allyl, ethynyl, propargyl, cyclopropyl, methoxy, trifluoromethoxy, and cyano.

4. The compound of claim 1 wherein
$L^2$ is a direct bond or a divalent group selected from the group consisting of
—(C$R^3R^4$)$_q$— —(C$R^3R^4$)$_a$—C(=O)—
—(C$R^3$=C$R^4$)— —(C$R^3R^4$)$_a$—C(=O)—O—
—C≡C— —(C$R^3R^4$)$_a$—O—C(=O)—
—(C$R^3R^4$)$_a$—O— —(C$R^3R^4$)$_a$—C(=O)—NH—
—(CR$R^3R^4$)$_a$—NH— —(C$R^3R^4$)$_a$—NH—C(=O)—
wherein
q and a are independently 1 or 2;
$R^3$ and $R^4$ are independently selected from the group consisting of hydrogen, halogen, $[C_1-C_4]$-alkyl, $[C_1-C_4]$-haloalkyl, $[C_2-C_4]$-alkenyl, $[C_2-C_4]$-alkynyl, $[C_3-C_5]$-cycloalkyl, $[C_1-C_4]$-alkoxy, $[C_1-C_4]$-haloalkoxy, and cyano.

5. The compound of claim 4 wherein
$L^2$ is a direct bond or —(C$R^3R^4$)— wherein
$R^3$ and $R^4$ are independently selected from the group consisting of hydrogen, halogen, methyl, ethyl, iso-propyl, trifluoromethyl, difluoromethyl, allyl, ethynyl, propargyl, cyclopropyl, methoxy, trifluoromethoxy, and cyano.

6. The compound of claim 1 wherein A is selected from the group consisting of $A^1$ to $A^{32}$.

7. The compound of claim 6 wherein A is selected from the group consisting of $A^2$, $A^6$, $A^8$, $A^{15}$, $A^{16}$, $A^{17}$, and $A^{18}$.

8. The compound of claim 1 wherein
$Z^1$ is selected from the group consisting of hydrogen, —C(=O)$R^5$, —C(=O)O$R^5$, —C(=O)N$R^5R^6$, —C(=S)N$R^5R^6$, —C$R^5$=N$R^6$, —C$R^5$=NO$R^6$, —C$R^5$=N—N$R^6R^7$, —O$R^5$, —OC(=O)$R^5$, —OC(=O)O$R^5$, —OC(=O)N$R^5R^6$, —OC(=S)N$R^5R^6$, —N$R^5R^6$, —N($R^5$)C(=O)$R^6$, —N($R^5$)C(=O)O$R^6$, —N($R^5$)C(=O)N$R^6R^7$, —N($R^5$)C(=S)$R^6$, —N($R^5$)C(=S)N$R^6R^7$, —N=C$R^5R^6$, —N=C—N$R^5R^6$, —N($R^5$)C(=N$R^6$)N$R^7R^8$, —N($R^5$)O$R^6$, —N($R^5$)N$R^6R^7$, —N=N$R^5$, —N($R^5$)S(=O)$_2R^6$, —N($R^5$)S(=O)$_2$O$R^6$, —N($R^5$)S(=O)$_2$N$R^6R^7$, —S$R^5$, —S(=O)$_2R^5$, —S(=O)$_2$O$R^5$, —S(=O)$_2$N$R^5R^6$, and cyano.

9. The compound of claim 1 wherein
$Z^1$ is selected from the group consisting of hydrogen, —N$R^5R^6$, —N($R^5$)C(=O)$R^6$, —N($R^5$)C(=O)O$R^6$—N($R^5$)C(=O)N$R^6R^7$, —N($R^5$)C(=S)N$R^6R^7$, —N=C$R^5R^6$, —N=C—N$R^5R^6$, —N($R^5$)C(=N$R^6$)N$R^7R^8$, —N($R^5$)S(=O)$_2R^6$, —N($R^5$)S(=O)$_2$O$R^6$, —N($R^5$)S(=O)$_2$N$R^6R^7$, and cyano.

10. The compound of claim 1 wherein
$Z^2$, $Z^3$, $Z^4$, $Z^5$, $Z^6$, $Z^7$, $Z^8$ and $Z^9$ are independently selected from the group consisting of hydrogen, halogen, $[C_1-C_4]$-alkyl, $[C_1-C_4]$-haloalkyl, $[C_2-C_4]$-alkenyl, $[C_2-C_4]$-haloalkenyl, $[C_2-C_4]$-alkynyl, $[C_2-C_4]$-haloalkynyl, $[C_3-C_5]$-cycloalkyl, —C(=O)$R^5$, —C(=O)O$R^5$, —C(=O)N$R^5R^6$, —O$R^5$, —OSi$R^5R^6R^7$, —OC(=O)$R^5$, —N$R^5R^6$, —N($R^5$)C(=O)$R^6$, —S$R^5$, —S(=O)$_2R^5$, —S(=O)$_2$O$R^5$, —S(=O)$_2$N$R^5R^6$, cyano and —Si$R^5R^6R^7$; wherein
$R^5$, $R^6$, and $R^7$ are independently selected from the group consisting of hydrogen, $[C_1-C_4]$-alkyl, $[C_1-C_4]$-haloalkyl, $[C_2-C_4]$-alkenyl, $[C_2-C_4]$-haloalkenyl, $[C_2-C_4]$-alkynyl, $[C_2-C_4]$-haloalkynyl, and $[C_3-C_5]$-cycloalkyl.

11. The compound of claim 10 wherein
$Z^2$, $Z^3$, $Z^4$, $Z^5$, $Z^6$, $Z^7$, $Z^8$ and $Z^9$ are independently selected from the group consisting of hydrogen, halogen, methyl, ethyl, iso-propyl, iso-butyl, tert-butyl, trifluoromethyl, difluoromethyl, allyl, ethynyl, propargyl, cyclopropyl, methoxy, trifluoromethoxy, acetyl, trifluoroacetyl, and cyano.

12. The compound of claim 1 wherein $K^1$ and $K^2$ are independently selected from the group consisting of hydrogen, $[C_1-C_4]$-alkyl, methyl, ethyl, iso-propyl, iso-butyl, tert-butyl, allyl, propargyl, cyclopropyl, acetyl, trifluoroacetyl, and mesyl.

13. The compound of claim 1 wherein Q is selected from the group consisting of $Q^1$ to $Q^{14}$.

14. The compound of claim 13 wherein Q is selected from the group consisting of $Q^1$ to $Q^6$.

15. The compound of claim 1 wherein $X^1$ to $X^6$ are independently selected from the group consisting of hydrogen, halogen, $[C_1\text{-}C_4]$-alkyl, $[C_1\text{-}C_4]$haloalkyl, $[C_2\text{-}C_4]$-alkenyl, $[C_2\text{-}C_4]$-haloalkenyl, $[C_2\text{-}C_4]$-alkynyl, $[C_2\text{-}C_4]$-haloalkynyl, $[C_3\text{-}C_5]$-cycloalkyl, $[C_3\text{-}C_5]$-halocycloalkyl, aryl, aryl-$[C_1\text{-}C_2]$-alkyl, $-C(=O)R^{14}$, $-C(=O)OR^{14}$, $-C(=O)NR^{14}R^{15}$, $-CR^{14}=NOR^{15}$, $-CR^{14}=N-NR^{15}R^{16}$, $-OR^{14}$, $-OSiR^{14}R^{15}R^{16}$, $-OC(=O)R^{14}$, $-OC(=O)OR^{14}$, $-OC(=O)NR^{14}R^{15}$, $-NR^{14}R^{15}$, $-N(R^{14})C(=O)R^{15}$, $-SR^{14}$, $-S(=O)_2R^{14}$, $-S(=O)_2OR^{14}$, $-S(=O)_2NR^{14}R^{15}$, cyano, and $-SiR^{14}R^{15}R^{16}$;

wherein $R^{14}$, $R^{15}$, and $R^{16}$ are independently selected from the group consisting of hydrogen, $[C_1\text{-}C_4]$-alkyl, $[C_2\text{-}C_4]$-alkenyl, $[C_2\text{-}C_4]$-haloalkenyl, $[C_2\text{-}C_4]$-alkynyl, $[C_2\text{-}C_4]$-haloalkynyl, $[C_3\text{-}C_5]$-cycloalkyl, aryl, and aryl-$[C_1\text{-}C_2]$-alkyl.

16. The compound of claim 15 wherein $X^1$ to $X^6$ are independently selected from the group consisting of hydrogen, halogen, methyl, iso-propyl, iso-butyl, tert-butyl, trifluoromethyl, difluoromethyl, allyl, ethynyl, propargyl, cyclopropyl, benzyl, phenethyl, methoxy, trifluoromethoxy, acetyl, trifluoroacetyl, and cyano.

17. The compound of claim 1 wherein T is selected from the group consisting of

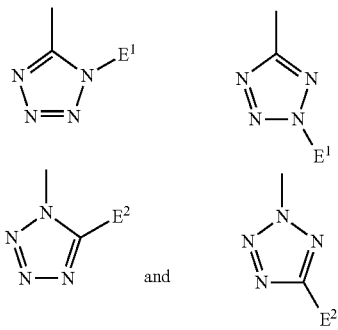

and wherein $E^1$ is selected from the group consisting of hydrogen, $[C_1\text{-}C_8]$-alkyl, $[C_1\text{-}C_8]$-haloalkyl, $[C_2\text{-}C_8]$-alkenyl, $[C_2\text{-}C_8]$-haloalkenyl, $[C_2\text{-}C_8]$-alkynyl, $[C_2\text{-}C_8]$-haloalkynyl, $[C_3\text{-}C_6]$-cycloalkyl, $[C_3\text{-}C_6]$-halocycloalkyl, aryl, aryl-$[C_1\text{-}C_8]$-alkyl, hydroxy-$[C_1\text{-}C_8]$-alkyl, $[C_1\text{-}C_8]$-alkoxy-$[C_1\text{-}C_8]$-alkyl, $-C(=O)R^{18}$, $-C(=O)OR^{18}$, $-C(=O)NR^{18}R^{19}$, $-C(=O)SR^{18}$, $-C(=S)R^{18}$, $-C(=S)OR^{18}$, $-C(=S)NR^{18}R^{19}$, $-C(=S)SR^{18}$, $-CR^{18}=NR^{19}$, $-CR^{18}=NOR^{19}$, $-CR^{18}=N-NR^{19}R^{20}$, $-S(=O)R^{18}$, $-S(=O)_2R^{18}$, $-S(=O)OR^{18}$, $-S(=O)NR^{18}R^{19}$, $-S(=O)_2OR^{18}$, $-S(=O)_2NR^{18}R^{19}$, cyano, and $-SiR^{18}R^{19}R^{20}$;

$E^2$ is selected from the group consisting of hydrogen, halogen, $[C_1\text{-}C_8]$-alkyl, $[C_1\text{-}C_8]$-haloalkyl, $[C_2\text{-}C_8]$-alkenyl, $[C_2\text{-}C_8]$-haloalkenyl, $[C_2\text{-}C_8]$-alkynyl, $[C_2\text{-}C_8]$-haloalkynyl, $[C_3\text{-}C_6]$-cycloalkyl, $[C_3\text{-}C_6]$-halocycloalkyl, aryl, aryl[$C_1\text{-}C_8$]-alkyl, hydroxy-$[C_1\text{-}C_8]$-alkyl, $[C_1\text{-}C_8]$-alkoxy-$[C_1\text{-}C_8]$-alkyl, $-C(=O)R^{18}$, $-C(=O)OR^{18}$, $-C(=O)NR^{18}R^{19}$, $-C(=O)SR^{18}$, $-C(=S)R^{18}$, $-C(=S)OR^{18}$, $-C(=S)NR^{18}R^{19}$, $-C(=S)SR^{18}$, $-CR^{18}=NR^{19}$, $-CR^{18}=NOR^{19}$, $-CR^{18}=N-NR^{19}R^{20}$, $-OR^{18}$, $-OSiR^{18}R^{19}R^{20}$, $-OC(=O)R^{18}$, $-OC(=O)OR^{18}$, $-OC(=O)NR^{18}R^{19}$, $-OC(=S)NR^{18}R^{19}$, $-NR^{18}R^{19}$, $-N(R^{18})C(=O)R^{19}$, $-N(R^{18})C(=O)OR^{19}$, $-N(R^{18})C(=O)NR^{19}R^{20}$, $-N(R^{18})C(=S)R^{19}$, $-N(R^{18})C(=S)NR^{19}R^{20}$, $-N=CR^{18}R^{19}$, $-N=C-NR^{18}R^{19}$, $-N(R^{18})C(=NR^{19})NR^{20}R^{21}$, $-N(R^{18})OR^{19}$, $-N(R^{18})NR^{19}R^{20}$, $-N=NR^{18}$, $-N(R^{18})S(=O)R^{19}$, $-N(R^{18})S(=O)_2R^{19}$, $-N(R^{18})S(=O)_2OR^{19}$, $-N(R^{18})S(=O)OR^{19}$, $-N(R^{18})S(=O)NR^{19}R^{20}$, $-N(R^{18})S(=O)_2NR^{19}R^{20}$, $-S(=O)R^{18}$, $-S(=O)_2R^{18}$, $-S(=O)OR^{18}$, $-S(=O)NR^{18}R^{19}$, $-S(=O)_2OR^{18}$, $-S(=O)_2NR^{18}R^{19}$, cyano, $-SF_5$, and $SiR^{18}R^{19}R^{20}$; and $R^{18}$ to $R^{20}$ are independently selected from the group consisting of hydrogen, $[C_1\text{-}C_8]$-alkyl, $[C_1\text{-}C_8]$-haloalkyl, $[C_2\text{-}C_8]$-alkenyl, $[C_2\text{-}C_8]$-haloalkenyl, $[C_2\text{-}C_8]$-alkynyl, $[C_2\text{-}C_8]$-haloalkynyl, $[C_3\text{-}C_6]$-cycloalkyl, $[C_3\text{-}C_6]$-halocycloalkyl, aryl, and aryl-$[C_1\text{-}C_8]$-alkyl.

18. The compound of claim 17 wherein $L^1$ is a direct bond or a divalent group selected from the group consisting of $-(CR^1R)_n-$ $-C(=O)-(CR^1R^2)_p-$
$-(CR^1R^2)_m-O-$ $-(CR^1R^2)_m-C(=O)-O-$
$-(CR^1R^2)_m-NH-$ $-(CR^1R^2)_m-C(=O)-NH-$
$-(CR^1R^2)_m-C(=O)-$ $-(CR^1R^2)_m-NH-C(=O)-$ wherein n is 1 or 2;

m and p are independently 0 or 1;

$R^1$ and $R^2$ are independently selected from the group consisting of hydrogen, halogen, $[C_1\text{-}C_4]$-alkyl, $[C_1\text{-}C_4]$-haloalkyl, $[C_2\text{-}C_4]$-alkenyl, $[C_2\text{-}C_4]$-alkynyl, $[C_3\text{-}C_5]$-cycloalkyl, $[C_1\text{-}C_4]$-alkoxy, $[C_1\text{-}C_4]$-haloalkoxy, and cyano;

$L^2$ is a direct bond or a divalent group selected in the list consisting of $-(CR^3R^4)_q-$, $-(CR^3R^4)_a-C(=O)-$, $-(CR^3=CR^4)-$, $-(CR^3R^4)_a-C(=O)-O-$, $-C\equiv C-$, $-(CR^3R^4)_a-O-C(=O)-$, $-(CR^3R^4)_a-O-$, $-(CR^3R^4)_a-C(=O)-NH-$, $-(CR^3R^4)_a-NH-$, and $-(CR^3R^4)_a-NH-C(=O)-$ wherein q and a are independently 1 or 2;

$R^3$ and $R^4$ are independently selected from the group consisting of hydrogen, halogen, $[C_1\text{-}C_4]$-alkyl, $[C_1\text{-}C_4]$-haloalkyl, $[C_2\text{-}C_4]$-alkenyl, $[C_2\text{-}C_4]$-alkynyl, $[C_3\text{-}C_5]$-cycloalkyl, $[C_1\text{-}C_4]$-alkoxy, $[C_1\text{-}C_4]$-haloalkoxy, and cyano;

A is selected from the group consisting of $A^1$ to $A^{32}$;

$Z^1$ is selected from the group consisting of hydrogen, $-C(=O)R^5$, $-C(=O)OR^5$, $-C(=O)NR^5R^6$, $-C(=S)NR^5R^6$, $-CR^5=NR^6$, $-CR^5=NOR^6$, $-CR^5=N-NR^6R^7$, $-OR^5$, $-OC(=O)R^5$, $-OC(=O)OR^5$, $-OC(=O)NR^5R^6$, $-OC(=S)NR^5R^6$, $-NR^5R^6$, $-N(R^5)C(=O)R^6$, $-N(R^5)C(=O)OR^6$, $-N(R^5)C(=O)NR^6R^7$, $-N(R^5)C(=S)R^6$, $-N(R^5)C(=S)NR^6R^7$, $-N=CR^5R^6$, $-N=C-NR^5R^6$, $-N(R^5)C(=NR^6)NR^7R^8$, $-N(R^5)OR^6$, $-N(R^5)NR^6R^7$, $-N=NR^5$, $-N(R^5)S(=O)_2R^6$, $-N(R^5)S(=O)_2OR^6$, $-N(R^5)S(=O)_2NR^6R^7$, $-SR^5$, $-S(=O)_2R^5$, $-S(=O)_2OR^5$, $-S(=O)_2NR^5R^6$, and cyano;

$Z^2$, $Z^3$, $Z^4$ and $Z^5$ are independently selected from the group consisting of hydrogen, halogen, $[C_1\text{-}C_4]$-alkyl, $[C_1\text{-}C_4]$-haloalkyl, $[C_2\text{-}C_4]$-alkenyl, $[C_2\text{-}C_4]$-haloalkenyl, $[C_2\text{-}C_4]$-alkynyl, $[C_2\text{-}C_4]$-haloalkynyl, $[C_3\text{-}C_5]$-cycloalkyl, $-C(=O)R^5$, $-C(=O)OR^5$, $-C(=O)NR^5R^6$, $-OR^5$, $-OSiR^5R^6R^7$, $-OC(=O)R^5$, —$NR^5R^6$, —$N(R^5)C(=O)R^6$, —$SR^5$, —$S(=O)_2R^5$, —$S(=O)_2OR^5$, —$S(=O)_2NR^5R^6$, cyano, and —$SiR^5R^6R^7$;

wherein $R^5$, $R^6$, and $R^7$ are independently selected from the group consisting of hydrogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, and [$C_3$-$C_5$]-cycloalkyl;

$K^1$ is selected from the group consisting of hydrogen, methyl, ethyl, iso-propyl, iso-butyl, tert-butyl, allyl, propargyl, cyclopropyl, acetyl, trifluoroacetyl, and mesyl;

Q is selected from the group consisting of $Q^1$ to $Q^{14}$; and $X^1$ to $X^6$ are independently selected from the group consisting of hydrogen, halogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, [$C_3$-$C_5$]-halocycloalkyl, aryl, aryl-[$C_1$-$C_2$]-alkyl, —$C(=O)R^{14}$, —$C(=O)OR^{14}$, —$C(=O)NR^{14}R^{15}$, —$CR^{14}=NOR^{15}$, —$CR^{14}=N-NR^{15}R^{16}$, —$OR^{14}$, —$OSiR^{14}R^{15}R^{16}$, —$OC(=O)R^{14}$, —$OC(=O)OR^{14}$, —$OC(=O)NR^{14}R^{15}$, —$NR^{14}R^{15}$, —$N(R^{14})C(=O)R^{15}$, —$SR^{14}$, —$S(=O)_2R^{14}$, —$S(=O)_2OR^{14}$, —$S(=O)_2NR^{14}R^{15}$, cyano, and —$SiR^{14}R^{15}R^{16}$;

wherein $R^{14}$, $R^{15}$, and $R^{16}$ are independently selected from the group consisting of hydrogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl and [$C_3$-$C_5$]-cycloalkyl, aryl, and aryl-[$C_1$-$C_2$]-alkyl.

19. The compound of claim 18 wherein $L^1$ is a direct bond or a divalent group selected from the group consisting of —$(CR^1R^2)$—, —$C(=O)$—$(CR^1R^2)$—, and —$C(=O)$—;

$L^2$ is a direct bond or —$(CR^3R^4)$—;

wherein $R^1$, $R^2$, $R^3$ and $R^4$ are independently selected from the group consisting of hydrogen, halogen, methyl, ethyl, iso-propyl, trifluoromethyl, difluoromethyl, allyl, ethynyl, propargyl, cyclopropyl, methoxy, trifluoromethoxy, and cyano;

A is selected from the group consisting of $A^2$, $A^6$, $A^8$, $A^{15}$, $A^{16}$, $A^{17}$, and $A^{18}$;

$Z^1$ is selected from the group consisting of hydrogen, —$NR^5R^6$, —$N(R^5)C(=O)R^6$, —$N(R^5)C(=O)OR^6$, —$N(R^5)C(=O)NR^6R^7$, —$N(R^5)C(=S)NR^6R^7$, —$N=CR^5R^6$, —$N=C-NR^5R^6$, —$N(R^5)C(=NR^6)NR^7R^8$, —$N(R^5)S(=O)_2R^6$, —$N(R^5)S(=O)_2OR^6$, —$N(R^5)S(=O)_2NR^6R^7$, and cyano;

$Z^2$, $Z^3$, and $Z^4$ are independently selected from the group consisting of hydrogen, halogen, methyl, ethyl, iso-propyl, iso-butyl, tert-butyl, trifluoromethyl, difluoromethyl, allyl, ethynyl, propargyl, cyclopropyl, methoxy, trifluoromethoxy, acetyl, trifluoroacetyl, and cyano;

Q is $Q^1$ to $Q^6$; and $X^1$ to $X^4$ are independently selected from the group consisting of hydrogen, halogen, methyl, iso-propyl, iso-butyl, tert-butyl, trifluoromethyl, difluoromethyl, allyl, ethynyl, propargyl, cyclopropyl, benzyl, phenethyl, methoxy, trifluoromethoxy, acetyl, trifluoroacetyl, and cyano.

20. The compound of claim 17 wherein $E^1$ is selected from the group consisting of [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, [$C_3$-$C_5$]-halocycloalkyl, —$C(=O)R^{18}$, —$C(=O)OR^{18}$, —$C(=O)NR^{18}R^{19}$, —$CR^{18}=NR^{19}$, —$CR^{18}=NOR^{19}$, —$CR^{18}=N-NR^{19}R^{20}$, —$S(=O)_2R^{18}$, —$S(=O)_2OR^{18}$, —$S(=O)_2NR^{18}R^{19}$, cyano, and —$SiR^{18}R^{19}R^{20}$;

wherein $R^{18}$, $R^{19}$ and $R^{20}$ are independently selected from the group consisting of hydrogen, [$C_1$-$C_4$]-alkyl, [$C_1$-$C_4$]-haloalkyl, and cyclopropyl.

21. The compound of claim 20 wherein $E^1$ is selected from the group consisting of methyl, ethyl, iso-propyl, allyl, propargyl, cyclopropyl, —$C(=O)R^{18}$, —$C(=O)OR^{18}$, —$C(=O)NR^{18}R^{19}$, —$CR^{18}=NR^{19}$, —$CR^{18}=NOR^{19}$, —$CR^{18}=N-NR^{19}R^{20}$, —$S(=O)_2R^{18}$, —$S(=O)_2OR^{18}$, —$S(=O)_2NR^{18}R^{19}$, and —$SiR^{18}R^{19}R^{20}$;

wherein $R^{18}$, $R^{19}$ and $R^{20}$ are independently selected from the group consisting of methyl and trifluoromethyl.

22. The compound of claim 17 wherein $E^2$ is selected from the group consisting of halogen, [$C_1$-$C_4$]-alkyl, [$C_1$-$C_4$]-haloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_3$-$C_5$]-cycloalkyl, [$C_3$-$C_5$]-halocycloalkyl, —$C(=O)R^{18}$, —$C(=O)OR^{18}$, —$C(=O)NR^{18}R^{19}$, —$CR^{18}=NOR^{19}$, —$CR^{18}=N-NR^{19}R^{20}$, —$OR^{18}$, —$OSiR^{18}R^{19}R^{20}$, —$OC(=O)R^{18}$, —$OC(=O)OR^{18}$, —$OC(=O)NR^{18}R^{19}$, —$NR^{18}R^{19}$, —$N(R^{18})C(=O)R^{19}$, —$N(R^{18})C(=O)OR^{19}$, —$N(R^{18})C(=O)NR^{19}R^{20}$, —$N(R^{18})C(=S)R^{19}$, —$N(R^{18})C(=S)NR^{19}R^{20}$, —$N=CR^{18}R^{19}$, —$N=C-NR^{18}R^{19}$, —$N(R^{18})S(=O)_2R^{19}$, —$N(R^{18})S(=O)_2OR^{19}$, —$N(R^{18})S(=O)_2NR^{19}R^{20}$, —$SR^{18}$, —$S(=O)_2R^{18}$, —$S(=O)_2OR^{18}$, —$S(=O)_2NR^{18}R^{19}$, cyano, and —$SiR^{18}R^{19}R^{20}$;

wherein $R^{18}$, $R^{19}$ and $R^{20}$ are independently selected from the group consisting of hydrogen, [$C_1$-$C_4$]-alkyl, and [$C_1$-$C_4$]-haloalkyl.

23. The compound of claim 22 wherein $E^2$ is selected from the group consisting of methyl, ethyl, iso-propyl, trifluoromethyl, difluoromethyl, allyl, ethynyl, propargyl, cyclopropyl, cyano, —$C(=O)R^{18}$, —$C(=O)OR^{18}$, —$C(=O)NR^{18}R^{19}$, —$CR^{18}=NOR^{19}$, —$CR^{18}=N-NR^{19}R^{20}$, —$OR^{18}$, —$OSiR^{18}R^{19}R^{20}$, —$OC(=O)R^{18}$, —$OC(=O)OR^{18}$, —$OC(=O)NR^{18}R^{19}$, —$NR^{18}R^{19}$, —$N(R^{18})C(=O)R^{19}$, —$N(R^{18})C(=O)OR^{19}$, —$N(R^{18})C(=O)NR^{19}R^{20}$, —$N(R^{18})C(=S)R^{19}$, —$N(R^{18})C(=S)NR^{19}R^{20}$, —$N=CR^{18}R^{19}$, —$N=C-NR^{18}R^{19}$, —$N(R^{18})S(=O)_2R^{19}$, —$N(R^{18})S(=O)_2OR^{19}$, —$N(R^{18})S(=O)_2NR^{19}R^{20}$, —$SR^{18}$, —$S(=O)_2R^{18}$, —$S(=O)_2OR^{18}$, —$S(=O)_2NR^{18}R^{19}$, and —$SiR^{18}R^{19}$, and —$SiR^{18}R^{19}R^{20}$;

wherein $R^{18}$, $R^{19}$ and $R^{20}$ are independently selected from the group consisting of hydrogen, methyl, and trifluoromethyl.

24. The compound of claim 1 used for controlling the phytopathogenic fungi of plants or crops.

25. A fungicide composition comprising, as an active ingredient, an effective amount of the compound of claim 1 and an agriculturally acceptable support, carrier, or filler.

26. The fungicide composition of claim 25 used for controlling the phytopathogenic fungi of plants or crops.

27. A method for controlling the phytopathogenic fungi of plants or crops comprising applying a compound of claim 1 to the seed, the plant or to the fruit of the plant or to the soil wherein the plant is growing or wherein it is desired to grow.

28. A method for controlling the phytopathogenic fungi of plants or crops comprising applying the fungicide composition of claim 25 to the seed, the plant, the fruit of the plant or to the soil wherein the plant is growing or wherein it is desired to grow.

* * * * *